US010306885B2

(12) United States Patent
Furuya et al.

(10) Patent No.: US 10,306,885 B2
(45) Date of Patent: Jun. 4, 2019

(54) ANTHRANILIC ACID ESTER COMPOUND OR SALT THEREOF, AGRICULTURAL AND HORTICULTURAL MICROBICIDE COMPRISING THE COMPOUND, AND METHOD FOR USING THE MICROBICIDE

(71) Applicant: Nihon Nohyaku Co., Ltd., Tokyo (JP)

(72) Inventors: Takashi Furuya, Osaka (JP); Atsushi Okada, Osaka (JP); Hiroto Harayama, Osaka (JP); Yutaka Abe, Osaka (JP); Naoto Shimizu, Osaka (JP); Eiji Yasukouchi, Osaka (JP); Yutaka Kato, Osaka (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 15/572,107

(22) PCT Filed: May 12, 2016

(86) PCT No.: PCT/JP2016/064156
§ 371 (c)(1),
(2) Date: Nov. 6, 2017

(87) PCT Pub. No.: WO2016/182021
PCT Pub. Date: Nov. 17, 2016

(65) Prior Publication Data
US 2018/0132482 A1   May 17, 2018

(30) Foreign Application Priority Data

May 13, 2015   (JP) .................................. 2015-097919
Aug. 28, 2015   (JP) .................................. 2015-168575

(51) Int. Cl.
| | |
|---|---|
| *A01N 37/46* | (2006.01) |
| *A01N 41/10* | (2006.01) |
| *A01N 43/40* | (2006.01) |
| *A01N 47/02* | (2006.01) |
| *C07C 317/44* | (2006.01) |
| *C07C 317/46* | (2006.01) |
| *C07C 321/28* | (2006.01) |

(Continued)

(52) U.S. Cl.
CPC ............. *A01N 37/46* (2013.01); *A01N 41/10* (2013.01); *A01N 43/40* (2013.01); *A01N 47/02* (2013.01); *C07C 317/44* (2013.01); *C07C 317/46* (2013.01); *C07C 321/28* (2013.01); *C07C 321/30* (2013.01); *C07C 323/62* (2013.01); *C07D 213/81* (2013.01); *C07D 213/82* (2013.01)

(58) Field of Classification Search
CPC .... C07D 213/81; C07D 213/82; A01N 43/40; A01N 43/54; A01N 43/60; A01N 43/66; A01N 43/707; A01N 37/46; A01N 41/10; A01N 47/02; C07C 317/44; C07C 317/46; C07C 321/28; C07C 321/30; C07C 323/62
See application file for complete search history.

(56) References Cited

U.S. PATENT DOCUMENTS

| 4,235,925 A | 11/1980 | Kirino et al. |
| 4,347,188 A | 8/1982 | Kirino et al. |

(Continued)

FOREIGN PATENT DOCUMENTS

| JP | 53-86031 A | 7/1978 |
| JP | 53-99324 A | 8/1978 |

(Continued)

OTHER PUBLICATIONS

International Preliminary Report on Patentability for PCT/JP2016/064156 dated Nov. 14, 2017.

(Continued)

*Primary Examiner* — John Pak
(74) *Attorney, Agent, or Firm* — Knobbe, Martens, Olson & Bear, LLP

(57) ABSTRACT

In crop production in the fields of agriculture, horticulture and the like, the damage caused by diseases etc. is still immense, and diseases resistant to existing microbicides have emerged. Under such circumstances, the development of novel agricultural and horticultural microbicides is desired.

The present invention provides an anthranilic acid ester compound represented by the general formula (1):

(1)

(wherein $A^1$, $A^3$ and $A^4$ each represent a CH group, $A^2$ represents a C-haloalkyl group, $R^1$ represents an alkyl group, $R^3$ represents a hydrogen atom or an acyl group, $R^4$, $R^5$ and $R^7$ each represent a hydrogen atom, $R^6$ represents a haloalkyl group, Z represents an alkyl group, and m represents 0, 1 or 2), or
a salt thereof, an agricultural and horticultural microbicide comprising the compound or a salt thereof as an active ingredient, and a method for using the microbicide.

7 Claims, No Drawings

(51) Int. Cl.
*C07C 321/30* (2006.01)
*C07C 323/62* (2006.01)
*C07D 213/81* (2006.01)
*C07D 213/82* (2006.01)

(56) References Cited

U.S. PATENT DOCUMENTS

| | | | |
|---|---|---|---|
| 5,756,524 A | 5/1998 | Riordan et al. | |
| 2009/0133318 A1* | 5/2009 | Lahm | A01N 43/56 43/131 |
| 2016/0366884 A1 | 12/2016 | Yonemura et al. | |

FOREIGN PATENT DOCUMENTS

| | | |
|---|---|---|
| JP | 53-113022 A | 10/1978 |
| JP | 54-2322 A | 1/1979 |
| JP | 09-510471 A | 10/1997 |
| JP | 2003-34671 A | 2/2003 |
| WO | WO 95/25723 A1 | 9/1995 |
| WO | WO 2015/072463 A1 | 5/2015 |
| WO | WO 2015/112081 A1 | 7/2015 |

OTHER PUBLICATIONS

Kirino, Osamu et al., "Fungicidal Activity of N-Benzoylanthranilates and Related Compounds" Agric. Biol. Chem., 1980, pp. 2143-2147, vol. 44, No. 9.

International Search Report for PCT/JP2016/064156 dated Jul. 26, 2016.

Extended European Search Report received in corresponding European Patent Application No. 16792746.6 dated Nov. 13, 2018.

* cited by examiner

ANTHRANILIC ACID ESTER COMPOUND OR SALT THEREOF, AGRICULTURAL AND HORTICULTURAL MICROBICIDE COMPRISING THE COMPOUND, AND METHOD FOR USING THE MICROBICIDE

CROSS REFERENCE TO RELATED APPLICATIONS

This application is a U.S. National Phase Application of PCT International Application Number PCT/JP2016/064156, filed on May 12, 2016, designating the United States of America and published in Japanese, which is an International Application of and claims the benefit of priority to Japanese Patent Application No. 2015-097919, filed on May 13, 2015, and Japanese Patent Application No. 2015-168575, filed on Aug. 28, 2015. The disclosures of the above-referenced applications are hereby expressly incorporated by reference in their entireties.

TECHNICAL FIELD

The present invention relates to an agricultural and horticultural microbicide comprising a novel anthranilic acid ester compound or a salt thereof as an active ingredient, and a method for using the microbicide.

BACKGROUND ART

Various compounds have been examined for their potential as agricultural and horticultural pesticides, and among them, certain kinds of anthranilic acid ester compounds have been reported to be useful as microbicides (for example, see Patent Literature 1 to 5 and Non Patent Literature 1). In addition, certain kinds of anthranilic acid ester compounds are reported in Patent Literature 6 to be useful as insecticides.

CITATION LIST

Patent Literature

Patent Literature 1: JP-A 53-086031
Patent Literature 2: JP-A 53-099324
Patent Literature 3: JP-A 53-113022
Patent Literature 4: JP-A 54-002322
Patent Literature 5: WO 95/25723
Patent Literature 6: JP-A 2003-034671

Non Patent Literature

Non Patent Literature 1:
Agricultural and Biological Chemistry, 44 (9), 2143-2147, 1980

SUMMARY OF INVENTION

Technical Problem

In crop production in the fields of agriculture, horticulture and the like, the damage caused by diseases is still immense, and diseases resistant to existing microbicides have emerged. Under such circumstances, the development of novel agricultural and horticultural microbicides having low environmental toxicity is desired.

Means for Solving the Problem

The present inventors conducted extensive examination to solve the above-described problems. As a result, the present inventors found that an anthranilic acid ester compound represented by the general formula (1) or a salt thereof is less environmentally toxic and highly effective for the control of agricultural and horticultural disease-causing microorganisms, and reached the completion of the present invention.

That is, the present invention relates to the following.

[1] An anthranilic acid ester compound represented by the formula:

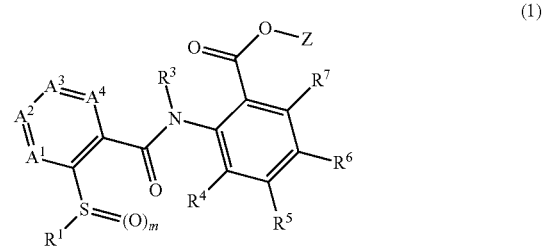

{wherein $R^1$ represents
(a1) a ($C_1$-$C_6$) alkyl group;
(a2) a ($C_2$-$C_6$) alkenyl group;
(a3) a ($C_2$-$C_6$) alkynyl group;
(a4) a ($C_3$-$C_6$) cycloalkyl ($C_1$-$C_6$) alkyl group;
(a5) a phenyl group; or
(a6) a phenyl group having, on the ring, 1 to 5 substituting groups which may be the same or different and are selected from the group consisting of (a) a halogen atom, (b) a cyano group, (c) a nitro group, (d) a ($C_1$-$C_6$) alkyl group, (e) a ($C_1$-$C_6$) alkoxy group, (f) a halo ($C_1$-$C_6$) alkyl group and (g) a halo ($C_1$-$C_6$) alkoxy group,
$R^3$ represents
(b1) a hydrogen atom;
(b2) a ($C_1$-$C_6$) alkyl group;
(b3) a ($C_2$-$C_6$) alkenyl group;
(b4) a ($C_2$-$C_6$) alkynyl group;
(b5) a ($C_3$-$C_6$) cycloalkyl group;
(b6) a halo ($C_1$-$C_6$) alkyl group;
(b7) a ($C_3$-$C_6$) cycloalkyl ($C_1$-$C_6$) alkyl group;
(b8) a ($C_1$-$C_6$) alkoxy ($C_1$-$C_6$) alkyl group;
(b9) a ($C_1$-$C_6$) alkylcarbonyl group;
(b10) a ($C_1$-$C_6$) alkoxycarbonyl group;
(b11) a ($C_3$-$C_6$) cycloalkylcarbonyl group;
(b12) a ($C_1$-$C_6$) alkoxy ($C_1$-$C_6$) alkylcarbonyl group;
(b13) a halo ($C_1$-$C_6$) alkylcarbonyl group;
(b14) a ($C_1$-$C_6$) alkoxycarbonyl ($C_1$-$C_6$) alkyl group; or
(b15) a ($C_1$-$C_6$) alkoxy group,
$R^4$, $R^5$, $R^6$ and $R^7$ may be the same or different, and each represent
(c1) a hydrogen atom;
(c2) a halogen atom;
(c3) a cyano group;
(c4) a nitro group;
(c5) a ($C_1$-$C_6$) alkyl group;
(c6) a halo ($C_1$-$C_6$) alkyl group;
(c7) a ($C_3$-$C_6$) cycloalkyl group;
(c8) a halo ($C_3$-$C_6$) cycloalkyl group;
(c9) a ($C_1$-$C_6$) alkoxy group;
(c10) a halo ($C_1$-$C_6$) alkoxy group;
(c11) a ($C_1$-$C_6$) alkylthio group;
(c12) a ($C_1$-$C_6$) alkylsulfinyl group;
(c13) a ($C_1$-$C_6$) alkylsulfonyl group;
(c14) a halo ($C_1$-$C_6$) alkylthio group;
(c15) a halo ($C_1$-$C_6$) alkylsulfinyl group;
(c16) a halo ($C_1$-$C_6$) alkylsulfonyl group;

(c17) a $(C_1-C_6)$ alkoxy halo $(C_1-C_6)$ alkyl group;
(c18) a phenyl group;
(c19) a phenyl group having, on the ring, 1 to 5 substituting groups which may be the same or different and are selected from the group consisting of (a) a halogen atom, (b) a cyano group, (c) a nitro group, (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group;
(c20) a phenoxy group;
(c21) a phenoxy group having, on the ring, 1 to 5 substituting groups which may be the same or different and are selected from the group consisting of (a) a halogen atom, (b) a cyano group, (c) a nitro group, (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group;
(c22) a pyridyloxy group;
(c23) a pyridyloxy group having, on the ring, 1 to 4 substituting groups which may be the same or different and are selected from the group consisting of (a) a halogen atom, (b) a cyano group, (c) a nitro group, (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group;
(c24) an amino group;
(c25) an amino group having 1 to 2 substituting groups which may be the same or different and are selected from the group consisting of (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group;
(c26) a phenyl $(C_1-C_6)$ alkoxy group; or
(c27) a phenyl $(C_1-C_6)$ alkoxy group having, on the ring, 1 to 5 substituting groups which may be the same or different and are selected from the group consisting of (a) a halogen atom, (b) a cyano group, (c) a nitro group, (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group, except for a case where $R^4$, $R^5$, $R^6$ and $R^7$ each represent a hydrogen atom,
$A^1$, $A^2$, $A^3$ and $A^4$ may be the same or different, and each represent a nitrogen atom or a C—$R^2$ group (wherein $R^2$ represents
(d1) a hydrogen atom;
(d2) a halogen atom;
(d3) a $(C_1-C_6)$ alkyl group;
(d4) a $(C_1-C_6)$ alkoxy group;
(d5) a halo $(C_1-C_6)$ alkyl group;
(d6) a halo $(C_1-C_6)$ alkoxy group;
(d7) a $(C_1-C_6)$ alkylthio group;
(d8) a $(C_1-C_6)$ alkylsulfinyl group;
(d9) a $(C_1-C_6)$ alkylsulfonyl group;
(d10) a halo $(C_1-C_6)$ alkylthio group;
(d11) a halo $(C_1-C_6)$ alkylsulfinyl group;
(d12) a halo $(C_1-C_6)$ alkylsulfonyl group;
(d13) a cyclo $(C_3-C_6)$ alkyl group;
(d14) a phenyl group;
(d15) a phenyl group having, on the ring, 1 to 5 substituting groups which may be the same or different and are selected from the group consisting of (a) a halogen atom, (b) a cyano group, (c) a nitro group, (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group; or
(d16) a phenoxy group),
Z represents
(e1) a $(C_1-C_6)$ alkyl group;
(e2) a $(C_2-C_6)$ alkenyl group;
(e3) a $(C_3-C_6)$ alkynyl group;
(e4) a $(C_3-C_6)$ cycloalkyl group;
(e5) a cyclo $(C_3-C_6)$ alkyl $(C_1-C_6)$ alkyl group;
(e6) a phenyl $(C_1-C_6)$ alkyl group; or
(e7) a cyano $(C_1-C_6)$ alkyl group, and
m represents 0, 1 or 2}, and
a salt thereof.

[2] The anthranilic acid ester compound and the salt according to the above [1], wherein
$R^1$ represents
(a1) a $(C_1-C_6)$ alkyl group;
(a2) a $(C_2-C_6)$ alkenyl group; or
(a6) a phenyl group having, on the ring, 1 to 5 substituting groups which may be the same or different and are selected from the group consisting of (a) a halogen atom, (b) a cyano group, (c) a nitro group, (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group,
$R^3$ represents
(b1) a hydrogen atom;
(b2) a $(C_1-C_6)$ alkyl group;
(b3) a $(C_2-C_6)$ alkenyl group;
(b4) a $(C_2-C_6)$ alkynyl group;
(b8) a $(C_1-C_6)$ alkoxy $(C_1-C_6)$ alkyl group;
(b9) a $(C_1-C_6)$ alkylcarbonyl group;
(b10) a $(C_1-C_6)$ alkoxycarbonyl group;
(b11) a $(C_3-C_6)$ cycloalkylcarbonyl group;
(b12) a $(C_1-C_6)$ alkoxy $(C_1-C_6)$ alkylcarbonyl group;
(b13) a halo $(C_1-C_6)$ alkylcarbonyl group;
(b14) a $(C_1-C_6)$ alkoxycarbonyl $(C_1-C_6)$ alkyl group; or
(b15) a $(C_1-C_6)$ alkoxy group,
$R^4$, $R^5$, $R^6$ and $R^7$ may be the same or different, and each represent
(c1) a hydrogen atom;
(c2) a halogen atom;
(c3) a cyano group;
(c4) a nitro group;
(c5) a $(C_1-C_6)$ alkyl group;
(c6) a halo $(C_1-C_6)$ alkyl group;
(c7) a $(C_3-C_6)$ cycloalkyl group;
(c9) a $(C_1-C_6)$ alkoxy group;
(c10) a halo $(C_1-C_6)$ alkoxy group;
(c11) a $(C_1-C_6)$ alkylthio group;
(c12) a $(C_1-C_6)$ alkylsulfinyl group;
(c13) a $(C_1-C_6)$ alkylsulfonyl group;
(c14) a halo $(C_1-C_6)$ alkylthio group;
(c15) a halo $(C_1-C_6)$ alkylsulfinyl group;
(c16) a halo $(C_1-C_6)$ alkylsulfonyl group;
(c17) a $(C_1-C_6)$ alkoxy halo $(C_1-C_6)$ alkyl group;
(c18) a phenyl group;
(c19) a phenyl group having, on the ring, 1 to 5 substituting groups which may be the same or different and are selected from the group consisting of (a) a halogen atom, (b) a cyano group, (c) a nitro group, (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group;
(c21) a phenoxy group having, on the ring, 1 to 5 substituting groups which may be the same or different and are selected from the group consisting of (a) a halogen atom, (b) a cyano group, (c) a nitro group, (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group;
(c23) a pyridyloxy group having, on the ring, 1 to 4 substituting groups which may be the same or different and are selected from the group consisting of (a) a halogen atom, (b) a cyano group, (c) a nitro group, (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group;
(c25) an amino group having 1 to 2 substituting groups which may be the same or different and are selected from the group consisting of (d) a ($C_1$-$C_6$) alkyl group, (e) a ($C_1$-$C_6$) alkoxy group, (f) a halo ($C_1$-$C_6$) alkyl group and (g) a halo ($C_1$-$C_6$) alkoxy group; or (c27) a phenyl ($C_1$-$C_6$) alkoxy group having, on the ring, 1 to 5 substituting groups which may be the same or different and are selected from the group consisting of (a) a halogen atom, (b) a cyano group, (c) a nitro group, (d) a ($C_1$-$C_6$) alkyl group, (e) a ($C_1$-$C_6$) alkoxy group, (f) a halo ($C_1$-$C_6$) alkyl group and (g) a halo ($C_1$-$C_6$) alkoxy group, except for a case where $R^4$, $R^5$, $R^6$ and $R^7$ each represent a hydrogen atom, $A^1$, $A^2$, $A^3$ and $A^4$ may be the same or different, and each represent a nitrogen atom or a C—$R^2$ group (wherein $R^2$ represents (d1) a hydrogen atom;
(d2) a halogen atom;
(d3) a ($C_1$-$C_6$) alkyl group;
(d4) a ($C_1$-$C_6$) alkoxy group;
(d5) a halo ($C_1$-$C_6$) alkyl group;
(d6) a halo ($C_1$-$C_6$) alkoxy group;
(d7) a ($C_1$-$C_6$) alkylthio group;
(d8) a ($C_1$-$C_6$) alkylsulfinyl group;
(d9) a ($C_1$-$C_6$) alkylsulfonyl group;
(d13) a cyclo ($C_3$-$C_6$) alkyl group;
(d14) a phenyl group;
(d15) a phenyl group having, on the ring, 1 to 5 substituting groups which may be the same or different and are selected from the group consisting of (a) a halogen atom, (b) a cyano group, (c) a nitro group, (d) a ($C_1$-$C_6$) alkyl group, (e) a ($C_1$-$C_6$) alkoxy group, (f) a halo ($C_1$-$C_6$) alkyl group and (g) a halo ($C_1$-$C_6$) alkoxy group; or
(d16) a phenoxy group), and Z represents
(e1) a ($C_1$-$C_6$) alkyl group;
(e2) a ($C_2$-$C_6$) alkenyl group;
(e3) a ($C_3$-$C_6$) alkynyl group;
(e6) a phenyl ($C_1$-$C_6$) alkyl group; or
(e7) a cyano ($C_1$-$C_6$) alkyl group.

[3] The anthranilic acid ester compound and the salt according to the above [1] or [2], wherein
$R^3$ represents
(b1) a hydrogen atom;
(b2) a ($C_1$-$C_6$) alkyl group;
(b3) a ($C_2$-$C_6$) alkenyl group;
(b4) a ($C_2$-$C_6$) alkynyl group;
(b8) a ($C_1$-$C_6$) alkoxy ($C_1$-$C_6$) alkyl group;
(b9) a ($C_1$-$C_6$) alkylcarbonyl group;
(b10) a ($C_1$-$C_6$) alkoxycarbonyl group;
(b11) a ($C_3$-$C_6$) cycloalkylcarbonyl group; or
(b14) a ($C_1$-$C_6$) alkoxycarbonyl ($C_1$-$C_6$) alkyl group, $R^4$, $R^5$, $R^6$ and $R^7$ may be the same or different, and each represent
(c1) a hydrogen atom;
(c2) a halogen atom;
(c6) a halo ($C_1$-$C_6$) alkyl group;
(c10) a halo ($C_1$-$C_6$) alkoxy group;
(c17) a ($C_1$-$C_6$) alkoxy halo ($C_1$-$C_6$) alkyl group;
(c18) a phenyl group;
(c19) a phenyl group having, on the ring, 1 to 5 substituting groups which may be the same or different and are selected from the group consisting of (a) a halogen atom, (b) a cyano group, (c) a nitro group, (d) a ($C_1$-$C_6$) alkyl group, (e) a ($C_1$-$C_6$) alkoxy group, (f) a halo ($C_1$-$C_6$) alkyl group and (g) a halo ($C_1$-$C_6$) alkoxy group;
(c21) a phenoxy group having, on the ring, 1 to 5 substituting groups which may be the same or different and are selected from the group consisting of (a) a halogen atom, (b) a cyano group, (c) a nitro group, (d) a ($C_1$-$C_6$) alkyl group, (e) a ($C_1$-$C_6$) alkoxy group, (f) a halo ($C_1$-$C_6$) alkyl group and (g) a halo ($C_1$-$C_6$) alkoxy group;
(c23) a pyridyloxy group having, on the ring, 1 to 4 substituting groups which may be the same or different and are selected from the group consisting of (a) a halogen atom, (b) a cyano group, (c) a nitro group, (d) a ($C_1$-$C_6$) alkyl group, (e) a ($C_1$-$C_6$) alkoxy group, (f) a halo ($C_1$-$C_6$) alkyl group and (g) a halo ($C_1$-$C_6$) alkoxy group;
(c25) an amino group having 1 to 2 substituting groups which may be the same or different and are selected from the group consisting of (d) a ($C_1$-$C_6$) alkyl group, (e) a ($C_1$-$C_6$) alkoxy group, (f) a halo ($C_1$-$C_6$) alkyl group and (g) a halo ($C_1$-$C_6$) alkoxy group; or
(c27) a phenyl ($C_1$-$C_6$) alkoxy group having, on the ring, 1 to 5 substituting groups which may be the same or different and are selected from the group consisting of (a) a halogen atom, (b) a cyano group, (c) a nitro group, (d) a ($C_1$-$C_6$) alkyl group, (e) a ($C_1$-$C_6$) alkoxy group, (f) a halo ($C_1$-$C_6$) alkyl group and (g) a halo ($C_1$-$C_6$) alkoxy group, except for a case where $R^4$, $R^5$, $R^6$ and $R^7$ each represent a hydrogen atom, and $A^1$, $A^2$, $A^3$ and $A^4$ may be the same or different, and each represent a nitrogen atom or a C—$R^2$ group (wherein $R^2$ represents
(d1) a hydrogen atom;
(d2) a halogen atom;
(d5) a halo ($C_1$-$C_6$) alkyl group;
(d6) a halo ($C_1$-$C_6$) alkoxy group;
(d13) a cyclo ($C_3$-$C_6$) alkyl group;
(d14) a phenyl group; or
(d15) a phenyl group having, on the ring, 1 to 5 substituting groups which may be the same or different and are selected from the group consisting of (a) a halogen atom, (b) a cyano group, (c) a nitro group, (d) a ($C_1$-$C_6$) alkyl group, (e) a ($C_1$-$C_6$) alkoxy group, (f) a halo ($C_1$-$C_6$) alkyl group and (g) a halo ($C_1$-$C_6$) alkoxy group).

[4] Use of the anthranilic acid ester compound or the salt according to any of the above [1] to [3] as an agricultural and horticultural microbicide.

[5] A method for using an agricultural and horticultural microbicide, the method comprising treating plants or soil with an active ingredient of the agricultural and horticultural microbicide specified in the above [4].

[6] A method for controlling an agricultural and horticultural disease, the method comprising treating plants or soil with an effective amount of the agricultural and horticultural microbicide specified in the above [5].

[7] The method according to the above [6], wherein the agricultural and horticultural disease is powdery mildew.

Advantageous Effects of Invention

The anthranilic acid ester of the present invention or a salt thereof is highly effective as an agricultural and horticultural microbicide.

DESCRIPTION OF EMBODIMENTS

In the definitions of the general formula (1) representing the anthranilic acid ester compound of the present invention or a salt thereof, "halo" refers to a "halogen atom" and represents a chlorine atom, a bromine atom, an iodine atom or a fluorine atom.

The "($C_1$-$C_6$) alkyl group" refers to a straight-chain or branched-chain alkyl group of 1 to 6 carbon atoms, for example, a methyl group, an ethyl group, a n-propyl group, an isopropyl group, a n-butyl group, an isobutyl group, a sec-butyl group, a tert-butyl group, a n-pentyl group, an isopentyl group, a tert-pentyl group, a neopentyl group, a 2,3-dimethylpropyl group, an 1-ethylpropyl group, a 1-methylbutyl group, a 2-methylbutyl group, a n-hexyl group, an isohexyl group, a 2-hexyl group, a 3-hexyl group, a 2-methylpentyl group, a 3-methylpentyl group, a 1,1,2-trimethyl propyl group, a 3,3-dimethylbutyl group or the like. The "($C_2$-$C_6$) alkenyl group" refers to a straight-chain or branched-chain alkenyl group of 2 to 6 carbon atoms, for example, a vinyl group, an allyl group, an isopropenyl group, a 1-butenyl group, a 2-butenyl group, a 2-methyl-2-propenyl group, a 1-methyl-2-propenyl group, a 2-methyl-1-propenyl group, a pentenyl group, a 1-hexenyl group, a 3,3-dimethyl-1-butenyl group or the like. The "($C_2$-$C_6$) alkynyl group" refers to a straight-chain or branched-chain alkynyl group of 2 to 6 carbon atoms, for example, an ethynyl group, a 1-propynyl group, a 2-propynyl group, a 1-butynyl group, a 2-butynyl group, a 3-butynyl group, a 3-methyl-1-propynyl group, a 2-methyl-3-propynyl group, a pentynyl group, a 1-hexynyl group, a 3-methyl-1-butynyl group, a 3,3-dimethyl-1-butynyl group or the like.

The "($C_3$-$C_6$) cycloalkyl group" refers to a cyclic alkyl group of 3 to 6 carbon atoms, for example, a cyclopropyl group, a cyclobutyl group, a cyclopentyl group, a cyclohexyl group or the like. The "($C_1$-$C_6$) alkoxy group" refers to a straight-chain or branched-chain alkoxy group of 1 to 6 carbon atoms, for example, a methoxy group, an ethoxy group, a n-propoxy group, an isopropoxy group, a n-butoxy group, a sec-butoxy group, a tert-butoxy group, a n-pentyloxy group, an isopentyloxy group, a tert-pentyloxy group, a neopentyloxy group, a 2,3-dimethylpropyloxy group, an 1-ethylpropyloxy group, a 1-methylbutyloxy group, a n-hexyloxy group, an isohexyloxy group, a 1,1,2-trimethylpropyloxy group or the like.

The "($C_1$-$C_6$) alkylthio group" refers to a straight-chain or branched-chain alkylthio group of 1 to 6 carbon atoms, for example, a methylthio group, an ethylthio group, a n-propylthio group, an isopropylthio group, a n-butylthio group, a sec-butylthio group, a tert-butylthio group, a n-pentylthio group, an isopentylthio group, a tert-pentylthio group, a neopentylthio group, a 2,3-dimethylpropylthio group, an 1-ethylpropylthio group, a 1-methylbutylthio group, a n-hexylthio group, an isohexylthio group, a 1,1,2-trimethylpropylthio group or the like. The "($C_1$-$C_6$) alkylsulfinyl group" refers to a straight-chain or branched-chain alkylsulfinyl group of 1 to 6 carbon atoms, for example, a methylsulfinyl group, an ethylsulfinyl group, a n-propylsulfinyl group, an isopropylsulfinyl group, a n-butylsulfinyl group, a sec-butylsulfinyl group, a tert-butylsulfinyl group, a n-pentylsulfinyl group, an isopentylsulfinyl group, a tert-pentylsulfinyl group, a neopentylsulfinyl group, a 2,3-dimethylpropylsulfinyl group, an 1-ethylpropylsulfinyl group, a 1-methylbutylsulfinyl group, a n-hexylsulfinyl group, an isohexylsulfinyl group, a 1,1,2-trimethylpropylsulfinyl group or the like. The "($C_1$-$C_6$) alkylsulfonyl group" refers to a straight-chain or branched-chain alkylsulfonyl group of 1 to 6 carbon atoms, for example, a methylsulfonyl group, an ethylsulfonyl group, a n-propylsulfonyl group, an isopropylsulfonyl group, a n-butylsulfonyl group, a sec-butylsulfonyl group, a tert-butylsulfonyl group, a n-pentylsulfonyl group, an isopentylsulfonyl group, a tert-pentylsulfonyl group, a neopentylsulfonyl group, a 2,3-dimethylpropylsulfonyl group, an 1-ethylpropylsulfonyl group, a 1-methylbutylsulfonyl group, a n-hexylsulfonyl group, an isohexylsulfonyl group, a 1,1,2-trimethylpropylsulfonyl group or the like.

The above-mentioned "($C_1$-$C_6$) alkyl group", "($C_2$-$C_6$) alkenyl group", "($C_2$-$C_6$) alkynyl group", "($C_3$-$C_6$) cycloalkyl group", "($C_1$-$C_6$) alkoxy group", "($C_1$-$C_6$) alkylthio group", "($C_1$-$C_6$) alkylsulfinyl group" or "($C_1$-$C_6$) alkylsulfonyl group" may be substituted with one or more halogen atoms at a substitutable position(s), and in the case where the above-listed group is substituted by two or more halogen atoms, the halogen atoms may be the same or different.

The above-mentioned "substituting group substituted with one or more halogen atoms at a substitutable position(s)" is expressed as a "halo ($C_1$-$C_6$) alkyl group", a "halo ($C_2$-$C_6$) alkenyl group", a "halo ($C_2$-$C_6$) alkynyl group", a "halo ($C_3$-$C_6$) cycloalkyl group", a "halo ($C_1$-$C_6$) alkoxy group", a "halo ($C_1$-$C_6$) alkylthio group", a "halo ($C_1$-$C_6$) alkylsulfinyl group" or a "halo ($C_1$-$C_6$) alkylsulfonyl group".

The expressions "($C_1$-$C_6$)", "($C_2$-$C_6$)", "($C_3$-$C_6$)", etc. each refer to the range of the number of carbon atoms in the substituting groups. The same definition holds true for the groups coupled to the above-mentioned substituting groups, and for example, the "($C_1$-$C_6$) alkoxy halo ($C_1$-$C_6$) alkyl group" means that a straight-chain or branched-chain alkoxy group of 1 to 6 carbon atoms is bound to a straight-chain or branched-chain haloalkyl group of 1 to 6 carbon atoms.

Examples of the salt of the anthranilic acid ester represented by the general formula (1) of the present invention include inorganic acid salts, such as hydrochlorides, sulfates, nitrates and phosphates; organic acid salts, such as acetates, fumarates, maleates, oxalates, methanesulfonates, benzenesulfonates and p-toluenesulfonates; and salts with an inorganic or organic base such as a sodium ion, a potassium ion, a calcium ion and a trimethylammonium ion.

The anthranilic acid ester compound represented by the general formula (1) of the present invention and a salt thereof can have one or more chiral centers in the structural formula, and can exist as two or more kinds of optical isomers or diastereomers. All the optical isomers and mixtures of the isomers at any ratio are also included in the present invention. Further, the compound represented by the general formula (1) of the present invention and a salt thereof can exist as two kinds of geometric isomers due to a carbon-carbon double bond in the structural formula. All the geometric isomers and mixtures of the isomers at any ratio are also included in the present invention.

In preferable embodiments, the anthranilic acid ester compound represented by the general formula (1) of the present invention or a salt thereof is the one in which $R^1$ is (a1) a ($C_1$-$C_6$) alkyl group, $R^3$ is (b1) a hydrogen atom;

(b2) a ($C_1$-$C_6$) alkyl group;

(b8) a ($C_1$-$C_6$) alkoxy ($C_1$-$C_6$) alkyl group;

(b9) a ($C_1$-$C_6$) alkylcarbonyl group; or (b10) a ($C_1$-$C_6$) alkoxycarbonyl group, $R^4$, $R^5$, $R^6$ and $R^2$ may be the same or different, and are each (c1) a hydrogen atom;

(c2) a halogen atom;

(c6) a halo ($C_1$-$C_6$) alkyl group; or (c10) a halo ($C_1$-$C_6$) alkoxy group, except for a case where $R^4$, $R^5$, $R^6$ and $R^2$ each represent a hydrogen atom, $A^1$, $A^2$, $A^3$ and $A^4$ may be the same or different, and are each a nitrogen atom or a C—$R^2$ group (wherein $R^2$ represents (d2) a halogen atom; or (d5) a halo ($C_1$-$C_6$) alkyl group), Z is (e2) a ($C_1$-$C_6$) alkyl group, and m is 0, 1 or 2.

The anthranilic acid ester compound represented by the general formula (1) or a salt thereof can be produced according to, for example, the production methods described below, but the present invention is not limited thereto.

Production Method 1

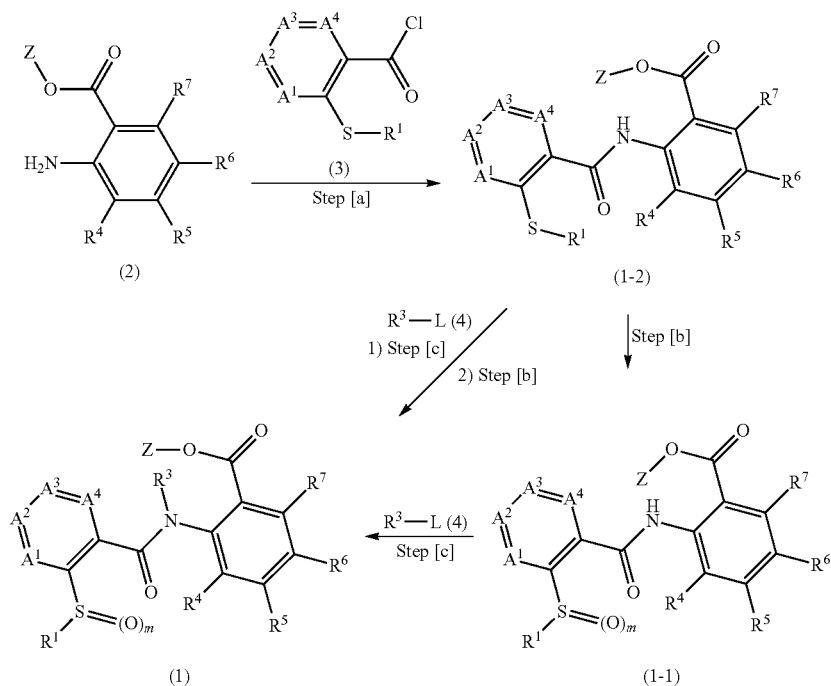

(In the formulae, $R^1$, $R^3$, $R^4$, $R^5$, $R^6$, $R^7$, $A^1$, $A^2$, $A^3$, $A^4$, Z and m are as defined above, and L represents a leaving group.)

Production Method at Step [a]

The anthranilic acid ester compound represented by the general formula (1-2) can be produced by allowing the carboxylic chloride represented by the general formula (3) to react with the amine compound represented by the general formula (2) in the presence of a base and an inert solvent. Since this reaction is an equimolar reaction of the reactants, they are basically used in equimolar amounts, but either of them may be used in an excess amount.

The base used in this reaction may be an inorganic base or an organic base. Examples of the inorganic base include alkali metal hydroxides such as sodium hydroxide and potassium hydroxide; and carbonates such as sodium carbonate, potassium carbonate and sodium hydrogen carbonates. Examples of the organic base include triethylamine, pyridine and DBU. The amount of the base used is selected from the range of a catalytic amount to an excess molar amount relative to the carboxylic chloride represented by the general formula (3).

The inert solvent used in this reaction may be any solvent unless it markedly inhibits the progress of the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, dioxane and tetrahydrofuran; esters such as ethyl acetate; amides such as dimethylformamide and dimethylacetamide; and others such as dimethyl sulfoxide, 1,3-dimethyl-2-imidazolidinone, acetone and methyl ethyl ketone. These inert solvents may be used alone or as a mixture of two or more kinds.

This reaction may be conducted under the atmosphere of an inert gas such as nitrogen gas and argon gas. The reaction temperature is in the range of room temperature to the boiling point of the inert solvent used. The reaction time varies with the reaction scale and the reaction temperature, but is basically in the range of a few minutes to 48 hours. After the reaction is completed, the compound of interest is isolated from the post-reaction mixture by a usual method. As needed, the compound of interest can be purified by recrystallization, column chromatography, etc. Alternatively, the isolated product may be subjected to the next step without purification.

Production Method at Step [b]

The anthranilic acid ester compound represented by the general formula (1-1) can be produced by allowing the anthranilic acid ester compound represented by the general formula (1-2) to react with an oxidizing agent in an inert solvent. Examples of the oxidizing agent used in this reaction include peroxides such as a hydrogen peroxide solution, perbenzoic acid and m-chloroperoxybenzoic acid. The amount of the oxidizing agent used is appropriately selected from the range of 0.8- to 5-fold molar equivalents relative to the anthranilic acid ester compound represented by the general formula (1-1), and is preferably in the range of 1- to 2-fold molar equivalents.

The inert solvent used in this reaction may be any solvent unless it markedly inhibits the reaction, and the examples include straight-chain or cyclic ethers such as diethyl ether, tetrahydrofuran and dioxane; aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; organic acids such as formic acid and acetic acid; and polar solvents such as N,N-dimethylformamide, N,N-dimethylacetamide, 1,3-dimethyl-2-imidazolidinone and water. These solvents may be used alone or as a mixture of two or more kinds.

The reaction temperature in this reaction is appropriately selected from the range of −10° C. to the reflux temperature of the inert solvent used. The reaction time varies with the reaction scale, the reaction temperature and the like and is not the same in every case, but is basically selected as appropriate from the range of a few minutes to 48 hours. After the reaction is completed, the compound of interest is isolated from the post-reaction mixture by a usual method. As needed, the compound of interest can be purified by recrystallization, column chromatography, etc.

Production Method at Step [c]

The compound represented by the general formula (1) can be produced by allowing the anthranilic acid ester compound represented by the general formula (1-1) to react with the compound represented by the general formula (4) in the presence of a base and an inert solvent. In the general formula (4), $R^3$ is as defined above. In the general formula (4), L represents a leaving group such as chlorine and bromine.

Examples of the base used in this reaction include inorganic bases such as sodium hydroxide, potassium hydroxide, sodium carbonate, potassium carbonate, cesium carbonate, sodium hydrogen carbonate and potassium hydrogen carbonate; alkali metal hydrides such as sodium hydride and potassium hydride; alkali metal alkoxides such as sodium methoxide, sodium ethoxide and potassium tert-butoxide; alkyllithiums such as methyllithium and n-butyllithium; and organic bases such as triethylamine, pyridine and diazabicycloundecen (DBU).

The amount of the base used is an equimolar or excess molar amount relative to the anthranilic acid ester compound represented by the general formula (1-1).

Since this reaction is an equimolar reaction of the reactants, they are basically used in equimolar amounts, but either of them may be used in an excess amount.

The inert solvent used in this reaction may be any solvent unless it markedly inhibits the reaction, and the examples include straight-chain or cyclic ethers such as diethyl ether, tetrahydrofuran and dioxane; aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; organic acids such as formic acid and acetic acid; and polar solvents such as N,N-dimethylformamide, N,N-dimethylacetamide and 1,3-dimethyl-2-imidazolidinone. These solvents may be used alone or as a mixture of two or more kinds.

This reaction may be conducted under the atmosphere of an inert gas such as nitrogen gas and argon gas. The reaction temperature is in the range of room temperature to the boiling point of the inert solvent used. The reaction time varies with the reaction scale and the reaction temperature, but is basically in the range of a few minutes to 48 hours. After the reaction is completed, the compound of interest is isolated from the post-reaction mixture by a usual method.

As needed, the compound of interest can be purified by recrystallization, column chromatography, etc.

Alternatively, the compound represented by the general formula (1) can be produced through the steps [c] and [b] in this order from the anthranilic acid ester compound represented by the general formula (1-2).

Production Method 2

This production method shows that the compound of the present invention can be produced from the corresponding nitro compound as well.

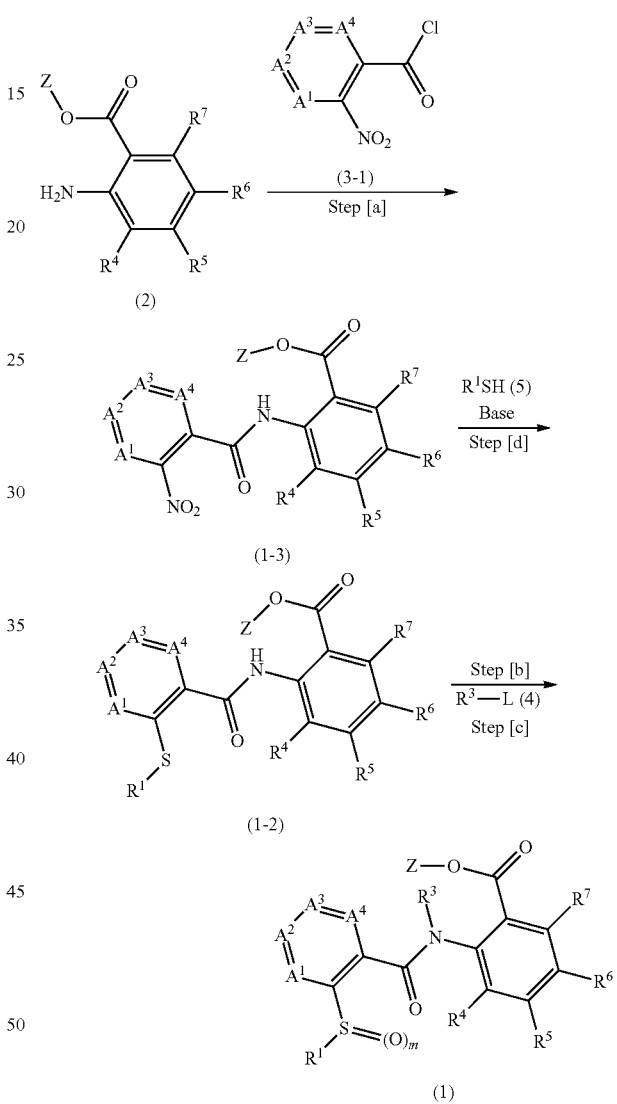

(In the formulae, $R^1$, $R^3$, $R^4$, $R^5$, $R^6$, $R^7$, $A^1$, $A^2$, $A^3$, $A^4$, Z and m are as defined above, and L represents a leaving group.)

Production Method at Step [a]

This reaction produces the anthranilic acid ester compound represented by the general formula (1-3) similarly as in the above Production Method 1 except for using the carboxylic chloride represented by the general formula (3-1) instead of the carboxylic chloride represented by the general formula (3).

Production Method at Step [d]

The anthranilic acid ester compound represented by the general formula (1-2) can be produced by allowing the anthranilic acid ester compound represented by the general formula (1-3) to react with the thiol compound represented by the general formula (5) in the presence of a base in an inert solvent.

Examples of the base that can be used in this reaction include inorganic bases such as sodium hydroxide, potassium hydroxide, sodium carbonate, potassium carbonate, cesium carbonate, sodium hydrogen carbonate and potassium hydrogen carbonate; alkali metal hydrides such as sodium hydride and potassium hydride; and alkoxides such as sodium methoxide, sodium ethoxide and potassium tert-butoxide. The amount of the base used is usually in the range of about 1- to 5-fold molar amounts relative to the compound represented by the general formula (1-3). Commercially available products of sodium methanethiolate or sodium ethanethiolate can also be used as the base, and in this case, compound (5) does not have to be used.

The solvent used in this reaction may be any solvent unless it markedly inhibits the reaction, and the examples include alcohols such as methanol, ethanol, propanol, butanol and 2-propanol; straight-chain or cyclic ethers such as diethyl ether, tetrahydrofuran and dioxane; aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; and polar solvents such as N,N-dimethylformamide, N,N-dimethylacetamide, dimethyl sulfoxide and 1,3-dimethyl-2-imidazolidinone. These solvents may be used alone or as a mixture of two or more kinds.

The reaction temperature in this reaction is usually in the range of about 0° C. to the boiling point of the solvent used. The reaction time varies with the reaction scale, the reaction temperature and the like, but is basically selected as appropriate from the range of a few minutes to 48 hours. The compound represented by the general formula (5) is usually used in an about 1- to 5-fold molar amount relative to the anthranilic acid ester compound represented by the general formula (1-3). This reaction may be conducted under the atmosphere of an inert gas such as nitrogen gas and argon gas. After the reaction is completed, the compound of interest is isolated from the post-reaction mixture by usual methods such as phase transfer, concentration and crystallization. As needed, the compound of interest can be purified by recrystallization, column chromatography, etc.

Production Method at Steps [b] and [c]

These reactions can be conducted similarly as described in Production Method 1 to give the anthranilic acid ester compound represented by the general formula (1).

Alternatively, the compound represented by the general formula (1) may be produced through the steps [c] and [b] in this order from the anthranilic acid ester compound represented by the general formula (1-2).

Next, specific examples of the compound of the present invention are shown below. In the following tables, Me stands for a methyl group, Et stands for an ethyl group, n-Pr stands for a n-propyl group, i-Pr stands for an isopropyl group, c-Pr stands for a cyclopropyl group, n-Bu stands for a n-butyl group, i-Bu stands for an isobutyl group, s-Bu stands for a sec-butyl group, t-Bu stands for a tert-butyl group, c-Pen stands for a cyclopentyl group, c-Hex stands for a cyclohexyl group, Ph stands for a phenyl group, Bn stands for a benzyl group, Ac stands for an acetyl group, allyl stands for an allyl group, and propargyl stands for a propargyl group. The physical property refers to a melting point (° C.) and a refractive index (measurement temperature; ° C.).

Table 11 shows $^1$H-NMR data (400 MHz, CDCl$_3$) of the compounds listed with "NMR" in the columns of "Physical property" of Tables 1-1 to 10-2

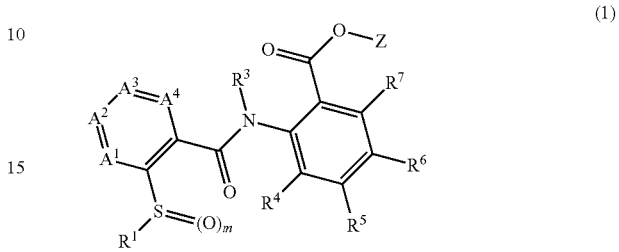

(1)

TABLE 1-1

| Compound No. | $R^1$ | $A^2$ | $R^3$ | $R^6$ | Z | m | Physical property |
|---|---|---|---|---|---|---|---|
| 1-1 | Et | C—CF$_3$ | H | CF(CF$_3$)$_2$ | Me | 0 | 84-85 |
| 1-2 | Et | C—CF$_3$ | H | CF(CF$_3$)$_2$ | Me | 1 | 150-152 |
| 1-3 | Et | C—CF$_3$ | H | CF(CF$_3$)$_2$ | Me | 2 | 182-183 |
| 1-4 | Et | C—CF$_3$ | Me | CF(CF$_3$)$_2$ | Me | 0 | |
| 1-5 | Et | C—CF$_3$ | Me | CF(CF$_3$)$_2$ | Me | 1 | |
| 1-6 | Et | C—CF$_3$ | Me | CF(CF$_3$)$_2$ | Me | 2 | |
| 1-7 | Et | C—CF$_3$ | Ac | CF(CF$_3$)$_2$ | Me | 0 | 1.4850 (20.5° C.) |
| 1-8 | Et | C—CF$_3$ | Ac | CF(CF$_3$)$_2$ | Me | 1 | 1.4690 (27.2° C.) |
| 1-9 | Et | C—CF$_3$ | Ac | CF(CF$_3$)$_2$ | Me | 2 | 150-151 |
| 1-10 | Et | C—CF$_3$ | COEt | CF(CF$_3$)$_2$ | Me | 0 | |
| 1-11 | Et | C—CF$_3$ | COEt | CF(CF$_3$)$_2$ | Me | 1 | |
| 1-12 | Et | C—CF$_3$ | COEt | CF(CF$_3$)$_2$ | Me | 2 | 69-70 |
| 1-13 | Et | C—CF$_3$ | CO—n-Pr | CF(CF$_3$)$_2$ | Me | 0 | |
| 1-14 | Et | C—CF$_3$ | CO—n-Pr | CF(CF$_3$)$_2$ | Me | 1 | |
| 1-15 | Et | C—CF$_3$ | CO—n-Pr | CF(CF$_3$)$_2$ | Me | 2 | |
| 1-16 | Et | C—CF$_3$ | CO—i-Pr | CF(CF$_3$)$_2$ | Me | 0 | |
| 1-17 | Et | C—CF$_3$ | CO—i-Pr | CF(CF$_3$)$_2$ | Me | 1 | |
| 1-18 | Et | C—CF$_3$ | CO—i-Pr | CF(CF$_3$)$_2$ | Me | 2 | 69-70 |
| 1-19 | Et | C—CF$_3$ | COOMe | CF(CF$_3$)$_2$ | Me | 0 | |
| 1-20 | Et | C—CF$_3$ | COOMe | CF(CF$_3$)$_2$ | Me | 1 | |
| 1-21 | Et | C—CF$_3$ | COOMe | CF(CF$_3$)$_2$ | Me | 2 | 64-65 |
| 1-22 | Et | C—CF$_3$ | COOEt | CF(CF$_3$)$_2$ | Me | 0 | |
| 1-23 | Et | C—CF$_3$ | COOEt | CF(CF$_3$)$_2$ | Me | 1 | |
| 1-24 | Et | C—CF$_3$ | COOEt | CF(CF$_3$)$_2$ | Me | 2 | 59-60 |
| 1-25 | Et | C—CF$_3$ | CH$_2$OMe | CF(CF$_3$)$_2$ | Me | 0 | 1.3142 (20.2° C.) |

$R^4$, $R^5$ and $R^7$ each represent a hydrogen atom, and $A^1$, $A^3$ and $A^4$ each represent a CH group.

TABLE 1-2

| Compound No. | $R^1$ | $A^2$ | $R^3$ | $R^6$ | Z | m | Physical property |
|---|---|---|---|---|---|---|---|
| 1-26 | Et | C—CF$_3$ | CH$_2$OMe | CF(CF$_3$)$_2$ | Me | 1 | |
| 1-27 | Et | C—CF$_3$ | CH$_2$OMe | CF(CF$_3$)$_2$ | Me | 2 | |
| 1-28 | Et | C—CF$_3$ | CH$_2$OEt | CF(CF$_3$)$_2$ | Me | 0 | |
| 1-29 | Et | C—CF$_3$ | CH$_2$OEt | CF(CF$_3$)$_2$ | Me | 1 | |
| 1-30 | Et | C—CF$_3$ | CH$_2$OEt | CF(CF$_3$)$_2$ | Me | 2 | |
| 1-31 | Et | C—CF$_3$ | H | CF(CF$_3$)$_2$ | Et | 0 | 81-82 |
| 1-32 | Et | C—CF$_3$ | H | CF(CF$_3$)$_2$ | Et | 1 | 1.5053 (18.0° C.) |
| 1-33 | Et | C—CF$_3$ | H | CF(CF$_3$)$_2$ | Et | 2 | 130-131 |
| 1-34 | Et | C—CF$_3$ | H | CF(CF$_3$)$_2$ | n-Pr | 0 | 77-78 |
| 1-35 | Et | C—CF$_3$ | H | CF(CF$_3$)$_2$ | n-Pr | 1 | |

TABLE 1-2-continued

| Compound No. | R¹ | A² | R³ | R⁶ | Z | m | Physical property |
|---|---|---|---|---|---|---|---|
| 1-36 | Et | C—CF₃ | H | CF(CF₃)₂ | i-Pr | 0 | 114-116 |
| 1-37 | Et | C—CF₃ | H | CF(CF₃)₂ | allyl | 0 | 108-109 |
| 1-38 | Et | C—CF₃ | H | CF(CF₃)₂ | allyl | 1 | |
| 1-39 | Et | C—CF₃ | H | CF(CF₃)₂ | allyl | 2 | |
| 1-40 | Et | C—CF₃ | allyl | CF(CF₃)₂ | allyl | 0 | 1.4215 (20.8) |
| 1-41 | Et | C—CF₃ | H | CF(CF₃)₂ | Bn | 0 | 67-69 |
| 1-42 | Et | C—CF₃ | propargyl | CF(CF₃)₂ | propargyl | 0 | 1.3401 (20.8° C.) |
| 1-43 | Et | C—CF₃ | CO—n-Pr | CF(CF₃)₂ | Et | 0 | |
| 1-44 | Et | C—CF₃ | CO—n-Pr | CF(CF₃)₂ | Et | 1 | |
| 1-45 | Et | C—CF₃ | CO—n-Pr | CF(CF₃)₂ | Et | 2 | |
| 1-46 | Et | C—CF₃ | CO—i-Pr | CF(CF₃)₂ | Et | 0 | |
| 1-47 | Et | C—CF₃ | CO—i-Pr | CF(CF₃)₂ | Et | 1 | |
| 1-48 | Et | C—CF₃ | CO—i-Pr | CF(CF₃)₂ | Et | 2 | |
| 1-49 | Et | C—CF₃ | COOMe | CF(CF₃)₂ | Et | 0 | |
| 1-50 | Et | C—CF₃ | COOMe | CF(CF₃)₂ | Et | 1 | |

$R^4$, $R^5$ and $R^7$ each represent a hydrogen atom, and $A^1$, $A^3$ and $A^4$ each represent a CH group.

TABLE 1-3

| Compound No. | R¹ | A² | R³ | R⁶ | Z | m | Physical property |
|---|---|---|---|---|---|---|---|
| 1-51 | Et | C—CF₃ | COOMe | CF(CF₃)₂ | Et | 2 | |
| 1-52 | Et | C—CF₃ | COOEt | CF(CF₃)₂ | Et | 0 | |
| 1-53 | Et | C—CF₃ | COOEt | CF(CF₃)₂ | Et | 1 | |
| 1-54 | Et | C—CF₃ | COOEt | CF(CF₃)₂ | Et | 2 | |
| 1-55 | Et | C—CF₃ | CH₂OMe | CF(CF₃)₂ | Et | 0 | |
| 1-56 | Et | C—CF₃ | CH₂OMe | CF(CF₃)₂ | Et | 1 | |
| 1-57 | Et | C—CF₃ | CH₂OMe | CF(CF₃)₂ | Et | 2 | |
| 1-58 | Et | C—CF₃ | CH₂OEt | CF(CF₃)₂ | Et | 0 | |
| 1-59 | Et | C—CF₃ | CH₂OEt | CF(CF₃)₂ | Et | 1 | |
| 1-60 | Et | C—CF₃ | CH₂OEt | CF(CF₃)₂ | Et | 2 | |
| 1-61 | Et | C—CF₃ | H | Cl | Me | 0 | 165-166 |
| 1-62 | Et | C—CF₃ | H | Cl | Me | 1 | |
| 1-63 | Et | C—CF₃ | H | Cl | Me | 2 | |
| 1-64 | Et | C—CF₃ | H | OCF₃ | Me | 0 | 104-106 |
| 1-65 | Et | C—CF₃ | H | OCF₃ | Me | 1 | |
| 1-66 | Et | C—CF₃ | H | OCF₃ | Me | 2 | 160-161 |
| 1-67 | Et | C—CF₃ | H | I | Me | 0 | 156-157 |

$R^4$, $R^5$ and $R^7$ each represent a hydrogen atom, and $A^1$, $A^3$ and $A^4$ each represent a CH group.

TABLE 1-4

| Compound No. | R¹ | R³ | A¹ | A² | A³ | A⁴ | Z | m | Physical property |
|---|---|---|---|---|---|---|---|---|---|
| 1-68 | Et | H | CH | CF | CH | CH | Me | 0 | 85-86 |
| 1-69 | Et | H | CH | CF | CH | CH | Me | 1 | |
| 1-70 | Et | H | CH | CF | CH | CH | Me | 2 | |
| 1-71 | Et | Ac | CH | CF | CH | CH | Me | 0 | |
| 1-72 | Et | Ac | CH | CF | CH | CH | Me | 1 | |
| 1-73 | Et | Ac | CH | CF | CH | CH | Me | 2 | |
| 1-74 | Et | H | CH | CF | CF | CH | Me | 0 | 107-108 |
| 1-75 | Et | H | CH | CF | CF | CH | Me | 1 | |
| 1-76 | Et | H | CH | CF | CF | CH | Me | 2 | |
| 1-77 | Et | Ac | CH | CF | CF | CH | Me | 0 | 1.3671 (24.1) |
| 1-78 | Et | Ac | CH | CF | CF | CH | Me | 1 | |
| 1-79 | Et | Ac | CH | CF | CF | CH | Me | 2 | |

$R^4$, $R^5$ and $R^7$ each represent a hydrogen atom, and $R^6$ represents $CF(CF_3)_2$.

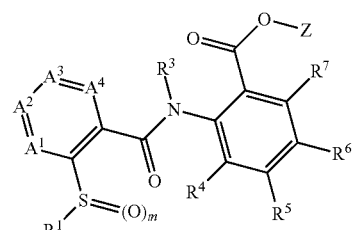

(1)

TABLE 2

| Compound No. | R¹ | A² | R³ | R⁵ | Z | m | Physical property |
|---|---|---|---|---|---|---|---|
| 2-1 | Et | C—CF₃ | H | CF₃ | Me | 0 | 137-138 |
| 2-2 | Et | C—CF₃ | H | CF₃ | Me | 1 | |
| 2-3 | Et | C—CF₃ | H | CF₃ | Me | 2 | |
| 2-4 | Et | C—CF₃ | Ac | CF₃ | Me | 0 | |
| 2-5 | Et | C—CF₃ | Ac | CF₃ | Me | 1 | |
| 2-6 | Et | C—CF₃ | Ac | CF₃ | Me | 2 | |

$R^4$, $R^6$ and $R^7$ each represent a hydrogen atom, and $A^1$, $A^3$ and $A^4$ each represent a CH group.

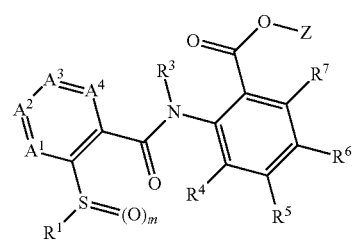

(1)

TABLE 3

| Compound No. | R¹ | A² | A⁴ | R³ | R⁶ | Z | m | Physical property |
|---|---|---|---|---|---|---|---|---|
| 3-1 | Et | C—CF₃ | N | H | CF(CF₃)₂ | Me | 0 | 112-114 |
| 3-2 | Et | C—CF₃ | N | H | CF(CF₃)₂ | Me | 1 | 149-150 |
| 3-3 | Et | C—CF₃ | N | H | CF(CF₃)₂ | Me | 2 | 140-142 |
| 3-4 | Et | C—CF₃ | N | Ac | CF(CF₃)₂ | Me | 0 | |
| 3-5 | Et | C—CF₃ | N | Ac | CF(CF₃)₂ | Me | 1 | 152-154 |
| 3-6 | Et | C—CF₃ | N | Ac | CF(CF₃)₂ | Me | 2 | 150-151 |
| 3-7 | Et | C—CF₃ | N | H | CF(CF₃)₂ | Et | 0 | |
| 3-8 | Et | C—CF₃ | N | H | CF(CF₃)₂ | Et | 1 | |
| 3-9 | Et | C—CF₃ | N | H | CF(CF₃)₂ | Et | 2 | |
| 3-10 | Et | C—CF₃ | N | Ac | CF(CF₃)₂ | Et | 0 | |

TABLE 3-continued

| Compound No. | R¹ | A² | A⁴ | R³ | R⁶ | Z | m | Physical property |
|---|---|---|---|---|---|---|---|---|
| 3-11 | Et | C—CF₃ | N | Ac | CF(CF₃)₂ | Et | 1 | |
| 3-12 | Et | C—CF₃ | N | Ac | CF(CF₃)₂ | Et | 2 | |

$R^4$, $R^5$ and $R^7$ each represent a hydrogen atom, and $A^1$ and $A^3$ each represent a CH group.

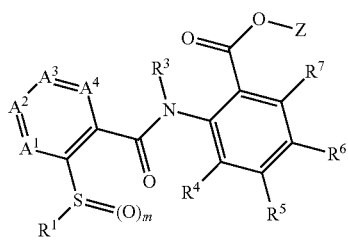

(1)

TABLE 4-1

| Compound No. | R¹ | A² | R³ | R⁶ | Z | m | Physical property |
|---|---|---|---|---|---|---|---|
| 4-1 | Me | C—CF₃ | H | CF(CF₃)₂ | Me | 0 | 162.3-164.1 |
| 4-2 | Me | C—CF₃ | H | CF(CF₃)₂ | Me | 1 | |
| 4-3 | Me | C—CF₃ | H | CF(CF₃)₂ | Me | 2 | |
| 4-4 | Me | C—CF₃ | Ac | CF(CF₃)₂ | Me | 0 | 1.4532 (25.4° C.) |
| 4-5 | Me | C—CF₃ | Ac | CF(CF₃)₂ | Me | 1 | |

TABLE 4-1-continued

| Compound No. | R¹ | A² | R³ | R⁶ | Z | m | Physical property |
|---|---|---|---|---|---|---|---|
| 4-6 | Me | C—CF₃ | Ac | CF(CF₃)₂ | Me | 2 | 164.1-165.1 |
| 4-7 | Me | C—CF₃ | H | CF(CF₃)₂ | Et | 0 | 104.4-104.8 |
| 4-8 | Me | C—CF₃ | H | CF(CF₃)₂ | Et | 1 | |
| 4-9 | Me | C—CF₃ | H | CF(CF₃)₂ | Et | 2 | 144-145 |
| 4-10 | Me | C—CF₃ | Ac | CF(CF₃)₂ | Et | 0 | |
| 4-11 | Me | C—CF₃ | Ac | CF(CF₃)₂ | Et | 1 | |
| 4-12 | Me | C—CF₃ | Ac | CF(CF₃)₂ | Et | 2 | 130-132 |
| 4-13 | n-Pr | C—CF₃ | H | CF(CF₃)₂ | Me | 0 | 144.9-146.1 |
| 4-14 | n-Pr | C—CF₃ | H | CF(CF₃)₂ | Me | 1 | |
| 4-15 | n-Pr | C—CF₃ | H | CF(CF₃)₂ | Me | 2 | |
| 4-16 | n-Pr | C—CF₃ | Ac | CF(CF₃)₂ | Me | 0 | |
| 4-17 | n-Pr | C—CF₃ | Ac | CF(CF₃)₂ | Me | 1 | |
| 4-18 | n-Pr | C—CF₃ | Ac | CF(CF₃)₂ | Me | 2 | 119.5-120.7 |
| 4-19 | n-Pr | C—CF₃ | H | CF(CF₃)₂ | Et | 0 | |
| 4-20 | n-Pr | C—CF₃ | H | CF(CF₃)₂ | Et | 1 | |
| 4-21 | n-Pr | C—CF₃ | H | CF(CF₃)₂ | Et | 2 | |
| 4-22 | n-Pr | C—CF₃ | Ac | CF(CF₃)₂ | Et | 0 | |
| 4-23 | n-Pr | C—CF₃ | Ac | CF(CF₃)₂ | Et | 1 | |
| 4-24 | n-Pr | C—CF₃ | Ac | CF(CF₃)₂ | Et | 2 | |
| 4-25 | i-Pr | C—CF₃ | H | CF(CF₃)₂ | Me | 0 | 145.1-146.2 |

$R^4$, $R^5$ and $R^7$ each represent a hydrogen atom, and $A^1$, $A^3$ and $A^4$ each represent a CH group.

TABLE 4-2

| Compound No. | R¹ | A² | R³ | R⁶ | Z | m | Physical property |
|---|---|---|---|---|---|---|---|
| 4-26 | i-Pr | C—CF₃ | H | CF(CF₃)₂ | Me | 1 | |
| 4-27 | i-Pr | C—CF₃ | H | CF(CF₃)₂ | Me | 2 | |
| 4-28 | i-Pr | C—CF₃ | Ac | CF(CF₃)₂ | Me | 0 | NMR |
| 4-29 | i-Pr | C—CF₃ | Ac | CF(CF₃)₂ | Me | 1 | |
| 4-30 | i-Pr | C—CF₃ | Ac | CF(CF₃)₂ | Me | 2 | 122.1-124.3 |
| 4-31 | i-Pr | C—CF₃ | H | CF(CF₃)₂ | Et | 0 | 1.4874 (25.3° C.) |
| 4-32 | i-Pr | C—CF₃ | H | CF(CF₃)₂ | Et | 1 | |
| 4-33 | i-Pr | C—CF₃ | H | CF(CF₃)₂ | Et | 2 | |
| 4-34 | i-Pr | C—CF₃ | Ac | CF(CF₃)₂ | Et | 0 | 1.4815 (24.4° C.) |
| 4-35 | i-Pr | C—CF₃ | Ac | CF(CF₃)₂ | Et | 1 | |
| 4-36 | i-Pr | C—CF₃ | Ac | CF(CF₃)₂ | Et | 2 | 124-125 |
| 4-37 | CH₂CH=CH₂ | C—CF₃ | H | CF(CF₃)₂ | Me | 0 | NMR |
| 4-38 | CH₂CH=CH₂ | C—CF₃ | H | CF(CF₃)₂ | Me | 1 | |
| 4-39 | CH₂CH=CH₂ | C—CF₃ | H | CF(CF₃)₂ | Me | 2 | |
| 4-40 | CH₂CH=CH₂ | C—CF₃ | Ac | CF(CF₃)₂ | Me | 0 | NMR |
| 4-41 | CH₂CH=CH₂ | C—CF₃ | Ac | CF(CF₃)₂ | Me | 1 | |
| 4-42 | CH₂CH=CH₂ | C—CF₃ | Ac | CF(CF₃)₂ | Me | 2 | 118.5-120.5 |
| 4-43 | CH₂CH=CH₂ | C—CF₃ | H | CF(CF₃)₂ | Et | 0 | |
| 4-44 | CH₂CH=CH₂ | C—CF₃ | H | CF(CF₃)₂ | Et | 1 | |
| 4-45 | CH₂CH=CH₂ | C—CF₃ | H | CF(CF₃)₂ | Et | 2 | |
| 4-46 | CH₂CH=CH₂ | C—CF₃ | Ac | CF(CF₃)₂ | Et | 0 | |
| 4-47 | CH₂CH=CH₂ | C—CF₃ | Ac | CF(CF₃)₂ | Et | 1 | |
| 4-48 | CH₂CH=CH₂ | C—CF₃ | Ac | CF(CF₃)₂ | Et | 2 | |
| 4-49 | t-Bu | C—CF₃ | H | CF(CF₃)₂ | Me | 0 | 151.0-151.1 |
| 4-50 | t-Bu | C—CF₃ | H | CF(CF₃)₂ | Me | 1 | |

$R^4$, $R^5$ and $R^7$ each represent a hydrogen atom, and $A^1$, $A^3$ and $A^4$ each represent a CH group.

TABLE 4-3

| Compound No. | R¹ | A² | R³ | R⁶ | Z | m | Physical property |
|---|---|---|---|---|---|---|---|
| 4-51 | t-Bu | C—CF₃ | H | CF(CF₃)₂ | Me | 2 | |
| 4-52 | t-Bu | C—CF₃ | Ac | CF(CF₃)₂ | Me | 0 | NMR |
| 4-53 | t-Bu | C—CF₃ | Ac | CF(CF₃)₂ | Me | 1 | |

TABLE 4-3-continued

| Compound No. | R¹ | A² | R³ | R⁶ | Z | m | Physical property |
|---|---|---|---|---|---|---|---|
| 4-54 | t-Bu | C—CF₃ | Ac | CF(CF₃)₂ | Me | 2 | 130.1-132.3 |
| 4-55 | t-Bu | C—CF₃ | H | CF(CF₃)₂ | Et | 0 | |
| 4-56 | t-Bu | C—CF₃ | H | CF(CF₃)₂ | Et | 1 | |
| 4-57 | t-Bu | C—CF₃ | H | CF(CF₃)₂ | Et | 2 | |
| 4-58 | t-Bu | C—CF₃ | Ac | CF(CF₃)₂ | Et | 0 | |
| 4-59 | t-Bu | C—CF₃ | Ac | CF(CF₃)₂ | Et | 1 | |
| 4-60 | t-Bu | C—CF₃ | Ac | CF(CF₃)₂ | Et | 2 | |
| 4-61 | 4-F—Ph | C—CF₃ | H | CF(CF₃)₂ | Me | 0 | 1.4011 (24.6° C.) |
| 4-62 | 4-F—Ph | C—CF₃ | H | CF(CF₃)₂ | Me | 1 | |
| 4-63 | 4-F—Ph | C—CF₃ | H | CF(CF₃)₂ | Me | 2 | 191-192 |
| 4-64 | 4-F—Ph | C—CF₃ | Ac | CF(CF₃)₂ | Me | 0 | |
| 4-65 | 4-F—Ph | C—CF₃ | Ac | CF(CF₃)₂ | Me | 1 | |
| 4-66 | 4-F—Ph | C—CF₃ | Ac | CF(CF₃)₂ | Me | 2 | 79-81 |
| 4-67 | 4-F—Ph | C—CF₃ | H | CF(CF₃)₂ | Et | 0 | |
| 4-68 | 4-F—Ph | C—CF₃ | H | CF(CF₃)₂ | Et | 1 | |
| 4-69 | 4-F—Ph | C—CF₃ | H | CF(CF₃)₂ | Et | 2 | |
| 4-70 | 4-F—Ph | C—CF₃ | Ac | CF(CF₃)₂ | Et | 0 | |
| 4-71 | 4-F—Ph | C—CF₃ | Ac | CF(CF₃)₂ | Et | 1 | |
| 4-72 | 4-F—Ph | C—CF₃ | Ac | CF(CF₃)₂ | Et | 2 | |

$R^4$, $R^5$ and $R^7$ each represent a hydrogen atom, and $A^1$, $A^3$ and $A^4$ each represent a CH group.

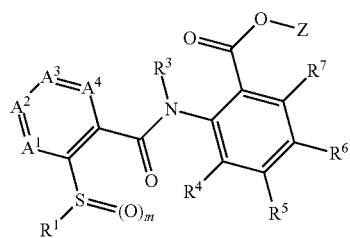

(1)

TABLE 5-1

| Compound No. | R¹ | A² | R³ | R⁶ | Z | m | Physical property |
|---|---|---|---|---|---|---|---|
| 5-1 | Et | C—CF₃ | H | F | Me | 0 | 134-135 |
| 5-2 | Et | C—CF₃ | H | F | Me | 1 | |
| 5-3 | Et | C—CF₃ | H | F | Me | 2 | 145-147 |
| 5-4 | Et | C—CF₃ | Ac | F | Me | 0 | 1.5340 (24.1° C.) |
| 5-5 | Et | C—CF₃ | Ac | F | Me | 1 | |
| 5-6 | Et | C—CF₃ | Ac | F | Me | 2 | 50-52 |
| 5-7 | Et | C—CF₃ | H | OCH₂CF₃ | Me | 0 | 134-136 |
| 5-8 | Et | C—CF₃ | H | OCH₂CF₃ | Me | 1 | |
| 5-9 | Et | C—CF₃ | H | OCH₂CF₃ | Me | 2 | 103-104 |
| 5-10 | Et | C—CF₃ | Ac | OCH₂CF₃ | Me | 0 | 1.4810 (24.0° C.) |
| 5-11 | Et | C—CF₃ | Ac | OCH₂CF₃ | Me | 1 | |
| 5-12 | Et | C—CF₃ | Ac | OCH₂CF₃ | Me | 2 | 59-60 |
| 5-13 | Et | C—CF₃ | H | OCF₂CHFCF₃ | Me | 0 | 101-102 |
| 5-14 | Et | C—CF₃ | H | OCF₂CHFCF₃ | Me | 1 | |
| 5-15 | Et | C—CF₃ | H | OCF₂CHFCF₃ | Me | 2 | 130-132 |
| 5-16 | Et | C—CF₃ | Ac | OCF₂CHFCF₃ | Me | 0 | |
| 5-17 | Et | C—CF₃ | Ac | OCF₂CHFCF₃ | Me | 1 | |
| 5-18 | Et | C—CF₃ | Ac | OCF₂CHFCF₃ | Me | 2 | 1.3510 (26.4° C.) |
| 5-19 | Et | C—CF₃ | H | C(OMe)(CF₃)₂ | Me | 0 | |
| 5-20 | Et | C—CF₃ | H | C(OMe)(CF₃)₂ | Me | 1 | |
| 5-21 | Et | C—CF₃ | H | C(OMe)(CF₃)₂ | Me | 2 | |
| 5-22 | Et | C—CF₃ | Ac | C(OMe)(CF₃)₂ | Me | 0 | |
| 5-23 | Et | C—CF₃ | Ac | C(OMe)(CF₃)₂ | Me | 1 | |
| 5-24 | Et | C—CF₃ | Ac | C(OMe)(CF₃)₂ | Me | 2 | |
| 5-25 | Et | C—CF₃ | H | C(OEt)(CF₃)₂ | Me | 0 | 84-85 |

$R^4$, $R^5$ and $R^7$ each represent a hydrogen atom, and $A^1$, $A^3$ and $A^4$ each represent a CH group.

TABLE 5-2

| Compound No. | R¹ | A² | R³ | R⁶ | Z | m | Physical property |
|---|---|---|---|---|---|---|---|
| 5-26 | Et | C—CF₃ | H | C(OEt)(CF₃)₂ | Me | 1 | |
| 5-27 | Et | C—CF₃ | H | C(OEt)(CF₃)₂ | Me | 2 | |
| 5-28 | Et | C—CF₃ | Ac | C(OEt)(CF₃)₂ | Me | 0 | |
| 5-29 | Et | C—CF₃ | Ac | C(OEt)(CF₃)₂ | Me | 1 | |
| 5-30 | Et | C—CF₃ | Ac | C(OEt)(CF₃)₂ | Me | 2 | |
| 5-31 | Et | C—CF₃ | H | O-(4—OCF₃—Ph) | Me | 0 | 103-104 |
| 5-32 | Et | C—CF₃ | H | O-(4—OCF₃—Ph) | Me | 1 | 108-109 |
| 5-33 | Et | C—CF₃ | H | O-(4—OCF₃—Ph) | Me | 2 | 126-127 |
| 5-34 | Et | C—CF₃ | Ac | O-(4—OCF₃—Ph) | Me | 0 | |
| 5-35 | Et | C—CF₃ | Ac | O-(4—OCF₃—Ph) | Me | 1 | |
| 5-36 | Et | C—CF₃ | Ac | O-(4—OCF₃—Ph) | Me | 2 | |
| 5-37 | Et | C—CF₃ | H | O-(4-F—Ph) | Me | 0 | 125-126 |
| 5-38 | Et | C—CF₃ | H | O-(4-F—Ph) | Me | 1 | 159-160 |
| 5-39 | Et | C—CF₃ | H | O-(4-F—Ph) | Me | 2 | 1.4200 (27.2° C.) |
| 5-40 | Et | C—CF₃ | Ac | O-(4-F—Ph) | Me | 0 | |
| 5-41 | Et | C—CF₃ | Ac | O-(4-F—Ph) | Me | 1 | |
| 5-42 | Et | C—CF₃ | Ac | O-(4-F—Ph) | Me | 2 | |
| 5-43 | Et | C—CF₃ | H | Ph | Me | 0 | 180-181 |
| 5-44 | Et | C—CF₃ | H | Ph | Me | 1 | |
| 5-45 | Et | C—CF₃ | H | Ph | Me | 2 | |
| 5-46 | Et | C—CF₃ | Ac | Ph | Me | 0 | |
| 5-47 | Et | C—CF₃ | Ac | Ph | Me | 1 | |
| 5-48 | Et | C—CF₃ | Ac | Ph | Me | 2 | |
| 5-49 | Et | C—CF₃ | H | 4-OCF₃—Ph | Me | 0 | 127-128 |
| 5-50 | Et | C—CF₃ | H | 4-OCF₃—Ph | Me | 1 | |

$R^4$, $R^5$ and $R^7$ each represent a hydrogen atom, and $A^1$, $A^3$ and $A^4$ each represent a CH group.

TABLE 5-3

| Compound No. | R¹ | A² | R³ | R⁶ | Z | m | Physical property |
|---|---|---|---|---|---|---|---|
| 5-51 | Et | C—CF₃ | H | 4-OCF₃—Ph | Me | 2 | |
| 5-52 | Et | C—CF₃ | Ac | 4-OCF₃—Ph | Me | 0 | |
| 5-53 | Et | C—CF₃ | Ac | 4-OCF₃—Ph | Me | 1 | |
| 5-54 | Et | C—CF₃ | Ac | 4-OCF₃—Ph | Me | 2 | |
| 5-55 | Et | C—CF₃ | Ac | OCF₃ | Me | 0 | 1.5042 (25.6° C.) |
| 5-56 | Et | C—CF₃ | Ac | OCF₃ | Me | 1 | |
| 5-57 | Et | C—CF₃ | Ac | OCF₃ | Me | 2 | NMR |
| 5-58 | Et | C—CF₃ | H | OCF₃ | Et | 0 | 107.3-107.4 |
| 5-59 | Et | C—CF₃ | H | OCF₃ | Et | 1 | |
| 5-60 | Et | C—CF₃ | H | OCF₃ | Et | 2 | 178-179 |
| 5-61 | Et | C—CF₃ | Ac | OCF₃ | Et | 0 | 1.4971 (25.5° C.) |
| 5-62 | Et | C—CF₃ | Ac | OCF₃ | Et | 1 | |
| 5-63 | Et | C—CF₃ | Ac | OCF₃ | Et | 2 | 49-50 |
| 5-64 | Et | C—Cl | H | OCF₃ | Me | 0 | 88.3-89.0 |
| 5-65 | Et | C—Cl | H | OCF₃ | Me | 1 | |
| 5-66 | Et | C—Cl | H | OCF₃ | Me | 2 | |
| 5-67 | Et | C—Cl | Ac | OCF₃ | Me | 0 | 1.4532 (25.4° C.) |
| 5-68 | Et | C—Cl | Ac | OCF₃ | Me | 1 | |
| 5-69 | Et | C—Cl | Ac | OCF₃ | Me | 2 | 112.3-113.5 |
| 5-70 | Et | C—CF₃ | H | OCH₂(2,3,4,5,6-F₅Ph) | Me | 0 | 143-144 |
| 5-71 | Et | C—CF₃ | H | OCH₂(2,3,4,5,6-F₅Ph) | Me | 1 | |
| 5-72 | Et | C—CF₃ | H | OCH₂(2,3,4,5,6-F₅Ph) | Me | 2 | 182-183 |
| 5-73 | Et | C—CF₃ | Ac | OCH₂(2,3,4,5,6-F₅Ph) | Me | 0 | 1.5133 (25.1° C.) |
| 5-74 | Et | C—CF₃ | Ac | OCH₂(2,3,4,5,6-F₅Ph) | Me | 1 | |
| 5-75 | Et | C—CF₃ | Ac | OCH₂(2,3,4,5,6-F₅Ph) | Me | 2 | 62-63 |

$R^4$, $R^5$ and $R^7$ each represent a hydrogen atom, and $A^1$, $A^3$ and $A^4$ each represent a CH group.

(1)

TABLE 6

| Compound No. | R¹ | R³ | A¹ | A² | A³ | A⁴ | Z | m | Physical property |
|---|---|---|---|---|---|---|---|---|---|
| 6-1 | Et | H | CH | CCl | CH | CH | Me | 0 | 107-108 |
| 6-2 | Et | H | CH | CCl | CH | CH | Me | 1 | |
| 6-3 | Et | H | CH | CCl | CH | CH | Me | 2 | 143-144 |
| 6-4 | Et | Ac | CH | CCl | CH | CH | Me | 0 | 1.3540 (20.1° C.) |
| 6-5 | Et | Ac | CH | CCl | CH | CH | Me | 1 | |
| 6-6 | Et | Ac | CH | CCl | CH | CH | Me | 2 | 157-159 |
| 6-7 | Et | H | CH | CBr | CH | CH | Me | 0 | 100-102 |
| 6-8 | Et | H | CH | CBr | CH | CH | Me | 1 | |
| 6-9 | Et | H | CH | CBr | CH | CH | Me | 2 | 148-150 |
| 6-10 | Et | Ac | CH | CBr | CH | CH | Me | 0 | 1.4536 (24.6° C.) |
| 6-11 | Et | Ac | CH | CBr | CH | CH | Me | 1 | |
| 6-12 | Et | Ac | CH | CBr | CH | CH | Me | 2 | 49-51 |
| 6-13 | Et | H | CH | CH | CCF₃ | CH | Me | 0 | 102-104 |
| 6-14 | Et | H | CH | CH | CCF₃ | CH | Me | 1 | 53-56 |
| 6-15 | Et | H | CH | CH | CCF₃ | CH | Me | 2 | 149-150 |
| 6-16 | Et | Ac | CH | CH | CCF₃ | CH | Me | 0 | 1.5770 (23.6° C.) |
| 6-17 | Et | Ac | CH | CH | CCF₃ | CH | Me | 1 | |
| 6-18 | Et | Ac | CH | CH | CCF₃ | CH | Me | 2 | |
| 6-19 | Et | H | CH | C—OCHF₂ | CH | CH | Me | 0 | 76-78 |
| 6-20 | Et | H | CH | C—OCHF₂ | CH | CH | Me | 1 | |
| 6-21 | Et | H | CH | C—OCHF₂ | CH | CH | Me | 2 | 189-190 |
| 6-22 | Et | Ac | CH | C—OCHF₂ | CH | CH | Me | 0 | 1.4722 (24.4° C.) |
| 6-23 | Et | Ac | CH | C—OCHF₂ | CH | CH | Me | 1 | |
| 6-24 | Et | Ac | CH | C—OCHF₂ | CH | CH | Me | 2 | 129-130 |

$R^4$, $R^5$ and $R^7$ each represent a hydrogen atom, and $R^6$ represents $CF(CF_3)_2$.

(1)

TABLE 7-1

| Compound No. | $R^1$ | $A^2$ | $R^3$ | $R^4$ | $R^6$ | Z | m | Physical property |
|---|---|---|---|---|---|---|---|---|
| 7-1 | Et | C—CF$_3$ | COc-Pr | H | CF(CF$_3$)$_2$ | Me | 0 | |
| 7-2 | Et | C—CF$_3$ | COc-Pr | H | CF(CF$_3$)$_2$ | Me | 1 | |
| 7-3 | Et | C—CF$_3$ | COc-Pr | H | CF(CF$_3$)$_2$ | Me | 2 | 62-63 |
| 7-4 | Et | C—CF$_3$ | COc-Pen | H | CF(CF$_3$)$_2$ | Me | 0 | |
| 7-5 | Et | C—CF$_3$ | COc-Pen | H | CF(CF$_3$)$_2$ | Me | 1 | |
| 7-6 | Et | C—CF$_3$ | COc-Pen | H | CF(CF$_3$)$_2$ | Me | 2 | |
| 7-7 | Et | C—CF$_3$ | COc-Hex | H | CF(CF$_3$)$_2$ | Me | 0 | |
| 7-8 | Et | C—CF$_3$ | COc-Hex | H | CF(CF$_3$)$_2$ | Me | 1 | |
| 7-9 | Et | C—CF$_3$ | COc-Hex | H | CF(CF$_3$)$_2$ | Me | 2 | 62-63 |
| 7-10 | Et | C—CF$_3$ | H | H | CF(CF$_3$)$_2$ | CH$_2$CN | 0 | 185-186 |
| 7-11 | Et | C—CF$_3$ | H | H | CF(CF$_3$)$_2$ | CH$_2$CN | 1 | |
| 7-12 | Et | C—CF$_3$ | H | H | CF(CF$_3$)$_2$ | CH$_2$CN | 2 | 110-113 |
| 7-13 | Et | C—CF$_3$ | Ac | H | CF(CF$_3$)$_2$ | CH$_2$CN | 0 | |
| 7-14 | Et | C—CF$_3$ | Ac | H | CF(CF$_3$)$_2$ | CH$_2$CN | 1 | |
| 7-15 | Et | C—CF$_3$ | Ac | H | CF(CF$_3$)$_2$ | CH$_2$CN | 2 | 128-130 |
| 7-16 | Et | C—CF$_3$ | CH$_2$CO$_2$Me | H | CF(CF$_3$)$_2$ | Me | 0 | |
| 7-17 | Et | C—CF$_3$ | CH$_2$CO$_2$Me | H | CF(CF$_3$)$_2$ | Me | 1 | |
| 7-18 | Et | C—CF$_3$ | CH$_2$CO$_2$Me | H | CF(CF$_3$)$_2$ | Me | 2 | 65-66 |
| 7-19 | Et | C—CF$_3$ | n-Hex | H | CF(CF$_3$)$_2$ | Me | 0 | 1.3060 (20.2° C.) |
| 7-20 | Et | C—CF$_3$ | n-Hex | H | CF(CF$_3$)$_2$ | Me | 1 | |
| 7-21 | Et | C—CF$_3$ | n-Hex | H | CF(CF$_3$)$_2$ | Me | 2 | |
| 7-22 | Et | C—CF$_3$ | COCH$_2$OMe | H | CF(CF$_3$)$_2$ | Me | 0 | |
| 7-23 | Et | C—CF$_3$ | COCH$_2$OMe | H | CF(CF$_3$)$_2$ | Me | 1 | |
| 7-24 | Et | C—CF$_3$ | COCH$_2$OMe | H | CF(CF$_3$)$_2$ | Me | 2 | |
| 7-25 | Et | C—CF$_3$ | COCH$_2$Cl | H | CF(CF$_3$)$_2$ | Me | 0 | |

$R^5$ and $R^7$ each represent a hydrogen atom, and $A^3$ and $A^4$ each represent a CH group.

TABLE 7-2

| Compound No. | $R^1$ | $A^2$ | $R^3$ | $R^4$ | $R^6$ | Z | m | Physical property |
|---|---|---|---|---|---|---|---|---|
| 7-26 | Et | C—CF$_3$ | COCH$_2$Cl | H | CF(CF$_3$)$_2$ | Me | 1 | |
| 7-27 | Et | C—CF$_3$ | COCH$_2$Cl | H | CF(CF$_3$)$_2$ | Me | 2 | |
| 7-28 | Et | C—CF$_3$ | OMe | H | CF(CF$_3$)$_2$ | Me | 0 | |
| 7-29 | Et | C—CF$_3$ | OMe | H | CF(CF$_3$)$_2$ | Me | 1 | |
| 7-30 | Et | C—CF$_3$ | OMe | H | CF(CF$_3$)$_2$ | Me | 2 | |
| 7-31 | Et | C—CF$_3$ | H | Me | CF(CF$_3$)$_2$ | Me | 0 | |
| 7-32 | Et | C—CF$_3$ | H | Me | CF(CF$_3$)$_2$ | Me | 1 | |
| 7-33 | Et | C—CF$_3$ | H | Me | CF(CF$_3$)$_2$ | Me | 2 | |
| 7-34 | Et | C—CF$_3$ | Ac | Me | CF(CF$_3$)$_2$ | Me | 0 | |
| 7-35 | Et | C—CF$_3$ | Ac | Me | CF(CF$_3$)$_2$ | Me | 1 | |
| 7-36 | Et | C—CF$_3$ | Ac | Me | CF(CF$_3$)$_2$ | Me | 2 | |
| 7-37 | Et | C—CF$_3$ | H | F | CF(CF$_3$)$_2$ | Me | 0 | |
| 7-38 | Et | C—CF$_3$ | H | F | CF(CF$_3$)$_2$ | Me | 1 | |
| 7-39 | Et | C—CF$_3$ | H | F | CF(CF$_3$)$_2$ | Me | 2 | |
| 7-40 | Et | C—CF$_3$ | Ac | F | CF(CF$_3$)$_2$ | Me | 0 | |
| 7-41 | Et | C—CF$_3$ | Ac | F | CF(CF$_3$)$_2$ | Me | 1 | |
| 7-42 | Et | C—CF$_3$ | Ac | F | CF(CF$_3$)$_2$ | Me | 2 | |
| 7-43 | Et | C—CF$_3$ | H | Cl | CF(CF$_3$)$_2$ | Me | 0 | |
| 7-44 | Et | C—CF$_3$ | H | Cl | CF(CF$_3$)$_2$ | Me | 1 | |
| 7-45 | Et | C—CF$_3$ | H | Cl | CF(CF$_3$)$_2$ | Me | 2 | |
| 7-46 | Et | C—CF$_3$ | Ac | Cl | CF(CF$_3$)$_2$ | Me | 0 | |
| 7-47 | Et | C—CF$_3$ | Ac | Cl | CF(CF$_3$)$_2$ | Me | 1 | |
| 7-48 | Et | C—CF$_3$ | Ac | Cl | CF(CF$_3$)$_2$ | Me | 2 | |
| 7-49 | Et | C—CF$_3$ | H | Br | CF(CF$_3$)$_2$ | Me | 0 | |
| 7-50 | Et | C—CF$_3$ | H | Br | CF(CF$_3$)$_2$ | Me | 1 | |

$R^5$ and $R^7$ each represent a hydrogen atom, and $A^3$ and $A^4$ each represent a CH group.

TABLE 7-3

| Compound No. | $R^1$ | $A^2$ | $R^3$ | $R^4$ | $R^6$ | Z | m | Physical property |
|---|---|---|---|---|---|---|---|---|
| 7-51 | Et | C—CF$_3$ | H | Br | CF(CF$_3$)$_2$ | Me | 2 | |
| 7-52 | Et | C—CF$_3$ | Ac | Br | CF(CF$_3$)$_2$ | Me | 0 | |
| 7-53 | Et | C—CF$_3$ | Ac | Br | CF(CF$_3$)$_2$ | Me | 1 | |
| 7-54 | Et | C—CF$_3$ | Ac | Br | CF(CF$_3$)$_2$ | Me | 2 | |
| 7-55 | Et | C—CF$_3$ | H | I | CF(CF$_3$)$_2$ | Me | 0 | |
| 7-56 | Et | C—CF$_3$ | H | I | CF(CF$_3$)$_2$ | Me | 1 | |
| 7-57 | Et | C—CF$_3$ | H | I | CF(CF$_3$)$_2$ | Me | 2 | |
| 7-58 | Et | C—CF$_3$ | Ac | I | CF(CF$_3$)$_2$ | Me | 0 | |
| 7-59 | Et | C—CF$_3$ | Ac | I | CF(CF$_3$)$_2$ | Me | 1 | |
| 7-60 | Et | C—CF$_3$ | Ac | I | CF(CF$_3$)$_2$ | Me | 2 | |
| 7-61 | Et | C—CF$_3$ | H | CN | CF(CF$_3$)$_2$ | Me | 0 | |
| 7-62 | Et | C—CF$_3$ | H | CN | CF(CF$_3$)$_2$ | Me | 1 | |
| 7-63 | Et | C—CF$_3$ | H | CN | CF(CF$_3$)$_2$ | Me | 2 | |
| 7-64 | Et | C—CF$_3$ | Ac | CN | CF(CF$_3$)$_2$ | Me | 0 | |
| 7-65 | Et | C—CF$_3$ | Ac | CN | CF(CF$_3$)$_2$ | Me | 1 | |
| 7-66 | Et | C—CF$_3$ | Ac | CN | CF(CF$_3$)$_2$ | Me | 2 | |
| 7-67 | Et | C—CF$_3$ | H | NO$_2$ | CF(CF$_3$)$_2$ | Me | 0 | |
| 7-68 | Et | C—CF$_3$ | H | NO$_2$ | CF(CF$_3$)$_2$ | Me | 1 | |
| 7-69 | Et | C—CF$_3$ | H | NO$_2$ | CF(CF$_3$)$_2$ | Me | 2 | |
| 7-70 | Et | C—CF$_3$ | Ac | NO$_2$ | CF(CF$_3$)$_2$ | Me | 0 | |
| 7-71 | Et | C—CF$_3$ | Ac | NO$_2$ | CF(CF$_3$)$_2$ | Me | 1 | |
| 7-72 | Et | C—CF$_3$ | Ac | NO$_2$ | CF(CF$_3$)$_2$ | Me | 2 | |
| 7-73 | Et | C—CF$_3$ | Ac | H | CF(CF$_3$)$_2$ | Et | 0 | |
| 7-74 | Et | C—CF$_3$ | Ac | H | CF(CF$_3$)$_2$ | Et | 1 | |
| 7-75 | Et | C—CF$_3$ | Ac | H | CF(CF$_3$)$_2$ | Et | 2 | |

$R^5$ and $R^7$ each represent a hydrogen atom, and $A^3$ and $A^4$ each represent a CH group.

TABLE 7-4

| Compound No. | $R^1$ | $A^2$ | $R^3$ | $R^4$ | $R^6$ | Z | m | Physical property |
|---|---|---|---|---|---|---|---|---|
| 7-76 | Et | C—CF$_3$ | COc-Pr | H | CF(CF$_3$)$_2$ | Et | 0 | |
| 7-77 | Et | C—CF$_3$ | COc-Pr | H | CF(CF$_3$)$_2$ | Et | 1 | |
| 7-78 | Et | C—CF$_3$ | COc-Pr | H | CF(CF$_3$)$_2$ | Et | 2 | |
| 7-79 | Et | C—CF$_3$ | COc-Pen | H | CF(CF$_3$)$_2$ | Et | 0 | |

TABLE 7-4-continued

| Compound No. | $R^1$ | $A^2$ | $R^3$ | $R^4$ | $R^6$ | Z | m | Physical property |
|---|---|---|---|---|---|---|---|---|
| 7-80 | Et | C—CF$_3$ | COc-Pen | H | CF(CF$_3$)$_2$ | Et | 1 | |
| 7-81 | Et | C—CF$_3$ | COc-Pen | H | CF(CF$_3$)$_2$ | Et | 2 | |
| 7-82 | Et | C—CF$_3$ | COc-Hex | H | CF(CF$_3$)$_2$ | Et | 0 | |
| 7-83 | Et | C—CF$_3$ | COc-Hex | H | CF(CF$_3$)$_2$ | Et | 1 | |
| 7-84 | Et | C—CF$_3$ | COc-Hex | H | CF(CF$_3$)$_2$ | Et | 2 | |
| 7-85 | Et | C—CF$_3$ | COCH$_2$OMe | H | CF(CF$_3$)$_2$ | Et | 0 | |
| 7-86 | Et | C—CF$_3$ | COCH$_2$OMe | H | CF(CF$_3$)$_2$ | Et | 1 | |
| 7-87 | Et | C—CF$_3$ | COCH$_2$OMe | H | CF(CF$_3$)$_2$ | Et | 2 | |
| 7-88 | Et | C—CF$_3$ | COCH$_2$Cl | H | CF(CF$_3$)$_2$ | Et | 0 | |
| 7-89 | Et | C—CF$_3$ | COCH$_2$Cl | H | CF(CF$_3$)$_2$ | Et | 1 | |
| 7-90 | Et | C—CF$_3$ | COCH$_2$Cl | H | CF(CF$_3$)$_2$ | Et | 2 | |
| 7-91 | Et | C—CF$_3$ | OMe | H | CF(CF$_3$)$_2$ | Et | 0 | |
| 7-92 | Et | C—CF$_3$ | OMe | H | CF(CF$_3$)$_2$ | Et | 1 | |
| 7-93 | Et | C—CF$_3$ | OMe | H | CF(CF$_3$)$_2$ | Et | 2 | |
| 7-94 | Et | C—CF$_3$ | COEt | H | OCF$_3$ | Me | 0 | |
| 7-95 | Et | C—CF$_3$ | COEt | H | OCF$_3$ | Me | 1 | |
| 7-96 | Et | C—CF$_3$ | COEt | H | OCF$_3$ | Me | 2 | |
| 7-97 | Et | C—CF$_3$ | COi-Pr | H | OCF$_3$ | Me | 0 | |
| 7-98 | Et | C—CF$_3$ | COi-Pr | H | OCF$_3$ | Me | 1 | |
| 7-99 | Et | C—CF$_3$ | COi-Pr | H | OCF$_3$ | Me | 2 | 82-83 |
| 7-100 | Et | C—CF$_3$ | COc-Pr | H | OCF$_3$ | Me | 0 | |

$R^5$ and $R^7$ each represent a hydrogen atom, and $A^3$ and $A^4$ each represent a CH group.

TABLE 7-5

| Compound No. | $R^1$ | $A^2$ | $R^3$ | $R^4$ | $R^6$ | Z | m | Physical property |
|---|---|---|---|---|---|---|---|---|
| 7-101 | Et | C—CF$_3$ | COc-Pr | H | OCF$_3$ | Me | 1 | |
| 7-102 | Et | C—CF$_3$ | COc-Pr | H | OCF$_3$ | Me | 2 | |
| 7-103 | Et | C—CF$_3$ | COc-Pen | H | OCF$_3$ | Me | 0 | |
| 7-104 | Et | C—CF$_3$ | COc-Pen | H | OCF$_3$ | Me | 1 | |
| 7-105 | Et | C—CF$_3$ | COc-Pen | H | OCF$_3$ | Me | 3 | |
| 7-106 | Et | C—CF$_3$ | COc-Hex | H | OCF$_3$ | Me | 0 | |
| 7-107 | Et | C—CF$_3$ | COc-Hex | H | OCF$_3$ | Me | 1 | |
| 7-108 | Et | C—CF$_3$ | COc-Hex | H | OCF$_3$ | Me | 2 | |
| 7-109 | Et | C—CF$_3$ | CO$_2$Me | H | OCF$_3$ | Me | 0 | |
| 7-110 | Et | C—CF$_3$ | CO$_2$Me | H | OCF$_3$ | Me | 1 | |
| 7-111 | Et | C—CF$_3$ | CO$_2$Me | H | OCF$_3$ | Me | 2 | |
| 7-112 | Et | C—CF$_3$ | CO$_2$Et | H | OCF$_3$ | Me | 0 | |
| 7-113 | Et | C—CF$_3$ | CO$_2$Et | H | OCF$_3$ | Me | 1 | |
| 7-114 | Et | C—CF$_3$ | CO$_2$Et | H | OCF$_3$ | Me | 2 | |
| 7-115 | Et | C—CF$_3$ | COCH$_2$OMe | H | OCF$_3$ | Me | 0 | |
| 7-116 | Et | C—CF$_3$ | COCH$_2$OMe | H | OCF$_3$ | Me | 1 | |
| 7-117 | Et | C—CF$_3$ | COCH$_2$OMe | H | OCF$_3$ | Me | 2 | |
| 7-118 | Et | C—CF$_3$ | COCH$_2$Cl | H | OCF$_3$ | Me | 0 | |
| 7-119 | Et | C—CF$_3$ | COCH$_2$Cl | H | OCF$_3$ | Me | 1 | |
| 7-120 | Et | C—CF$_3$ | COCH$_2$Cl | H | OCF$_3$ | Me | 2 | |
| 7-121 | Et | C—CF$_3$ | OMe | H | OCF$_3$ | Me | 0 | |
| 7-122 | Et | C—CF$_3$ | OMe | H | OCF$_3$ | Me | 1 | |
| 7-123 | Et | C—CF$_3$ | OMe | H | OCF$_3$ | Me | 2 | |
| 7-124 | Et | C—CF$_3$ | H | CN | OCF$_3$ | Me | 0 | |
| 7-125 | Et | C—CF$_3$ | H | CN | OCF$_3$ | Me | 1 | |

$R^5$ and $R^7$ each represent a hydrogen atom, and $A^3$ and $A^4$ each represent a CH group.

TABLE 7-6

| Compound No. | $R^1$ | $A^2$ | $R^3$ | $R^4$ | $R^6$ | Z | m | Physical property |
|---|---|---|---|---|---|---|---|---|
| 7-126 | Et | C—CF$_3$ | H | CN | OCF$_3$ | Me | 2 | |
| 7-127 | Et | C—CF$_3$ | Ac | CN | OCF$_3$ | Me | 0 | |
| 7-128 | Et | C—CF$_3$ | Ac | CN | OCF$_3$ | Me | 1 | |
| 7-129 | Et | C—CF$_3$ | Ac | CN | OCF$_3$ | Me | 2 | |
| 7-130 | Et | C—CF$_3$ | H | NO$_2$ | OCF$_3$ | Me | 0 | |
| 7-131 | Et | C—CF$_3$ | H | NO$_2$ | OCF$_3$ | Me | 1 | |
| 7-132 | Et | C—CF$_3$ | H | NO$_2$ | OCF$_3$ | Me | 2 | |
| 7-133 | Et | C—CF$_3$ | Ac | NO$_2$ | OCF$_3$ | Me | 0 | |
| 7-134 | Et | C—CF$_3$ | Ac | NO$_2$ | OCF$_3$ | Me | 1 | |
| 7-135 | Et | C—CF$_3$ | Ac | NO$_2$ | OCF$_3$ | Me | 2 | |
| 7-136 | Et | C—CF$_3$ | H | F | OCF$_3$ | Me | 0 | |
| 7-137 | Et | C—CF$_3$ | H | F | OCF$_3$ | Me | 1 | |
| 7-138 | Et | C—CF$_3$ | H | F | OCF$_3$ | Me | 2 | |
| 7-139 | Et | C—CF$_3$ | Ac | F | OCF$_3$ | Me | 0 | |
| 7-140 | Et | C—CF$_3$ | Ac | F | OCF$_3$ | Me | 1 | |
| 7-141 | Et | C—CF$_3$ | Ac | F | OCF$_3$ | Me | 2 | |
| 7-142 | Et | C—CF$_3$ | H | Cl | OCF$_3$ | Me | 0 | |
| 7-143 | Et | C—CF$_3$ | H | Cl | OCF$_3$ | Me | 1 | |
| 7-144 | Et | C—CF$_3$ | H | Cl | OCF$_3$ | Me | 2 | |
| 7-145 | Et | C—CF$_3$ | Ac | Cl | OCF$_3$ | Me | 0 | |
| 7-146 | Et | C—CF$_3$ | Ac | Cl | OCF$_3$ | Me | 1 | |
| 7-147 | Et | C—CF$_3$ | Ac | Cl | OCF$_3$ | Me | 2 | |
| 7-148 | Et | C—CF$_3$ | H | Br | OCF$_3$ | Me | 0 | |
| 7-149 | Et | C—CF$_3$ | H | Br | OCF$_3$ | Me | 1 | |
| 7-150 | Et | C—CF$_3$ | H | Br | OCF$_3$ | Me | 2 | |

$R^5$ and $R^7$ each represent a hydrogen atom, and $A^3$ and $A^4$ each represent a CH group.

TABLE 7-7

| Compound No. | $R^1$ | $A^2$ | $R^3$ | $R^4$ | $R^6$ | Z | m | Physical property |
|---|---|---|---|---|---|---|---|---|
| 7-151 | Et | C—CF$_3$ | Ac | Br | OCF$_3$ | Me | 0 | |
| 7-152 | Et | C—CF$_3$ | Ac | Br | OCF$_3$ | Me | 1 | |
| 7-153 | Et | C—CF$_3$ | Ac | Br | OCF$_3$ | Me | 2 | |
| 7-154 | Et | C—CF$_3$ | H | I | OCF$_3$ | Me | 0 | |
| 7-155 | Et | C—CF$_3$ | H | I | OCF$_3$ | Me | 1 | |
| 7-156 | Et | C—CF$_3$ | H | I | OCF$_3$ | Me | 2 | |
| 7-157 | Et | C—CF$_3$ | Ac | I | OCF$_3$ | Me | 0 | |
| 7-158 | Et | C—CF$_3$ | Ac | I | OCF$_3$ | Me | 1 | |
| 7-159 | Et | C—CF$_3$ | Ac | I | OCF$_3$ | Me | 2 | |
| 7-160 | Et | C—CF$_3$ | COEt | H | OCF$_3$ | Et | 0 | |
| 7-161 | Et | C—CF$_3$ | COEt | H | OCF$_3$ | Et | 1 | |
| 7-162 | Et | C—CF$_3$ | COEt | H | OCF$_3$ | Et | 2 | |
| 7-163 | Et | C—CF$_3$ | COi-Pr | H | OCF$_3$ | Et | 0 | |
| 7-164 | Et | C—CF$_3$ | COi-Pr | H | OCF$_3$ | Et | 1 | |
| 7-165 | Et | C—CF$_3$ | COi-Pr | H | OCF$_3$ | Et | 2 | |
| 7-166 | Et | C—CF$_3$ | COc-Pr | H | OCF$_3$ | Et | 0 | |
| 7-167 | Et | C—CF$_3$ | COc-Pr | H | OCF$_3$ | Et | 1 | |
| 7-168 | Et | C—CF$_3$ | COc-Pr | H | OCF$_3$ | Et | 2 | |
| 7-169 | Et | C—CF$_3$ | COc-Pen | H | OCF$_3$ | Et | 0 | |
| 7-170 | Et | C—CF$_3$ | COc-Pen | H | OCF$_3$ | Et | 1 | |
| 7-171 | Et | C—CF$_3$ | COc-Pen | H | OCF$_3$ | Et | 2 | |
| 7-172 | Et | C—CF$_3$ | COc-Hex | H | OCF$_3$ | Et | 0 | |
| 7-173 | Et | C—CF$_3$ | COc-Hex | H | OCF$_3$ | Et | 1 | |
| 7-174 | Et | C—CF$_3$ | COc-Hex | H | OCF$_3$ | Et | 2 | |
| 7-175 | Et | C—CF$_3$ | CO$_2$Me | H | OCF$_3$ | Et | 0 | |

$R^5$ and $R^7$ each represent a hydrogen atom, and $A^3$ and $A^4$ each represent a CH group.

TABLE 7-8

| Compound No. | $R^1$ | $A^2$ | $R^3$ | $R^4$ | $R^6$ | Z | m | Physical property |
|---|---|---|---|---|---|---|---|---|
| 7-176 | Et | C—CF$_3$ | CO$_2$Me | H | OCF$_3$ | Et | 1 | |
| 7-177 | Et | C—CF$_3$ | CO$_2$Me | H | OCF$_3$ | Et | 2 | |
| 7-178 | Et | C—CF$_3$ | CO$_2$Et | H | OCF$_3$ | Et | 0 | |
| 7-179 | Et | C—CF$_3$ | CO$_2$Et | H | OCF$_3$ | Et | 1 | |
| 7-180 | Et | C—CF$_3$ | CO$_2$Et | H | OCF$_3$ | Et | 2 | |
| 7-181 | Et | C—CF$_3$ | COCH$_2$OMe | H | OCF$_3$ | Et | 0 | |
| 7-182 | Et | C—CF$_3$ | COCH$_2$OMe | H | OCF$_3$ | Et | 1 | |
| 7-183 | Et | C—CF$_3$ | COCH$_2$OMe | H | OCF$_3$ | Et | 2 | |
| 7-184 | Et | C—CF$_3$ | COCH$_2$Cl | H | OCF$_3$ | Et | 0 | |

TABLE 7-8-continued

| Compound No. | $R^1$ | $A^2$ | $R^3$ | $R^4$ | $R^6$ | Z | m | Physical property |
|---|---|---|---|---|---|---|---|---|
| 7-185 | Et | C—CF$_3$ | COCH$_2$Cl | H | OCF$_3$ | Et | 1 | |
| 7-186 | Et | C—CF$_3$ | COCH$_2$Cl | H | OCF$_3$ | Et | 2 | |
| 7-187 | Et | C—CF$_3$ | OMe | H | OCF$_3$ | Et | 0 | |
| 7-188 | Et | C—CF$_3$ | OMe | H | OCF$_3$ | Et | 1 | |
| 7-189 | Et | C—CF$_3$ | OMe | H | OCF$_3$ | Et | 2 | |

$R^5$ and $R^7$ each represent a hydrogen atom, and $A^3$ and $A^4$ each represent a CH group.

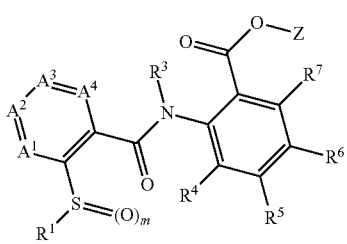

(1)

TABLE 8-1

| Compound No. | $R^1$ | $A^2$ | $R^3$ | $R^6$ | Z | m | Physical property |
|---|---|---|---|---|---|---|---|
| 8-1 | Et | C—CF$_3$ | H | O(3-Cl-5-CF$_3$-pyridin-2-yl) | Me | 0 | 133-134 |
| 8-2 | Et | C—CF$_3$ | H | O(3-Cl-5-CF$_3$-pyridin-2-yl) | Me | 1 | |
| 8-3 | Et | C—CF$_3$ | H | O(3-Cl-5-CF$_3$-pyridin-2-yl) | Me | 2 | 164-165 |
| 8-4 | Et | C—CF$_3$ | Ac | O(3-Cl-5-CF$_3$-pyridin-2-yl) | Me | 0 | 55-57 |
| 8-5 | Et | C—CF$_3$ | Ac | O(3-Cl-5-CF$_3$-pyridin-2-yl) | Me | 1 | |
| 8-6 | Et | C—CF$_3$ | Ac | O(3-Cl-5-CF$_3$-pyridin-2-yl) | Me | 2 | 194-195 |
| 8-7 | Et | C—CF$_3$ | H | OCH(CF$_3$)$_2$ | Me | 0 | 89-91 |
| 8-8 | Et | C—CF$_3$ | H | OCH(CF$_3$)$_2$ | Me | 1 | |
| 8-9 | Et | C—CF$_3$ | H | OCH(CF$_3$)$_2$ | Me | 2 | 99-101 |
| 8-10 | Et | C—CF$_3$ | Ac | OCH(CF$_3$)$_2$ | Me | 0 | 47-49 |
| 8-11 | Et | C—CF$_3$ | Ac | OCH(CF$_3$)$_2$ | Me | 1 | |
| 8-12 | Et | C—CF$_3$ | Ac | OCH(CF$_3$)$_2$ | Me | 2 | 52-54 |
| 8-13 | Et | C—CF$_3$ | H | OMe | Me | 0 | |
| 8-14 | Et | C—CF$_3$ | H | OMe | Me | 1 | |
| 8-15 | Et | C—CF$_3$ | H | OMe | Me | 2 | |
| 8-16 | Et | C—CF$_3$ | Ac | OMe | Me | 0 | |
| 8-17 | Et | C—CF$_3$ | Ac | OMe | Me | 1 | |
| 8-18 | Et | C—CF$_3$ | Ac | OMe | Me | 2 | |
| 8-19 | Et | C—CF$_3$ | H | OEt | Me | 0 | |
| 8-20 | Et | C—CF$_3$ | H | OEt | Me | 1 | |
| 8-21 | Et | C—CF$_3$ | H | OEt | Me | 2 | |
| 8-22 | Et | C—CF$_3$ | Ac | OEt | Me | 0 | |
| 8-23 | Et | C—CF$_3$ | Ac | OEt | Me | 1 | |
| 8-24 | Et | C—CF$_3$ | Ac | OEt | Me | 2 | |
| 8-25 | Et | C—CF$_3$ | Ac | On-Pr | Me | 0 | |

$R^4$, $R^5$ and $R^7$ each represent a hydrogen atom, and $A^1$, $A^3$ and $A^4$ each represent a CH group.

TABLE 8-2

| Compound No. | $R^1$ | $A^2$ | $R^3$ | $R^6$ | Z | m | Physical property |
|---|---|---|---|---|---|---|---|
| 8-26 | Et | C—CF$_3$ | H | On-Pr | Me | 1 | |
| 8-27 | Et | C—CF$_3$ | H | On-Pr | Me | 2 | |
| 8-28 | Et | C—CF$_3$ | Ac | On-Pr | Me | 0 | |

TABLE 8-2-continued

| Compound No. | $R^1$ | $A^2$ | $R^3$ | $R^6$ | Z | m | Physical property |
|---|---|---|---|---|---|---|---|
| 8-29 | Et | C—CF$_3$ | Ac | On-Pr | Me | 1 | |
| 8-30 | Et | C—CF$_3$ | Ac | On-Pr | Me | 2 | |
| 8-31 | Et | C—CF$_3$ | H | Oi-Pr | Me | 0 | |
| 8-32 | Et | C—CF$_3$ | H | Oi-Pr | Me | 1 | |
| 8-33 | Et | C—CF$_3$ | H | Oi-Pr | Me | 2 | 84-85 |
| 8-34 | Et | C—CF$_3$ | Ac | Oi-Pr | Me | 0 | |
| 8-35 | Et | C—CF$_3$ | Ac | Oi-Pr | Me | 1 | |
| 8-36 | Et | C—CF$_3$ | Ac | Oi-Pr | Me | 2 | |
| 8-37 | Et | C—CF$_3$ | H | On-Bu | Me | 0 | |
| 8-38 | Et | C—CF$_3$ | H | On-Bu | Me | 1 | |
| 8-39 | Et | C—CF$_3$ | H | On-Bu | Me | 2 | |
| 8-40 | Et | C—CF$_3$ | Ac | On-Bu | Me | 0 | |
| 8-41 | Et | C—CF$_3$ | Ac | On-Bu | Me | 1 | |
| 8-42 | Et | C—CF$_3$ | Ac | On-Bu | Me | 2 | |
| 8-43 | Et | C—CF$_3$ | H | Oi-Bu | Me | 0 | |
| 8-44 | Et | C—CF$_3$ | H | Oi-Bu | Me | 1 | |
| 8-45 | Et | C—CF$_3$ | H | Oi-Bu | Me | 2 | 91-92 |
| 8-46 | Et | C—CF$_3$ | Ac | Oi-Bu | Me | 0 | |
| 8-47 | Et | C—CF$_3$ | Ac | Oi-Bu | Me | 1 | |
| 8-48 | Et | C—CF$_3$ | Ac | Oi-Bu | Me | 2 | |
| 8-49 | Et | C—CF$_3$ | H | Os-Bu | Me | 0 | |
| 8-50 | Et | C—CF$_3$ | H | Os-Bu | Me | 1 | |

$R^4$, $R^5$ and $R^7$ each represent a hydrogen atom, and $A^1$, $A^3$ and $A^4$ each represent a CH group.

TABLE 8-3

| Compound No. | $R^1$ | $A^2$ | $R^3$ | $R^6$ | Z | m | Physical property |
|---|---|---|---|---|---|---|---|
| 8-51 | Et | C—CF$_3$ | H | Os-Bu | Me | 2 | 119-120 |
| 8-52 | Et | C—CF$_3$ | Ac | Os-Bu | Me | 0 | |
| 8-53 | Et | C—CF$_3$ | Ac | Os-Bu | Me | 1 | |
| 8-54 | Et | C—CF$_3$ | Ac | Os-Bu | Me | 2 | |
| 8-55 | Et | C—CF$_3$ | H | Ot-Bu | Me | 0 | |
| 8-56 | Et | C—CF$_3$ | H | Ot-Bu | Me | 1 | |
| 8-57 | Et | C—CF$_3$ | H | Ot-Bu | Me | 2 | |
| 8-58 | Et | C—CF$_3$ | Ac | Ot-Bu | Me | 0 | |
| 8-59 | Et | C—CF$_3$ | Ac | Ot-Bu | Me | 1 | |
| 8-60 | Et | C—CF$_3$ | Ac | Ot-Bu | Me | 2 | |
| 8-61 | Et | C—CF$_3$ | H | OCHF$_2$ | Me | 0 | |
| 8-62 | Et | C—CF$_3$ | H | OCHF$_2$ | Me | 1 | |
| 8-63 | Et | C—CF$_3$ | H | OCHF$_2$ | Me | 2 | |
| 8-64 | Et | C—CF$_3$ | Ac | OCHF$_2$ | Me | 0 | |
| 8-65 | Et | C—CF$_3$ | Ac | OCHF$_2$ | Me | 1 | |
| 8-66 | Et | C—CF$_3$ | Ac | OCHF$_2$ | Me | 2 | |
| 8-67 | Et | C—CF$_3$ | H | OCF$_2$Br | Me | 0 | |
| 8-68 | Et | C—CF$_3$ | H | OCF$_2$Br | Me | 1 | |
| 8-69 | Et | C—CF$_3$ | H | OCF$_2$Br | Me | 2 | |
| 8-70 | Et | C—CF$_3$ | Ac | OCF$_2$Br | Me | 0 | |
| 8-71 | Et | C—CF$_3$ | Ac | OCF$_2$Br | Me | 1 | |
| 8-72 | Et | C—CF$_3$ | Ac | OCF$_2$Br | Me | 2 | |
| 8-73 | Et | C—CF$_3$ | H | OCF$_2$CHF$_2$ | Me | 0 | |
| 8-74 | Et | C—CF$_3$ | H | OCF$_2$CHF$_2$ | Me | 1 | |
| 8-75 | Et | C—CF$_3$ | H | OCF$_2$CHF$_2$ | Me | 2 | |

$R^4$, $R^5$ and $R^7$ each represent a hydrogen atom, and $A^1$, $A^3$ and $A^4$ each represent a CH group.

TABLE 8-4

| Compound No. | $R^1$ | $A^2$ | $R^3$ | $R^6$ | Z | m | Physical property |
|---|---|---|---|---|---|---|---|
| 8-76 | Et | C—CF$_3$ | Ac | OCF$_2$CHF$_2$ | Me | 0 | |
| 8-77 | Et | C—CF$_3$ | Ac | OCF$_2$CHF$_2$ | Me | 1 | |
| 8-78 | Et | C—CF$_3$ | Ac | OCF$_2$CHF$_2$ | Me | 2 | |
| 8-79 | Et | C—CF$_3$ | H | OCF$_2$CHFCl | Me | 0 | |
| 8-80 | Et | C—CF$_3$ | H | OCF$_2$CHFCl | Me | 1 | |
| 8-81 | Et | C—CF$_3$ | H | OCF$_2$CHFCl | Me | 2 | |
| 8-82 | Et | C—CF$_3$ | Ac | OCF$_2$CHFCl | Me | 0 | |
| 8-83 | Et | C—CF$_3$ | Ac | OCF$_2$CHFCl | Me | 1 | |

TABLE 8-4-continued

| Compound No. | $R^1$ | $A^2$ | $R^3$ | $R^6$ | Z | m | Physical property |
|---|---|---|---|---|---|---|---|
| 8-84 | Et | C—$CF_3$ | Ac | $OCF_2CHFCl$ | Me | 2 | |
| 8-85 | Et | C—$CF_3$ | H | $OCF_2CHCl_2$ | Me | 0 | |
| 8-86 | Et | C—$CF_3$ | H | $OCF_2CHCl_2$ | Me | 1 | |
| 8-87 | Et | C—$CF_3$ | H | $OCF_2CHCl_2$ | Me | 2 | |
| 8-88 | Et | C—$CF_3$ | Ac | $OCF_2CHCl_2$ | Me | 0 | |
| 8-89 | Et | C—$CF_3$ | Ac | $OCF_2CHCl_2$ | Me | 1 | |
| 8-90 | Et | C—$CF_3$ | Ac | $OCF_2CHCl_2$ | Me | 2 | |
| 8-91 | Et | C—$CF_3$ | H | $OCF_2CF_3$ | Me | 0 | |
| 8-92 | Et | C—$CF_3$ | H | $OCF_2CF_3$ | Me | 1 | |
| 8-93 | Et | C—$CF_3$ | H | $OCF_2CF_3$ | Me | 2 | |
| 8-94 | Et | C—$CF_3$ | Ac | $OCF_2CF_3$ | Me | 0 | |
| 8-95 | Et | C—$CF_3$ | Ac | $OCF_2CF_3$ | Me | 1 | |
| 8-96 | Et | C—$CF_3$ | Ac | $OCF_2CF_3$ | Me | 2 | |
| 8-97 | Et | C—$CF_3$ | H | $OCF_2CFCl_2$ | Me | 0 | |
| 8-98 | Et | C—$CF_3$ | H | $OCF_2CFCl_2$ | Me | 1 | |
| 8-99 | Et | C—$CF_3$ | H | $OCF_2CFCl_2$ | Me | 2 | |
| 8-100 | Et | C—$CF_3$ | Ac | $OCF_2CFCl_2$ | Me | 0 | |

$R^4$, $R^5$ and $R^7$ each represent a hydrogen atom, and $A^1$, $A^3$ and $A^4$ each represent a CH group.

TABLE 8-5

| Compound No. | $R^1$ | $A^2$ | $R^3$ | $R^6$ | Z | m | Physical property |
|---|---|---|---|---|---|---|---|
| 8-101 | Et | C—$CF_3$ | Ac | $OCF_2CFCl_2$ | Me | 1 | |
| 8-102 | Et | C—$CF_3$ | Ac | $OCF_2CFCl_2$ | Me | 2 | |
| 8-103 | Et | C—$CF_3$ | H | $OCF_2CF_2Br$ | Me | 0 | |
| 8-104 | Et | C—$CF_3$ | H | $OCF_2CF_2Br$ | Me | 1 | |
| 8-105 | Et | C—$CF_3$ | H | $OCF_2CF_2Br$ | Me | 2 | |
| 8-106 | Et | C—$CF_3$ | Ac | $OCF_2CF_2Br$ | Me | 0 | |
| 8-107 | Et | C—$CF_3$ | Ac | $OCF_2CF_2Br$ | Me | 1 | |
| 8-108 | Et | C—$CF_3$ | Ac | $OCF_2CF_2Br$ | Me | 2 | |
| 8-109 | Et | C—$CF_3$ | H | $OCF_2CHOCF_3$ | Me | 0 | |
| 8-110 | Et | C—$CF_3$ | H | $OCF_2CHOCF_3$ | Me | 1 | |
| 8-111 | Et | C—$CF_3$ | H | $OCF_2CHOCF_3$ | Me | 2 | |
| 8-112 | Et | C—$CF_3$ | Ac | $OCF_2CHOCF_3$ | Me | 0 | |
| 8-113 | Et | C—$CF_3$ | Ac | $OCF_2CHOCF_3$ | Me | 1 | |
| 8-114 | Et | C—$CF_3$ | Ac | $OCF_2CHOCF_3$ | Me | 2 | |
| 8-115 | Et | C—$CF_3$ | H | Me | Me | 0 | |
| 8-116 | Et | C—$CF_3$ | H | Me | Me | 1 | |
| 8-117 | Et | C—$CF_3$ | H | Me | Me | 2 | |
| 8-118 | Et | C—$CF_3$ | Ac | Me | Me | 0 | |
| 8-119 | Et | C—$CF_3$ | Ac | Me | Me | 1 | |
| 8-120 | Et | C—$CF_3$ | Ac | Me | Me | 2 | |
| 8-121 | Et | C—$CF_3$ | H | Et | Me | 0 | |
| 8-122 | Et | C—$CF_3$ | H | Et | Me | 1 | |
| 8-123 | Et | C—$CF_3$ | H | Et | Me | 2 | |
| 8-124 | Et | C—$CF_3$ | Ac | Et | Me | 0 | |
| 8-125 | Et | C—$CF_3$ | Ac | Et | Me | 1 | |

$R^4$, $R^5$ and $R^7$ each represent a hydrogen atom, and $A^1$, $A^3$ and $A^4$ each represent a CH group.

TABLE 8-6

| Compound No. | $R^1$ | $A^2$ | $R^3$ | $R^6$ | Z | m | Physical property |
|---|---|---|---|---|---|---|---|
| 8-126 | Et | C—$CF_3$ | Ac | Et | Me | 2 | |
| 8-127 | Et | C—$CF_3$ | H | n-Pr | Me | 0 | |
| 8-128 | Et | C—$CF_3$ | H | n-Pr | Me | 1 | |
| 8-129 | Et | C—$CF_3$ | H | n-Pr | Me | 2 | |
| 8-130 | Et | C—$CF_3$ | Ac | n-Pr | Me | 0 | |
| 8-131 | Et | C—$CF_3$ | Ac | n-Pr | Me | 1 | |
| 8-132 | Et | C—$CF_3$ | Ac | n-Pr | Me | 2 | |
| 8-133 | Et | C—$CF_3$ | H | i-Pr | Me | 0 | |
| 8-134 | Et | C—$CF_3$ | H | i-Pr | Me | 1 | |
| 8-135 | Et | C—$CF_3$ | H | i-Pr | Me | 2 | |
| 8-136 | Et | C—$CF_3$ | Ac | i-Pr | Me | 0 | |
| 8-137 | Et | C—$CF_3$ | Ac | i-Pr | Me | 1 | |
| 8-138 | Et | C—$CF_3$ | Ac | i-Pr | Me | 2 | |
| 8-139 | Et | C—$CF_3$ | H | n-Bu | Me | 0 | |
| 8-140 | Et | C—$CF_3$ | H | n-Bu | Me | 1 | |
| 8-141 | Et | C—$CF_3$ | H | n-Bu | Me | 2 | |
| 8-142 | Et | C—$CF_3$ | Ac | n-Bu | Me | 0 | |
| 8-143 | Et | C—$CF_3$ | Ac | n-Bu | Me | 1 | |
| 8-144 | Et | C—$CF_3$ | Ac | n-Bu | Me | 2 | |
| 8-145 | Et | C—$CF_3$ | H | i-Bu | Me | 0 | |
| 8-146 | Et | C—$CF_3$ | H | i-Bu | Me | 1 | |
| 8-147 | Et | C—$CF_3$ | H | i-Bu | Me | 2 | |
| 8-148 | Et | C—$CF_3$ | Ac | i-Bu | Me | 0 | |
| 8-149 | Et | C—$CF_3$ | Ac | i-Bu | Me | 1 | |
| 8-150 | Et | C—$CF_3$ | Ac | i-Bu | Me | 2 | |

$R^4$, $R^5$ and $R^7$ each represent a hydrogen atom, and $A^1$, $A^3$ and $A^4$ each represent a CH group.

TABLE 8-7

| Compound No. | $R^1$ | $A^2$ | $R^3$ | $R^6$ | Z | m | Physical property |
|---|---|---|---|---|---|---|---|
| 8-151 | Et | C—$CF_3$ | H | s-Bu | Me | 0 | |
| 8-152 | Et | C—$CF_3$ | H | s-Bu | Me | 1 | |
| 8-153 | Et | C—$CF_3$ | H | s-Bu | Me | 2 | |
| 8-154 | Et | C—$CF_3$ | Ac | s-Bu | Me | 0 | |
| 8-155 | Et | C—$CF_3$ | Ac | s-Bu | Me | 1 | |
| 8-156 | Et | C—$CF_3$ | Ac | s-Bu | Me | 2 | |
| 8-157 | Et | C—$CF_3$ | H | t-Bu | Me | 0 | |
| 8-158 | Et | C—$CF_3$ | H | t-Bu | Me | 1 | |
| 8-159 | Et | C—$CF_3$ | H | t-Bu | Me | 2 | |
| 8-160 | Et | C—$CF_3$ | Ac | t-Bu | Me | 0 | |
| 8-161 | Et | C—$CF_3$ | Ac | t-Bu | Me | 1 | |
| 8-162 | Et | C—$CF_3$ | Ac | t-Bu | Me | 2 | |
| 8-163 | Et | C—$CF_3$ | H | c-Pr | Me | 0 | |
| 8-164 | Et | C—$CF_3$ | H | c-Pr | Me | 1 | |
| 8-165 | Et | C—$CF_3$ | H | c-Pr | Me | 2 | |
| 8-166 | Et | C—$CF_3$ | Ac | c-Pr | Me | 0 | |
| 8-167 | Et | C—$CF_3$ | Ac | c-Pr | Me | 1 | |
| 8-168 | Et | C—$CF_3$ | Ac | c-Pr | Me | 2 | |
| 8-169 | Et | C—$CF_3$ | H | $CH_2CF_3$ | Me | 0 | |
| 8-170 | Et | C—$CF_3$ | H | $CH_2CF_3$ | Me | 1 | |
| 8-171 | Et | C—$CF_3$ | H | $CH_2CF_3$ | Me | 2 | |
| 8-172 | Et | C—$CF_3$ | Ac | $CH_2CF_3$ | Me | 0 | |
| 8-173 | Et | C—$CF_3$ | Ac | $CH_2CF_3$ | Me | 1 | |
| 8-174 | Et | C—$CF_3$ | Ac | $CH_2CF_3$ | Me | 2 | |
| 8-175 | Et | C—$CF_3$ | H | $CF_3$ | Me | 0 | 134-135 |

$R^4$, $R^5$ and $R^7$ each represent a hydrogen atom, and $A^1$, $A^3$ and $A^4$ each represent a CH group.

TABLE 8-8

| Compound No. | $R^1$ | $A^2$ | $R^3$ | $R^6$ | Z | m | Physical property |
|---|---|---|---|---|---|---|---|
| 8-176 | Et | C—$CF_3$ | H | $CF_3$ | Me | 1 | |
| 8-177 | Et | C—$CF_3$ | H | $CF_3$ | Me | 2 | 200-201 |
| 8-178 | Et | C—$CF_3$ | Ac | $CF_3$ | Me | 0 | 87-88 |
| 8-179 | Et | C—$CF_3$ | Ac | $CF_3$ | Me | 1 | |
| 8-180 | Et | C—$CF_3$ | Ac | $CF_3$ | Me | 2 | 59-60 |
| 8-181 | Et | C—$CF_3$ | H | $CF_2CF_3$ | Me | 0 | |
| 8-182 | Et | C—$CF_3$ | H | $CF_2CF_3$ | Me | 1 | |
| 8-183 | Et | C—$CF_3$ | H | $CF_2CF_3$ | Me | 2 | |
| 8-184 | Et | C—$CF_3$ | Ac | $CF_2CF_3$ | Me | 0 | |
| 8-185 | Et | C—$CF_3$ | Ac | $CF_2CF_3$ | Me | 1 | |
| 8-186 | Et | C—$CF_3$ | Ac | $CF_2CF_3$ | Me | 2 | |
| 8-187 | Et | C—$CF_3$ | H | $C(Oi-Pr)(CF_3)_2$ | Me | 0 | |
| 8-188 | Et | C—$CF_3$ | H | $C(Oi-Pr)(CF_3)_2$ | Me | 1 | |
| 8-189 | Et | C—$CF_3$ | H | $C(Oi-Pr)(CF_3)_2$ | Me | 2 | |
| 8-190 | Et | C—$CF_3$ | Ac | $C(Oi-Pr)(CF_3)_2$ | Me | 0 | |
| 8-191 | Et | C—$CF_3$ | Ac | $C(Oi-Pr)(CF_3)_2$ | Me | 1 | |
| 8-192 | Et | C—$CF_3$ | Ac | $C(Oi-Pr)(CF_3)_2$ | Me | 2 | |
| 8-193 | Et | C—$CF_3$ | H | CN | Me | 0 | |

TABLE 8-8-continued

| Compound No. | $R^1$ | $A^2$ | $R^3$ | $R^6$ | Z | m | Physical property |
|---|---|---|---|---|---|---|---|
| 8-194 | Et | C—$CF_3$ | H | CN | Me | 1 | |
| 8-195 | Et | C—$CF_3$ | H | CN | Me | 2 | |
| 8-196 | Et | C—$CF_3$ | Ac | CN | Me | 0 | |
| 8-197 | Et | C—$CF_3$ | Ac | CN | Me | 1 | |
| 8-198 | Et | C—$CF_3$ | Ac | CN | Me | 2 | |
| 8-199 | Et | C—$CF_3$ | H | N—Me(n-$C_3F_7$) | Me | 0 | 122-125 |
| 8-200 | Et | C—$CF_3$ | H | N—Me(n-$C_3F_7$) | Me | 1 | |

$R^4$, $R^5$ and $R^7$ each represent a hydrogen atom, and $A^1$, $A^3$ and $A^4$ each represent a CH group.

TABLE 8-9

| Compound No. | $R^1$ | $A^2$ | $R^3$ | $R^6$ | Z | m | Physical property |
|---|---|---|---|---|---|---|---|
| 8-201 | Et | C—$CF_3$ | H | N—Me(n-$C_3F_7$) | Me | 2 | 72-82 |
| 8-202 | Et | C—$CF_3$ | H | SMe | Me | 0 | |
| 8-203 | Et | C—$CF_3$ | H | SMe | Me | 1 | |
| 8-204 | Et | C—$CF_3$ | H | SMe | Me | 2 | |
| 8-205 | Et | C—$CF_3$ | Ac | SMe | Me | 0 | |
| 8-206 | Et | C—$CF_3$ | Ac | SMe | Me | 1 | |
| 8-207 | Et | C—$CF_3$ | Ac | SMe | Me | 2 | |
| 8-208 | Et | C—$CF_3$ | H | SOMe | Me | 0 | |
| 8-209 | Et | C—$CF_3$ | H | SOMe | Me | 1 | |
| 8-210 | Et | C—$CF_3$ | H | SOMe | Me | 2 | |
| 8-211 | Et | C—$CF_3$ | Ac | SOMe | Me | 0 | |
| 8-212 | Et | C—$CF_3$ | Ac | SOMe | Me | 1 | |
| 8-213 | Et | C—$CF_3$ | Ac | SOMe | Me | 2 | |
| 8-214 | Et | C—$CF_3$ | H | $SO_2Me$ | Me | 0 | |
| 8-215 | Et | C—$CF_3$ | H | $SO_2Me$ | Me | 1 | |
| 8-216 | Et | C—$CF_3$ | H | $SO_2Me$ | Me | 2 | |
| 8-217 | Et | C—$CF_3$ | Ac | $SO_2Me$ | Me | 0 | |
| 8-218 | Et | C—$CF_3$ | Ac | $SO_2Me$ | Me | 1 | |
| 8-219 | Et | C—$CF_3$ | Ac | $SO_2Me$ | Me | 2 | |
| 8-220 | Et | C—$CF_3$ | H | SEt | Me | 0 | |
| 8-221 | Et | C—$CF_3$ | H | SEt | Me | 1 | |
| 8-222 | Et | C—$CF_3$ | H | SEt | Me | 2 | |
| 8-223 | Et | C—$CF_3$ | Ac | SEt | Me | 0 | |
| 8-224 | Et | C—$CF_3$ | Ac | SEt | Me | 1 | |
| 8-225 | Et | C—$CF_3$ | Ac | SEt | Me | 2 | |

$R^4$, $R^5$ and $R^7$ each represent a hydrogen atom, and $A^1$, $A^3$ and $A^4$ each represent a CH group.

TABLE 8-10

| Compound No. | $R^1$ | $A^2$ | $R^3$ | $R^6$ | Z | m | Physical property |
|---|---|---|---|---|---|---|---|
| 8-226 | Et | C—$CF_3$ | H | SOEt | Me | 0 | |
| 8-227 | Et | C—$CF_3$ | H | SOEt | Me | 1 | |
| 8-228 | Et | C—$CF_3$ | H | SOEt | Me | 2 | |
| 8-229 | Et | C—$CF_3$ | Ac | SOEt | Me | 0 | |
| 8-230 | Et | C—$CF_3$ | Ac | SOEt | Me | 1 | |
| 8-231 | Et | C—$CF_3$ | Ac | SOEt | Me | 2 | |
| 8-232 | Et | C—$CF_3$ | H | $SO_2Et$ | Me | 0 | |
| 8-233 | Et | C—$CF_3$ | H | $SO_2Et$ | Me | 1 | |
| 8-234 | Et | C—$CF_3$ | H | $SO_2Et$ | Me | 2 | |
| 8-235 | Et | C—$CF_3$ | Ac | $SO_2Et$ | Me | 0 | |
| 8-236 | Et | C—$CF_3$ | Ac | $SO_2Et$ | Me | 1 | |
| 8-237 | Et | C—$CF_3$ | Ac | $SO_2Et$ | Me | 2 | |
| 8-238 | Et | C—$CF_3$ | H | Sn-Pr | Me | 0 | |
| 8-239 | Et | C—$CF_3$ | H | Sn-Pr | Me | 1 | |
| 8-240 | Et | C—$CF_3$ | H | Sn-Pr | Me | 2 | |
| 8-241 | Et | C—$CF_3$ | Ac | Sn-Pr | Me | 0 | |
| 8-242 | Et | C—$CF_3$ | Ac | Sn-Pr | Me | 1 | |
| 8-243 | Et | C—$CF_3$ | Ac | Sn-Pr | Me | 2 | |
| 8-244 | Et | C—$CF_3$ | H | SO—n-Pr | Me | 0 | |
| 8-245 | Et | C—$CF_3$ | H | SO—n-Pr | Me | 1 | |
| 8-246 | Et | C—$CF_3$ | H | SO—n-Pr | Me | 2 | |
| 8-247 | Et | C—$CF_3$ | Ac | SO—n-Pr | Me | 0 | |
| 8-248 | Et | C—$CF_3$ | Ac | SO—n-Pr | Me | 1 | |
| 8-249 | Et | C—$CF_3$ | Ac | SO—n-Pr | Me | 2 | |
| 8-250 | Et | C—$CF_3$ | H | $SO_2$n-Pr | Me | 0 | |

$R^4$, $R^5$ and $R^7$ each represent a hydrogen atom, and $A^1$, $A^3$ and $A^4$ each represent a CH group.

TABLE 8-11

| Compound No. | $R^1$ | $A^2$ | $R^3$ | $R^6$ | Z | m | Physical property |
|---|---|---|---|---|---|---|---|
| 8-251 | Et | C—$CF_3$ | H | $SO_2$n-Pr | Me | 1 | |
| 8-252 | Et | C—$CF_3$ | H | $SO_2$n-Pr | Me | 2 | |
| 8-253 | Et | C—$CF_3$ | Ac | $SO_2$n-Pr | Me | 0 | |
| 8-254 | Et | C—$CF_3$ | Ac | $SO_2$n-Pr | Me | 1 | |
| 8-255 | Et | C—$CF_3$ | Ac | $SO_2$n-Pr | Me | 2 | |
| 8-256 | Et | C—$CF_3$ | H | Si-Pr | Me | 0 | |
| 8-257 | Et | C—$CF_3$ | H | Si-Pr | Me | 1 | |
| 8-258 | Et | C—$CF_3$ | H | Si-Pr | Me | 2 | |
| 8-259 | Et | C—$CF_3$ | Ac | Si-Pr | Me | 0 | |
| 8-260 | Et | C—$CF_3$ | Ac | Si-Pr | Me | 1 | |
| 8-261 | Et | C—$CF_3$ | Ac | Si-Pr | Me | 2 | |
| 8-262 | Et | C—$CF_3$ | H | SO—i-Pr | Me | 0 | |
| 8-263 | Et | C—$CF_3$ | H | SO—i-Pr | Me | 1 | |
| 8-264 | Et | C—$CF_3$ | H | SO—i-Pr | Me | 2 | |
| 8-265 | Et | C—$CF_3$ | Ac | SO—i-Pr | Me | 0 | |
| 8-266 | Et | C—$CF_3$ | Ac | SO—i-Pr | Me | 1 | |
| 8-267 | Et | C—$CF_3$ | Ac | SO—i-Pr | Me | 2 | |
| 8-268 | Et | C—$CF_3$ | H | $SO_2$i-Pr | Me | 0 | |
| 8-269 | Et | C—$CF_3$ | H | $SO_2$i-Pr | Me | 1 | |
| 8-270 | Et | C—$CF_3$ | H | $SO_2$i-Pr | Me | 2 | |
| 8-271 | Et | C—$CF_3$ | Ac | $SO_2$i-Pr | Me | 0 | |
| 8-272 | Et | C—$CF_3$ | Ac | $SO_2$i-Pr | Me | 1 | |
| 8-273 | Et | C—$CF_3$ | Ac | $SO_2$i-Pr | Me | 2 | |
| 8-274 | Et | C—$CF_3$ | H | Sn-Bu | Me | 0 | |
| 8-275 | Et | C—$CF_3$ | H | Sn-Bu | Me | 1 | |

$R^4$, $R^5$ and $R^7$ each represent a hydrogen atom, and $A^1$, $A^3$ and $A^4$ each represent a CH group.

TABLE 8-12

| Compound No. | $R^1$ | $A^2$ | $R^3$ | $R^6$ | Z | m | Physical property |
|---|---|---|---|---|---|---|---|
| 8-276 | Et | C—$CF_3$ | H | Sn-Bu | Me | 2 | |
| 8-277 | Et | C—$CF_3$ | Ac | Sn-Bu | Me | 0 | |
| 8-278 | Et | C—$CF_3$ | Ac | Sn-Bu | Me | 1 | |
| 8-279 | Et | C—$CF_3$ | Ac | Sn-Bu | Me | 2 | |
| 8-280 | Et | C—$CF_3$ | H | SO—n-Bu | Me | 0 | |
| 8-281 | Et | C—$CF_3$ | H | SO—n-Bu | Me | 1 | |
| 8-282 | Et | C—$CF_3$ | H | SO—n-Bu | Me | 2 | |
| 8-283 | Et | C—$CF_3$ | Ac | SO—n-Bu | Me | 0 | |
| 8-284 | Et | C—$CF_3$ | Ac | SO—n-Bu | Me | 1 | |
| 8-285 | Et | C—$CF_3$ | Ac | SO—n-Bu | Me | 2 | |
| 8-286 | Et | C—$CF_3$ | H | $SO_2$n-Bu | Me | 0 | |
| 8-287 | Et | C—$CF_3$ | H | $SO_2$n-Bu | Me | 1 | |
| 8-288 | Et | C—$CF_3$ | H | $SO_2$n-Bu | Me | 2 | |
| 8-289 | Et | C—$CF_3$ | Ac | $SO_2$n-Bu | Me | 0 | |
| 8-290 | Et | C—$CF_3$ | Ac | $SO_2$n-Bu | Me | 1 | |
| 8-291 | Et | C—$CF_3$ | Ac | $SO_2$n-Bu | Me | 2 | |
| 8-292 | Et | C—$CF_3$ | H | Si-Bu | Me | 0 | |
| 8-293 | Et | C—$CF_3$ | H | Si-Bu | Me | 1 | |
| 8-294 | Et | C—$CF_3$ | H | Si-Bu | Me | 2 | |
| 8-295 | Et | C—$CF_3$ | Ac | Si-Bu | Me | 0 | |
| 8-296 | Et | C—$CF_3$ | Ac | Si-Bu | Me | 1 | |
| 8-297 | Et | C—$CF_3$ | Ac | Si-Bu | Me | 2 | |
| 8-298 | Et | C—$CF_3$ | H | SO—i-Bu | Me | 0 | |
| 8-299 | Et | C—$CF_3$ | H | SO—i-Bu | Me | 1 | |
| 8-300 | Et | C—$CF_3$ | H | SO—i-Bu | Me | 2 | |

$R^4$, $R^5$ and $R^7$ each represent a hydrogen atom, and $A^1$, $A^3$ and $A^4$ each represent a CH group.

TABLE 8-13

| Compound No. | R¹ | A² | R³ | R⁶ | Z | m | Physical property |
|---|---|---|---|---|---|---|---|
| 8-301 | Et | C—CF₃ | Ac | SO—i-Bu | Me | 0 | |
| 8-302 | Et | C—CF₃ | Ac | SO—i-Bu | Me | 1 | |
| 8-303 | Et | C—CF₃ | Ac | SO—i-Bu | Me | 2 | |
| 8-304 | Et | C—CF₃ | H | SO₂i-Bu | Me | 0 | |
| 8-305 | Et | C—CF₃ | H | SO₂i-Bu | Me | 1 | |
| 8-306 | Et | C—CF₃ | H | SO₂i-Bu | Me | 2 | |
| 8-307 | Et | C—CF₃ | Ac | SO₂i-Bu | Me | 0 | |
| 8-308 | Et | C—CF₃ | Ac | SO₂i-Bu | Me | 1 | |
| 8-309 | Et | C—CF₃ | Ac | SO₂i-Bu | Me | 2 | |
| 8-310 | Et | C—CF₃ | H | Ss-Bu | Me | 0 | |
| 8-311 | Et | C—CF₃ | H | Ss-Bu | Me | 1 | |
| 8-312 | Et | C—CF₃ | H | Ss-Bu | Me | 2 | |
| 8-313 | Et | C—CF₃ | Ac | Ss-Bu | Me | 0 | |
| 8-314 | Et | C—CF₃ | Ac | Ss-Bu | Me | 1 | |
| 8-315 | Et | C—CF₃ | Ac | Ss-Bu | Me | 2 | |
| 8-316 | Et | C—CF₃ | H | SO—s-Bu | Me | 0 | |
| 8-317 | Et | C—CF₃ | H | SO—s-Bu | Me | 1 | |
| 8-318 | Et | C—CF₃ | H | SO—s-Bu | Me | 2 | |
| 8-319 | Et | C—CF₃ | Ac | SO—s-Bu | Me | 0 | |
| 8-320 | Et | C—CF₃ | Ac | SO—s-Bu | Me | 1 | |
| 8-321 | Et | C—CF₃ | Ac | SO—s-Bu | Me | 2 | |
| 8-322 | Et | C—CF₃ | H | SO₂s-Bu | Me | 0 | |
| 8-323 | Et | C—CF₃ | H | SO₂s-Bu | Me | 1 | |
| 8-324 | Et | C—CF₃ | H | SO₂s-Bu | Me | 2 | |
| 8-325 | Et | C—CF₃ | Ac | SO₂s-Bu | Me | 0 | |

$R^4$, $R^5$ and $R^7$ each represent a hydrogen atom, and $A^1$, $A^3$ and $A^4$ each represent a CH group.

TABLE 8-14

| Compound No. | R¹ | A² | R³ | R⁶ | Z | m | Physical property |
|---|---|---|---|---|---|---|---|
| 8-326 | Et | C—CF₃ | Ac | SO₂s-Bu | Me | 1 | |
| 8-327 | Et | C—CF₃ | Ac | SO₂s-Bu | Me | 2 | |
| 8-328 | Et | C—CF₃ | H | St-Bu | Me | 0 | |
| 8-329 | Et | C—CF₃ | H | St-Bu | Me | 1 | |
| 8-330 | Et | C—CF₃ | H | St-Bu | Me | 2 | |
| 8-331 | Et | C—CF₃ | Ac | St-Bu | Me | 0 | |
| 8-332 | Et | C—CF₃ | Ac | St-Bu | Me | 1 | |
| 8-333 | Et | C—CF₃ | Ac | St-Bu | Me | 2 | |
| 8-334 | Et | C—CF₃ | H | SO—t-Bu | Me | 0 | |
| 8-335 | Et | C—CF₃ | H | SO—t-Bu | Me | 1 | |
| 8-336 | Et | C—CF₃ | H | SO—t-Bu | Me | 2 | |
| 8-337 | Et | C—CF₃ | Ac | SO—t-Bu | Me | 0 | |
| 8-338 | Et | C—CF₃ | Ac | SO—t-Bu | Me | 1 | |
| 8-339 | Et | C—CF₃ | Ac | SO—t-Bu | Me | 2 | |
| 8-340 | Et | C—CF₃ | H | SO₂t-Bu | Me | 0 | |
| 8-341 | Et | C—CF₃ | H | SO₂t-Bu | Me | 1 | |
| 8-342 | Et | C—CF₃ | H | SO₂t-Bu | Me | 2 | |
| 8-343 | Et | C—CF₃ | Ac | SO₂t-Bu | Me | 0 | |
| 8-344 | Et | C—CF₃ | Ac | SO₂t-Bu | Me | 1 | |
| 8-345 | Et | C—CF₃ | Ac | SO₂t-Bu | Me | 2 | |
| 8-346 | Et | C—CF₃ | H | SCF₃ | Me | 0 | |
| 8-347 | Et | C—CF₃ | H | SCF₃ | Me | 1 | |
| 8-348 | Et | C—CF₃ | H | SCF₃ | Me | 2 | NMR |
| 8-349 | Et | C—CF₃ | Ac | SCF₃ | Me | 0 | |
| 8-350 | Et | C—CF₃ | Ac | SCF₃ | Me | 1 | |

$R^4$, $R^5$ and $R^7$ each represent a hydrogen atom, and $A^1$, $A^3$ and $A^4$ each represent a CH group.

TABLE 8-15

| Compound No. | R¹ | A² | R³ | R⁶ | Z | m | Physical property |
|---|---|---|---|---|---|---|---|
| 8-351 | Et | C—CF₃ | Ac | SCF₃ | Me | 2 | |
| 8-352 | Et | C—CF₃ | H | SOCF₃ | Me | 0 | |
| 8-353 | Et | C—CF₃ | H | SOCF₃ | Me | 1 | |
| 8-354 | Et | C—CF₃ | H | SOCF₃ | Me | 2 | |
| 8-355 | Et | C—CF₃ | Ac | SOCF₃ | Me | 0 | |

TABLE 8-15-continued

| Compound No. | R¹ | A² | R³ | R⁶ | Z | m | Physical property |
|---|---|---|---|---|---|---|---|
| 8-356 | Et | C—CF₃ | Ac | SOCF₃ | Me | 1 | |
| 8-357 | Et | C—CF₃ | Ac | SOCF₃ | Me | 2 | |
| 8-358 | Et | C—CF₃ | H | SO₂CF₃ | Me | 0 | |
| 8-359 | Et | C—CF₃ | H | SO₂CF₃ | Me | 1 | |
| 8-360 | Et | C—CF₃ | H | SO₂CF₃ | Me | 2 | |
| 8-361 | Et | C—CF₃ | Ac | SO₂CF₃ | Me | 0 | |
| 8-362 | Et | C—CF₃ | Ac | SO₂CF₃ | Me | 1 | |
| 8-363 | Et | C—CF₃ | Ac | SO₂CF₃ | Me | 2 | |
| 8-364 | Et | C—CF₃ | Ac | Cl | Me | 0 | |
| 8-365 | Et | C—CF₃ | Ac | Cl | Me | 1 | |
| 8-366 | Et | C—CF₃ | Ac | Cl | Me | 2 | |
| 8-367 | Et | C—CF₃ | H | Br | Me | 0 | |
| 8-368 | Et | C—CF₃ | H | Br | Me | 1 | |
| 8-369 | Et | C—CF₃ | H | Br | Me | 2 | |
| 8-370 | Et | C—CF₃ | Ac | Br | Me | 0 | |
| 8-371 | Et | C—CF₃ | Ac | Br | Me | 1 | |
| 8-372 | Et | C—CF₃ | Ac | Br | Me | 2 | |
| 8-373 | Et | C—CF₃ | Ac | I | Me | 0 | |
| 8-374 | Et | C—CF₃ | Ac | I | Me | 1 | |
| 8-375 | Et | C—CF₃ | Ac | I | Me | 2 | |

$R^4$, $R^5$ and $R^7$ each represent a hydrogen atom, and $A^1$, $A^3$ and $A^4$ each represent a CH group.

TABLE 8-16

| Compound No. | R¹ | A² | R³ | R⁶ | Z | m | Physical property |
|---|---|---|---|---|---|---|---|
| 8-376 | Et | C—CF₃ | H | NO₂ | Me | 0 | |
| 8-377 | Et | C—CF₃ | H | NO₂ | Me | 1 | |
| 8-378 | Et | C—CF₃ | H | NO₂ | Me | 2 | |
| 8-379 | Et | C—CF₃ | Ac | NO₂ | Me | 0 | |
| 8-380 | Et | C—CF₃ | Ac | NO₂ | Me | 1 | |
| 8-381 | Et | C—CF₃ | Ac | NO₂ | Me | 2 | |

$R^4$, $R^5$ and $R^7$ each represent a hydrogen atom, and $A^1$, $A^3$ and $A^4$ each represent a CH group.

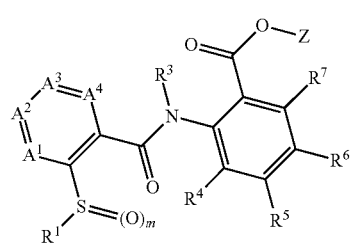

(1)

TABLE 9-1

| Compound No. | $R^1$ | $R^3$ | $A^2$ | $A^4$ | $R^6$ | Z | m | Physical property |
|---|---|---|---|---|---|---|---|---|
| 9-1 | Et | H | C—Ph | C—H | $CF(CF_3)_2$ | Me | 0 | 209-210 |
| 9-2 | Et | H | C—Ph | C—H | $CF(CF_3)_2$ | Me | 1 | |
| 9-3 | Et | H | C—Ph | C—H | $CF(CF_3)_2$ | Me | 2 | 195-196 |
| 9-4 | Et | Me | C—Ph | C—H | $CF(CF_3)_2$ | Me | 0 | 1.3647 (25.2° C.) |
| 9-5 | Et | Me | C—Ph | C—H | $CF(CF_3)_2$ | Me | 1 | |
| 9-6 | Et | Me | C—Ph | C—H | $CF(CF_3)_2$ | Me | 2 | |
| 9-7 | Et | Ac | C—Ph | C—H | $CF(CF_3)_2$ | Me | 0 | |
| 9-8 | Et | Ac | C—Ph | C—H | $CF(CF_3)_2$ | Me | 1 | |
| 9-9 | Et | Ac | C—Ph | C—H | $CF(CF_3)_2$ | Me | 2 | |
| 9-10 | Et | H | C-(2-$CF_3$—Ph) | C—H | $CF(CF_3)_2$ | Me | 0 | 150-151 |
| 9-11 | Et | H | C-(2-$CF_3$—Ph) | C—H | $CF(CF_3)_2$ | Me | 1 | 93-95 |
| 9-12 | Et | H | C-(2-$CF_3$—Ph) | C—H | $CF(CF_3)_2$ | Me | 2 | 158-159 |
| 9-13 | Et | Me | C-(2-$CF_3$—Ph) | C—H | $CF(CF_3)_2$ | Me | 0 | 1.3301 (25.1° C.) |
| 9-14 | Et | Me | C-(2-$CF_3$—Ph) | C—H | $CF(CF_3)_2$ | Me | 1 | |
| 9-15 | Et | Me | C-(2-$CF_3$—Ph) | C—H | $CF(CF_3)_2$ | Me | 2 | |
| 9-16 | Et | Ac | C-(2-$CF_3$—Ph) | C—H | $CF(CF_3)_2$ | Me | 0 | |
| 9-17 | Et | Ac | C-(2-$CF_3$—Ph) | C—H | $CF(CF_3)_2$ | Me | 1 | |
| 9-18 | Et | Ac | C-(2-$CF_3$—Ph) | C—H | $CF(CF_3)_2$ | Me | 2 | |
| 9-19 | Et | H | C-(3-$CF_3$—Ph) | C—H | $CF(CF_3)_2$ | Me | 0 | 176-179 |
| 9-20 | Et | H | C-(3-$CF_3$—Ph) | C—H | $CF(CF_3)_2$ | Me | 1 | 91-94 |
| 9-21 | Et | H | C-(3-$CF_3$—Ph) | C—H | $CF(CF_3)_2$ | Me | 2 | 192-193 |
| 9-22 | Et | Ac | C-(3-$CF_3$—Ph) | C—H | $CF(CF_3)_2$ | Me | 0 | |
| 9-23 | Et | Ac | C-(3-$CF_3$—Ph) | C—H | $CF(CF_3)_2$ | Me | 1 | |
| 9-24 | Et | Ac | C-(3-$CF_3$—Ph) | C—H | $CF(CF_3)_2$ | Me | 2 | |
| 9-25 | Et | H | C-(4-$CF_3$—Ph) | C—H | $CF(CF_3)_2$ | Me | 0 | 129-130 |

$R^4$, $R^5$ and $R^7$ each represent a hydrogen atom, and $A^1$ and $A^3$ each represent a CH group.

TABLE 9-2

| Compound No. | $R^1$ | $R^3$ | $A^2$ | $A^4$ | $R^6$ | Z | m | Physical property |
|---|---|---|---|---|---|---|---|---|
| 9-26 | Et | H | C-(4-$CF_3$—Ph) | C—H | $CF(CF_3)_2$ | Me | 1 | 170-171 |
| 9-27 | Et | H | C-(4-$CF_3$—Ph) | C—H | $CF(CF_3)_2$ | Me | 2 | 168-170 |
| 9-28 | Et | Ac | C-(4-$CF_3$—Ph) | C—H | $CF(CF_3)_2$ | Me | 0 | |
| 9-29 | Et | Ac | C-(4-$CF_3$—Ph) | C—H | $CF(CF_3)_2$ | Me | 1 | |
| 9-30 | Et | Ac | C-(4-$CF_3$—Ph) | C—H | $CF(CF_3)_2$ | Me | 2 | |
| 9-31 | Et | H | C-(4-$CF_3$—Ph) | C—H | $CF(CF_3)_2$ | Me | 0 | |
| 9-32 | Et | H | C—I | C—H | $CF(CF_3)_2$ | Me | 0 | 115-116 |
| 9-33 | Et | H | C—I | C—H | $CF(CF_3)_2$ | Me | 1 | |
| 9-34 | Et | H | C—I | C—H | $CF(CF_3)_2$ | Me | 2 | |
| 9-35 | Et | Ac | C—I | C—H | $CF(CF_3)_2$ | Me | 0 | |
| 9-36 | Et | Ac | C—I | C—H | $CF(CF_3)_2$ | Me | 1 | |
| 9-37 | Et | Ac | C—I | C—H | $CF(CF_3)_2$ | Me | 2 | |
| 9-38 | Et | H | C—OMe | C—H | $CF(CF_3)_2$ | Me | 0 | |
| 9-39 | Et | H | C—OMe | C—H | $CF(CF_3)_2$ | Me | 1 | |
| 9-40 | Et | H | C—OMe | C—H | $CF(CF_3)_2$ | Me | 2 | 119-121 |
| 9-41 | Et | Ac | C—OMe | C—H | $CF(CF_3)_2$ | Me | 0 | |
| 9-42 | Et | Ac | C—OMe | C—H | $CF(CF_3)_2$ | Me | 1 | |
| 9-43 | Et | Ac | C—OMe | C—H | $CF(CF_3)_2$ | Me | 2 | |
| 9-44 | Et | H | C—OEt | C—H | $CF(CF_3)_2$ | Me | 0 | |
| 9-45 | Et | H | C—OEt | C—H | $CF(CF_3)_2$ | Me | 1 | |
| 9-46 | Et | H | C—OEt | C—H | $CF(CF_3)_2$ | Me | 2 | |
| 9-47 | Et | Ac | C—OEt | C—H | $CF(CF_3)_2$ | Me | 0 | |
| 9-48 | Et | Ac | C—OEt | C—H | $CF(CF_3)_2$ | Me | 1 | |
| 9-49 | Et | Ac | C—OEt | C—H | $CF(CF_3)_2$ | Me | 2 | |
| 9-50 | Et | H | C—On-Pr | C—H | $CF(CF_3)_2$ | Me | 0 | |

$R^4$, $R^5$ and $R^7$ each represent a hydrogen atom, and $A^1$ and $A^3$ each represent a CH group.

TABLE 9-3

| Compound No. | $R^1$ | $R^3$ | $A^2$ | $A^4$ | $R^6$ | Z | m | Physical property |
|---|---|---|---|---|---|---|---|---|
| 9-51 | Et | H | C—On-Pr | C—H | $CF(CF_3)_2$ | Me | 1 | |
| 9-52 | Et | H | C—On-Pr | C—H | $CF(CF_3)_2$ | Me | 2 | |
| 9-53 | Et | Ac | C—On-Pr | C—H | $CF(CF_3)_2$ | Me | 0 | |
| 9-54 | Et | Ac | C—On-Pr | C—H | $CF(CF_3)_2$ | Me | 1 | |
| 9-55 | Et | Ac | C—On-Pr | C—H | $CF(CF_3)_2$ | Me | 2 | |
| 9-56 | Et | H | C—Oi-Pr | C—H | $CF(CF_3)_2$ | Me | 0 | |

TABLE 9-3-continued

| Compound No. | R¹ | R³ | A² | A⁴ | R⁶ | Z | m | Physical property |
|---|---|---|---|---|---|---|---|---|
| 9-57 | Et | H | C—Oi-Pr | C—H | $CF(CF_3)_2$ | Me | 1 | |
| 9-58 | Et | H | C—Oi-Pr | C—H | $CF(CF_3)_2$ | Me | 2 | 164-165 |
| 9-59 | Et | Ac | C—Oi-Pr | C—H | $CF(CF_3)_2$ | Me | 0 | |
| 9-60 | Et | Ac | C—Oi-Pr | C—H | $CF(CF_3)_2$ | Me | 1 | |
| 9-61 | Et | Ac | C—Oi-Pr | C—H | $CF(CF_3)_2$ | Me | 2 | 147-149 |
| 9-62 | Et | H | C—On-Bu | C—H | $CF(CF_3)_2$ | Me | 0 | |
| 9-63 | Et | H | C—On-Bu | C—H | $CF(CF_3)_2$ | Me | 1 | |
| 9-64 | Et | H | C—On-Bu | C—H | $CF(CF_3)_2$ | Me | 2 | |
| 9-65 | Et | Ac | C—On-Bu | C—H | $CF(CF_3)_2$ | Me | 0 | |
| 9-66 | Et | Ac | C—On-Bu | C—H | $CF(CF_3)_2$ | Me | 1 | |
| 9-67 | Et | Ac | C—On-Bu | C—H | $CF(CF_3)_2$ | Me | 2 | |
| 9-68 | Et | H | C—Oi-Bu | C—H | $CF(CF_3)_2$ | Me | 0 | |
| 9-69 | Et | H | C—Oi-Bu | C—H | $CF(CF_3)_2$ | Me | 1 | |
| 9-70 | Et | H | C—Oi-Bu | C—H | $CF(CF_3)_2$ | Me | 2 | |
| 9-71 | Et | Ac | C—Oi-Bu | C—H | $CF(CF_3)_2$ | Me | 0 | |
| 9-72 | Et | Ac | C—Oi-Bu | C—H | $CF(CF_3)_2$ | Me | 1 | |
| 9-73 | Et | Ac | C—Oi-Bu | C—H | $CF(CF_3)_2$ | Me | 2 | |
| 9-74 | Et | H | C—Os-Bu | C—H | $CF(CF_3)_2$ | Me | 0 | |
| 9-75 | Et | H | C—Os-Bu | C—H | $CF(CF_3)_2$ | Me | 1 | |

$R^4$, $R^5$ and $R^7$ each represent a hydrogen atom, and $A^1$ and $A^3$ each represent a CH group.

TABLE 9-4

| Compound No. | R¹ | R³ | A² | A⁴ | R⁶ | Z | m | Physical property |
|---|---|---|---|---|---|---|---|---|
| 9-76 | Et | H | C—Os-Bu | C—H | $CF(CF_3)_2$ | Me | 2 | |
| 9-77 | Et | Ac | C—Os-Bu | C—H | $CF(CF_3)_2$ | Me | 0 | |
| 9-78 | Et | Ac | C—Os-Bu | C—H | $CF(CF_3)_2$ | Me | 1 | |
| 9-79 | Et | Ac | C—Os-Bu | C—H | $CF(CF_3)_2$ | Me | 2 | |
| 9-80 | Et | H | C—Ot-Bu | C—H | $CF(CF_3)_2$ | Me | 0 | |
| 9-81 | Et | H | C—Ot-Bu | C—H | $CF(CF_3)_2$ | Me | 1 | |
| 9-82 | Et | H | C—Ot-Bu | C—H | $CF(CF_3)_2$ | Me | 2 | |
| 9-83 | Et | Ac | C—Ot-Bu | C—H | $CF(CF_3)_2$ | Me | 0 | |
| 9-84 | Et | Ac | C—Ot-Bu | C—H | $CF(CF_3)_2$ | Me | 1 | |
| 9-85 | Et | Ac | C—Ot-Bu | C—H | $CF(CF_3)_2$ | Me | 2 | |
| 9-86 | Et | H | C—OPh | C—H | $CF(CF_3)_2$ | Me | 0 | |
| 9-87 | Et | H | C—OPh | C—H | $CF(CF_3)_2$ | Me | 1 | |
| 9-88 | Et | H | C—OPh | C—H | $CF(CF_3)_2$ | Me | 2 | |
| 9-89 | Et | Ac | C—OPh | C—H | $CF(CF_3)_2$ | Me | 0 | |
| 9-90 | Et | Ac | C—OPh | C—H | $CF(CF_3)_2$ | Me | 1 | |
| 9-91 | Et | Ac | C—OPh | C—H | $CF(CF_3)_2$ | Me | 2 | |
| 9-92 | Et | H | C—Me | C—H | $CF(CF_3)_2$ | Me | 0 | |

TABLE 9-4-continued

| Compound No. | R¹ | R³ | A² | A⁴ | R⁶ | Z | m | Physical property |
|---|---|---|---|---|---|---|---|---|
| 9-93 | Et | H | C—Me | C—H | $CF(CF_3)_2$ | Me | 1 | |
| 9-94 | Et | H | C—Me | C—H | $CF(CF_3)_2$ | Me | 2 | |
| 9-95 | Et | Ac | C—Me | C—H | $CF(CF_3)_2$ | Me | 0 | |
| 9-96 | Et | Ac | C—Me | C—H | $CF(CF_3)_2$ | Me | 1 | |
| 9-97 | Et | Ac | C—Me | C—H | $CF(CF_3)_2$ | Me | 2 | |
| 9-98 | Et | H | C—Et | C—H | $CF(CF_3)_2$ | Me | 0 | |
| 9-99 | Et | H | C—Et | C—H | $CF(CF_3)_2$ | Me | 1 | |
| 9-100 | Et | H | C—Et | C—H | $CF(CF_3)_2$ | Me | 2 | |

$R^4$, $R^5$ and $R^7$ each represent a hydrogen atom, and $A^1$ and $A^3$ each represent a CH group.

TABLE 9-5

| Compound No. | R¹ | R³ | A² | A⁴ | R⁶ | Z | m | Physical property |
|---|---|---|---|---|---|---|---|---|
| 9-101 | Et | Ac | C—Et | C—H | $CF(CF_3)_2$ | Me | 0 | |
| 9-102 | Et | Ac | C—Et | C—H | $CF(CF_3)_2$ | Me | 1 | |
| 9-103 | Et | Ac | C—Et | C—H | $CF(CF_3)_2$ | Me | 2 | |
| 9-104 | Et | H | C—n-Pr | C—H | $CF(CF_3)_2$ | Me | 0 | |
| 9-105 | Et | H | C—n-Pr | C—H | $CF(CF_3)_2$ | Me | 1 | |
| 9-106 | Et | H | C—n-Pr | C—H | $CF(CF_3)_2$ | Me | 2 | |
| 9-107 | Et | Ac | C—n-Pr | C—H | $CF(CF_3)_2$ | Me | 0 | |
| 9-108 | Et | Ac | C—n-Pr | C—H | $CF(CF_3)_2$ | Me | 1 | |
| 9-109 | Et | Ac | C—n-Pr | C—H | $CF(CF_3)_2$ | Me | 2 | |
| 9-110 | Et | H | C—i-Pr | C—H | $CF(CF_3)_2$ | Me | 0 | |
| 9-111 | Et | H | C—i-Pr | C—H | $CF(CF_3)_2$ | Me | 1 | |
| 9-112 | Et | H | C—i-Pr | C—H | $CF(CF_3)_2$ | Me | 2 | |
| 9-113 | Et | Ac | C—i-Pr | C—H | $CF(CF_3)_2$ | Me | 0 | |
| 9-114 | Et | Ac | C—i-Pr | C—H | $CF(CF_3)_2$ | Me | 1 | |
| 9-115 | Et | Ac | C—i-Pr | C—H | $CF(CF_3)_2$ | Me | 2 | |
| 9-116 | Et | H | C—n-Bu | C—H | $CF(CF_3)_2$ | Me | 0 | |
| 9-117 | Et | H | C—n-Bu | C—H | $CF(CF_3)_2$ | Me | 1 | |
| 9-118 | Et | H | C—n-Bu | C—H | $CF(CF_3)_2$ | Me | 2 | |
| 9-119 | Et | Ac | C—n-Bu | C—H | $CF(CF_3)_2$ | Me | 0 | |
| 9-120 | Et | Ac | C—n-Bu | C—H | $CF(CF_3)_2$ | Me | 1 | |
| 9-121 | Et | Ac | C—n-Bu | C—H | $CF(CF_3)_2$ | Me | 2 | |
| 9-122 | Et | H | C—i-Bu | C—H | $CF(CF_3)_2$ | Me | 0 | |
| 9-123 | Et | H | C—i-Bu | C—H | $CF(CF_3)_2$ | Me | 1 | |
| 9-124 | Et | H | C—i-Bu | C—H | $CF(CF_3)_2$ | Me | 2 | |
| 9-125 | Et | Ac | C—i-Bu | C—H | $CF(CF_3)_2$ | Me | 0 | |

$R^4$, $R^5$ and $R^7$ each represent a hydrogen atom, and $A^1$ and $A^3$ each represent a CH group.

TABLE 9-6

| Compound No. | R¹ | R³ | A² | A⁴ | R⁶ | Z | m | Physical property |
|---|---|---|---|---|---|---|---|---|
| 9-126 | Et | Ac | C—i-Bu | C—H | $CF(CF_3)_2$ | Me | 1 | |
| 9-127 | Et | Ac | C—i-Bu | C—H | $CF(CF_3)_2$ | Me | 2 | |
| 9-128 | Et | H | C—s-Bu | C—H | $CF(CF_3)_2$ | Me | 0 | |
| 9-129 | Et | H | C—s-Bu | C—H | $CF(CF_3)_2$ | Me | 1 | |
| 9-130 | Et | H | C—s-Bu | C—H | $CF(CF_3)_2$ | Me | 2 | |
| 9-131 | Et | Ac | C—s-Bu | C—H | $CF(CF_3)_2$ | Me | 0 | |
| 9-132 | Et | Ac | C—s-Bu | C—H | $CF(CF_3)_2$ | Me | 1 | |
| 9-133 | Et | Ac | C—s-Bu | C—H | $CF(CF_3)_2$ | Me | 2 | |
| 9-134 | Et | H | C—t-Bu | C—H | $CF(CF_3)_2$ | Me | 0 | |
| 9-135 | Et | H | C—t-Bu | C—H | $CF(CF_3)_2$ | Me | 1 | |
| 9-136 | Et | H | C—t-Bu | C—H | $CF(CF_3)_2$ | Me | 2 | |
| 9-137 | Et | Ac | C—t-Bu | C—H | $CF(CF_3)_2$ | Me | 0 | |
| 9-138 | Et | Ac | C—t-Bu | C—H | $CF(CF_3)_2$ | Me | 1 | |
| 9-139 | Et | Ac | C—t-Bu | C—H | $CF(CF_3)_2$ | Me | 2 | |
| 9-140 | Et | H | C—c-Pr | C—H | $CF(CF_3)_2$ | Me | 0 | 72-75 |
| 9-141 | Et | H | C—c-Pr | C—H | $CF(CF_3)_2$ | Me | 1 | 100-104 |
| 9-142 | Et | H | C—c-Pr | C—H | $CF(CF_3)_2$ | Me | 2 | 1.3248 (24.5° C.) |
| 9-143 | Et | Ac | C—c-Pr | C—H | $CF(CF_3)_2$ | Me | 0 | |
| 9-144 | Et | Ac | C—c-Pr | C—H | $CF(CF_3)_2$ | Me | 1 | |
| 9-145 | Et | Ac | C—c-Pr | C—H | $CF(CF_3)_2$ | Me | 2 | |
| 9-146 | Et | H | C—SMe | C—H | $CF(CF_3)_2$ | Me | 0 | |
| 9-147 | Et | H | C—SMe | C—H | $CF(CF_3)_2$ | Me | 1 | |

TABLE 9-6-continued

| Compound No. | R¹ | R³ | A² | A⁴ | R⁶ | Z | m | Physical property |
|---|---|---|---|---|---|---|---|---|
| 9-148 | Et | H | C—SMe | C—H | $CF(CF_3)_2$ | Me | 2 | |
| 9-149 | Et | Ac | C—SMe | C—H | $CF(CF_3)_2$ | Me | 0 | |
| 9-150 | Et | Ac | C—SMe | C—H | $CF(CF_3)_2$ | Me | 1 | |

$R^4$, $R^5$ and $R^7$ each represent a hydrogen atom, and $A^1$ and $A^3$ each represent a CH group.

TABLE 9-7

| Compound No. | R¹ | R³ | A² | A⁴ | R⁶ | Z | m | Physical property |
|---|---|---|---|---|---|---|---|---|
| 9-151 | Et | Ac | C—SMe | C—H | $CF(CF_3)_2$ | Me | 2 | |
| 9-152 | Et | H | C—SOMe | C—H | $CF(CF_3)_2$ | Me | 0 | |
| 9-153 | Et | H | C—SOMe | C—H | $CF(CF_3)_2$ | Me | 1 | |
| 9-154 | Et | H | C—SOMe | C—H | $CF(CF_3)_2$ | Me | 2 | |
| 9-155 | Et | Ac | C—SOMe | C—H | $CF(CF_3)_2$ | Me | 0 | |
| 9-156 | Et | Ac | C—SOMe | C—H | $CF(CF_3)_2$ | Me | 1 | |
| 9-157 | Et | Ac | C—SOMe | C—H | $CF(CF_3)_2$ | Me | 2 | |
| 9-158 | Et | H | C—SO₂Me | C—H | $CF(CF_3)_2$ | Me | 0 | |
| 9-159 | Et | H | C—SO₂Me | C—H | $CF(CF_3)_2$ | Me | 1 | |
| 9-160 | Et | H | C—SO₂Me | C—H | $CF(CF_3)_2$ | Me | 2 | |
| 9-161 | Et | Ac | C—SO₂Me | C—H | $CF(CF_3)_2$ | Me | 0 | |
| 9-162 | Et | Ac | C—SO₂Me | C—H | $CF(CF_3)_2$ | Me | 1 | |
| 9-163 | Et | Ac | C—SO₂Me | C—H | $CF(CF_3)_2$ | Me | 2 | |
| 9-164 | Et | H | C—SEt | C—H | $CF(CF_3)_2$ | Me | 0 | |
| 9-165 | Et | H | C—SEt | C—H | $CF(CF_3)_2$ | Me | 1 | |
| 9-166 | Et | H | C—SEt | C—H | $CF(CF_3)_2$ | Me | 2 | |
| 9-167 | Et | Ac | C—SEt | C—H | $CF(CF_3)_2$ | Me | 0 | |
| 9-168 | Et | Ac | C—SEt | C—H | $CF(CF_3)_2$ | Me | 1 | |
| 9-169 | Et | Ac | C—SEt | C—H | $CF(CF_3)_2$ | Me | 2 | |
| 9-170 | Et | H | C—SOEt | C—H | $CF(CF_3)_2$ | Me | 0 | |
| 9-171 | Et | H | C—SOEt | C—H | $CF(CF_3)_2$ | Me | 1 | |
| 9-172 | Et | H | C—SOEt | C—H | $CF(CF_3)_2$ | Me | 2 | |
| 9-173 | Et | Ac | C—SOEt | C—H | $CF(CF_3)_2$ | Me | 0 | |
| 9-174 | Et | Ac | C—SOEt | C—H | $CF(CF_3)_2$ | Me | 1 | |
| 9-175 | Et | Ac | C—SOEt | C—H | $CF(CF_3)_2$ | Me | 2 | |

$R^4$, $R^5$ and $R^7$ each represent a hydrogen atom, and $A^1$ and $A^3$ each represent a CH group.

TABLE 9-8

| Compound No. | R¹ | R³ | A² | A⁴ | R⁶ | Z | m | Physical property |
|---|---|---|---|---|---|---|---|---|
| 9-176 | Et | H | C—SO₂Et | C—H | $CF(CF_3)_2$ | Me | 0 | |
| 9-177 | Et | H | C—SO₂Et | C—H | $CF(CF_3)_2$ | Me | 1 | |
| 9-178 | Et | H | C—SO₂Et | C—H | $CF(CF_3)_2$ | Me | 2 | |
| 9-179 | Et | Ac | C—SO₂Et | C—H | $CF(CF_3)_2$ | Me | 0 | |
| 9-180 | Et | Ac | C—SO₂Et | C—H | $CF(CF_3)_2$ | Me | 1 | |
| 9-181 | Et | Ac | C—SO₂Et | C—H | $CF(CF_3)_2$ | Me | 2 | |
| 9-182 | Et | H | C—S-n-Pr | C—H | $CF(CF_3)_2$ | Me | 0 | |
| 9-183 | Et | H | C—S-n-Pr | C—H | $CF(CF_3)_2$ | Me | 1 | |
| 9-184 | Et | H | C—S-n-Pr | C—H | $CF(CF_3)_2$ | Me | 2 | |
| 9-185 | Et | Ac | C—S-n-Pr | C—H | $CF(CF_3)_2$ | Me | 0 | |
| 9-186 | Et | Ac | C—S-n-Pr | C—H | $CF(CF_3)_2$ | Me | 1 | |
| 9-187 | Et | Ac | C—S-n-Pr | C—H | $CF(CF_3)_2$ | Me | 2 | |
| 9-188 | Et | H | C—SO—n-Pr | C—H | $CF(CF_3)_2$ | Me | 0 | |
| 9-189 | Et | H | C—SO—n-Pr | C—H | $CF(CF_3)_2$ | Me | 1 | |
| 9-190 | Et | H | C—SO—n-Pr | C—H | $CF(CF_3)_2$ | Me | 2 | |
| 9-191 | Et | Ac | C—SO—n-Pr | C—H | $CF(CF_3)_2$ | Me | 0 | |
| 9-192 | Et | Ac | C—SO—n-Pr | C—H | $CF(CF_3)_2$ | Me | 1 | |
| 9-193 | Et | Ac | C—SO—n-Pr | C—H | $CF(CF_3)_2$ | Me | 2 | |
| 9-194 | Et | H | C—SO₂n-Pr | C—H | $CF(CF_3)_2$ | Me | 0 | |
| 9-195 | Et | H | C—SO₂n-Pr | C—H | $CF(CF_3)_2$ | Me | 1 | |
| 9-196 | Et | H | C—SO₂n-Pr | C—H | $CF(CF_3)_2$ | Me | 2 | |
| 9-197 | Et | Ac | C—SO₂n-Pr | C—H | $CF(CF_3)_2$ | Me | 0 | |
| 9-198 | Et | Ac | C—SO₂n-Pr | C—H | $CF(CF_3)_2$ | Me | 1 | |
| 9-199 | Et | Ac | C—SO₂n-Pr | C—H | $CF(CF_3)_2$ | Me | 2 | |
| 9-200 | Et | H | C—S-i-Pr | C—H | $CF(CF_3)_2$ | Me | 0 | |

$R^4$, $R^5$ and $R^7$ each represent a hydrogen atom, and $A^1$ and $A^3$ each represent a CH group.

TABLE 9-9

| Compound No. | $R^1$ | $R^3$ | $A^2$ | $A^4$ | $R^6$ | Z | m | Physical property |
|---|---|---|---|---|---|---|---|---|
| 9-201 | Et | H | C—S—i-Pr | C—H | $CF(CF_3)_2$ | Me | 1 | |
| 9-202 | Et | H | C—S—i-Pr | C—H | $CF(CF_3)_2$ | Me | 2 | |
| 9-203 | Et | Ac | C—S—i-Pr | C—H | $CF(CF_3)_2$ | Me | 0 | |
| 9-204 | Et | Ac | C—S—i-Pr | C—H | $CF(CF_3)_2$ | Me | 1 | |
| 9-205 | Et | Ac | C—S—i-Pr | C—H | $CF(CF_3)_2$ | Me | 2 | |
| 9-206 | Et | H | C—SO—i-Pr | C—H | $CF(CF_3)_2$ | Me | 0 | |
| 9-207 | Et | H | C—SO—i-Pr | C—H | $CF(CF_3)_2$ | Me | 1 | |
| 9-208 | Et | H | C—SO—i-Pr | C—H | $CF(CF_3)_2$ | Me | 2 | |
| 9-209 | Et | Ac | C—SO—i-Pr | C—H | $CF(CF_3)_2$ | Me | 0 | |
| 9-210 | Et | Ac | C—SO—i-Pr | C—H | $CF(CF_3)_2$ | Me | 1 | |
| 9-211 | Et | Ac | C—SO—i-Pr | C—H | $CF(CF_3)_2$ | Me | 2 | |
| 9-212 | Et | H | C—$SO_2$i-Pr | C—H | $CF(CF_3)_2$ | Me | 0 | |
| 9-213 | Et | H | C—$SO_2$i-Pr | C—H | $CF(CF_3)_2$ | Me | 1 | |
| 9-214 | Et | H | C—$SO_2$i-Pr | C—H | $CF(CF_3)_2$ | Me | 2 | |
| 9-215 | Et | Ac | C—$SO_2$i-Pr | C—H | $CF(CF_3)_2$ | Me | 0 | |
| 9-216 | Et | Ac | C—$SO_2$i-Pr | C—H | $CF(CF_3)_2$ | Me | 1 | |
| 9-217 | Et | Ac | C—$SO_2$i-Pr | C—H | $CF(CF_3)_2$ | Me | 2 | |
| 9-218 | Et | H | C—S—n-Bu | C—H | $CF(CF_3)_2$ | Me | 0 | |
| 9-219 | Et | H | C—S—n-Bu | C—H | $CF(CF_3)_2$ | Me | 1 | |
| 9-220 | Et | H | C—S—n-Bu | C—H | $CF(CF_3)_2$ | Me | 2 | |
| 9-221 | Et | Ac | C—S—n-Bu | C—H | $CF(CF_3)_2$ | Me | 0 | |
| 9-222 | Et | Ac | C—S—n-Bu | C—H | $CF(CF_3)_2$ | Me | 1 | |
| 9-223 | Et | Ac | C—S—n-Bu | C—H | $CF(CF_3)_2$ | Me | 2 | |
| 9-224 | Et | H | C—SO—n-Bu | C—H | $CF(CF_3)_2$ | Me | 0 | |
| 9-225 | Et | H | C—SO—n-Bu | C—H | $CF(CF_3)_2$ | Me | 1 | |

$R^4$, $R^5$ and $R^7$ each represent a hydrogen atom, and $A^1$ and $A^3$ each represent a CH group.

TABLE 9-10

| Compound No. | $R^1$ | $R^3$ | $A^2$ | $A^4$ | $R^6$ | Z | m | Physical property |
|---|---|---|---|---|---|---|---|---|
| 9-226 | Et | H | C—SO—n-Bu | C—H | $CF(CF_3)_2$ | Me | 2 | |
| 9-227 | Et | Ac | C—SO—n-Bu | C—H | $CF(CF_3)_2$ | Me | 0 | |
| 9-228 | Et | Ac | C—SO—n-Bu | C—H | $CF(CF_3)_2$ | Me | 1 | |
| 9-229 | Et | Ac | C—SO—n-Bu | C—H | $CF(CF_3)_2$ | Me | 2 | |
| 9-230 | Et | H | C—$SO_2$n-Bu | C—H | $CF(CF_3)_2$ | Me | 0 | |
| 9-231 | Et | H | C—$SO_2$n-Bu | C—H | $CF(CF_3)_2$ | Me | 1 | |
| 9-232 | Et | H | C—$SO_2$n-Bu | C—H | $CF(CF_3)_2$ | Me | 2 | |
| 9-233 | Et | Ac | C—$SO_2$n-Bu | C—H | $CF(CF_3)_2$ | Me | 0 | |
| 9-234 | Et | Ac | C—$SO_2$n-Bu | C—H | $CF(CF_3)_2$ | Me | 1 | |
| 9-235 | Et | Ac | C—$SO_2$n-Bu | C—H | $CF(CF_3)_2$ | Me | 2 | |
| 9-236 | Et | H | C—S—i-Bu | C—H | $CF(CF_3)_2$ | Me | 0 | |
| 9-237 | Et | H | C—S—i-Bu | C—H | $CF(CF_3)_2$ | Me | 1 | |
| 9-238 | Et | H | C—S—i-Bu | C—H | $CF(CF_3)_2$ | Me | 2 | |
| 9-239 | Et | Ac | C—S—i-Bu | C—H | $CF(CF_3)_2$ | Me | 0 | |
| 9-240 | Et | Ac | C—S—i-Bu | C—H | $CF(CF_3)_2$ | Me | 1 | |
| 9-241 | Et | Ac | C—S—i-Bu | C—H | $CF(CF_3)_2$ | Me | 2 | |
| 9-242 | Et | H | C—SO—i-Bu | C—H | $CF(CF_3)_2$ | Me | 0 | |
| 9-243 | Et | H | C—SO—i-Bu | C—H | $CF(CF_3)_2$ | Me | 1 | |
| 9-244 | Et | H | C—SO—i-Bu | C—H | $CF(CF_3)_2$ | Me | 2 | |
| 9-245 | Et | Ac | C—SO—i-Bu | C—H | $CF(CF_3)_2$ | Me | 0 | |
| 9-246 | Et | Ac | C—SO—i-Bu | C—H | $CF(CF_3)_2$ | Me | 1 | |
| 9-247 | Et | Ac | C—SO—i-Bu | C—H | $CF(CF_3)_2$ | Me | 2 | |
| 9-248 | Et | H | C—$SO_2$i-Bu | C—H | $CF(CF_3)_2$ | Me | 0 | |
| 9-249 | Et | H | C—$SO_2$i-Bu | C—H | $CF(CF_3)_2$ | Me | 1 | |
| 9-250 | Et | H | C—$SO_2$i-Bu | C—H | $CF(CF_3)_2$ | Me | 2 | |

$R^4$, $R^5$ and $R^7$ each represent a hydrogen atom, and $A^1$ and $A^3$ each represent a CH group.

TABLE 9-11

| Compound No. | R¹ | R³ | A² | A⁴ | R⁶ | Z | m | Physical property |
|---|---|---|---|---|---|---|---|---|
| 9-251 | Et | Ac | C—SO₂i-Bu | C—H | CF(CF₃)₂ | Me | 0 | |
| 9-252 | Et | Ac | C—SO₂i-Bu | C—H | CF(CF₃)₂ | Me | 1 | |
| 9-253 | Et | Ac | C—SO₂i-Bu | C—H | CF(CF₃)₂ | Me | 2 | |
| 9-254 | Et | H | C—Ss-Bu | C—H | CF(CF₃)₂ | Me | 0 | |
| 9-255 | Et | H | C—Ss-Bu | C—H | CF(CF₃)₂ | Me | 1 | |
| 9-256 | Et | H | C—Ss-Bu | C—H | CF(CF₃)₂ | Me | 2 | |
| 9-257 | Et | Ac | C—Ss-Bu | C—H | CF(CF₃)₂ | Me | 0 | |
| 9-258 | Et | Ac | C—Ss-Bu | C—H | CF(CF₃)₂ | Me | 1 | |
| 9-259 | Et | Ac | C—Ss-Bu | C—H | CF(CF₃)₂ | Me | 2 | |
| 9-260 | Et | H | C—SO—s-Bu | C—H | CF(CF₃)₂ | Me | 0 | |
| 9-261 | Et | H | C—SO—s-Bu | C—H | CF(CF₃)₂ | Me | 1 | |
| 9-262 | Et | H | C—SO—s-Bu | C—H | CF(CF₃)₂ | Me | 2 | |
| 9-263 | Et | Ac | C—SO—s-Bu | C—H | CF(CF₃)₂ | Me | 0 | |
| 9-264 | Et | Ac | C—SO—s-Bu | C—H | CF(CF₃)₂ | Me | 1 | |
| 9-265 | Et | Ac | C—SO—s-Bu | C—H | CF(CF₃)₂ | Me | 2 | |
| 9-266 | Et | H | C—SO₂s-Bu | C—H | CF(CF₃)₂ | Me | 0 | |
| 9-267 | Et | H | C—SO₂s-Bu | C—H | CF(CF₃)₂ | Me | 1 | |
| 9-268 | Et | H | C—SO₂s-Bu | C—H | CF(CF₃)₂ | Me | 2 | |
| 9-269 | Et | Ac | C—SO₂s-Bu | C—H | CF(CF₃)₂ | Me | 0 | |
| 9-270 | Et | Ac | C—SO₂s-Bu | C—H | CF(CF₃)₂ | Me | 1 | |
| 9-271 | Et | Ac | C—SO₂s-Bu | C—H | CF(CF₃)₂ | Me | 2 | |
| 9-272 | Et | H | C—St-Bu | C—H | CF(CF₃)₂ | Me | 0 | |
| 9-273 | Et | H | C—St-Bu | C—H | CF(CF₃)₂ | Me | 1 | |
| 9-274 | Et | H | C—St-Bu | C—H | CF(CF₃)₂ | Me | 2 | |
| 9-275 | Et | Ac | C—St-Bu | C—H | CF(CF₃)₂ | Me | 0 | |

$R^4$, $R^5$ and $R^7$ each represent a hydrogen atom, and $A^1$ and $A^3$ each represent a CH group.

TABLE 9-12

| Compound No. | R¹ | R³ | A² | A⁴ | R⁶ | Z | m | Physical property |
|---|---|---|---|---|---|---|---|---|
| 9-276 | Et | Ac | C—St-Bu | C—H | CF(CF₃)₂ | Me | 1 | |
| 9-277 | Et | Ac | C—St-Bu | C—H | CF(CF₃)₂ | Me | 2 | |
| 9-278 | Et | H | C—SO—t-Bu | C—H | CF(CF₃)₂ | Me | 0 | |
| 9-279 | Et | H | C—SO—t-Bu | C—H | CF(CF₃)₂ | Me | 1 | |
| 9-280 | Et | H | C—SO—t-Bu | C—H | CF(CF₃)₂ | Me | 2 | |
| 9-281 | Et | Ac | C—SO—t-Bu | C—H | CF(CF₃)₂ | Me | 0 | |
| 9-282 | Et | Ac | C—SO—t-Bu | C—H | CF(CF₃)₂ | Me | 1 | |
| 9-283 | Et | Ac | C—SO—t-Bu | C—H | CF(CF₃)₂ | Me | 2 | |
| 9-284 | Et | H | C—SO₂t-Bu | C—H | CF(CF₃)₂ | Me | 0 | |
| 9-285 | Et | H | C—SO₂t-Bu | C—H | CF(CF₃)₂ | Me | 1 | |
| 9-286 | Et | H | C—SO₂t-Bu | C—H | CF(CF₃)₂ | Me | 2 | |
| 9-287 | Et | Ac | C—SO₂t-Bu | C—H | CF(CF₃)₂ | Me | 0 | |
| 9-288 | Et | Ac | C—SO₂t-Bu | C—H | CF(CF₃)₂ | Me | 1 | |
| 9-289 | Et | Ac | C—SO₂t-Bu | C—H | CF(CF₃)₂ | Me | 2 | |
| 9-290 | Et | H | C—CF₃ | C—OMe | CF(CF₃)₂ | Me | 0 | |
| 9-291 | Et | H | C—CF₃ | C—OMe | CF(CF₃)₂ | Me | 1 | |
| 9-292 | Et | H | C—CF₃ | C—OMe | CF(CF₃)₂ | Me | 2 | |
| 9-293 | Et | Ac | C—CF₃ | C—OMe | CF(CF₃)₂ | Me | 0 | |
| 9-294 | Et | Ac | C—CF₃ | C—OMe | CF(CF₃)₂ | Me | 1 | |
| 9-295 | Et | Ac | C—CF₃ | C—OMe | CF(CF₃)₂ | Me | 2 | |
| 9-296 | Et | H | C—CF₃ | C—OEt | CF(CF₃)₂ | Me | 0 | |
| 9-297 | Et | H | C—CF₃ | C—OEt | CF(CF₃)₂ | Me | 1 | |
| 9-298 | Et | H | C—CF₃ | C—OEt | CF(CF₃)₂ | Me | 2 | |
| 9-299 | Et | Ac | C—CF₃ | C—OEt | CF(CF₃)₂ | Me | 0 | |
| 9-300 | Et | Ac | C—CF₃ | C—OEt | CF(CF₃)₂ | Me | 1 | |

$R^4$, $R^5$ and $R^7$ each represent a hydrogen atom, and $A^1$ and $A^3$ each represent a CH group.

TABLE 9-13

| Compound No. | R¹ | R³ | A² | A⁴ | R⁶ | Z | m | Physical property |
|---|---|---|---|---|---|---|---|---|
| 9-301 | Et | Ac | C—CF₃ | C—OEt | CF(CF₃)₂ | Me | 2 | |
| 9-302 | Et | H | C—CF₃ | C—On-Pr | CF(CF₃)₂ | Me | 0 | |
| 9-303 | Et | H | C—CF₃ | C—On-Pr | CF(CF₃)₂ | Me | 1 | |
| 9-304 | Et | H | C—CF₃ | C—On-Pr | CF(CF₃)₂ | Me | 2 | |

TABLE 9-13-continued

| Compound No. | R¹ | R³ | A² | A⁴ | R⁶ | Z | m | Physical property |
|---|---|---|---|---|---|---|---|---|
| 9-305 | Et | Ac | C—CF₃ | C—On-Pr | CF(CF₃)₂ | Me | 0 | |
| 9-306 | Et | Ac | C—CF₃ | C—On-Pr | CF(CF₃)₂ | Me | 1 | |
| 9-307 | Et | Ac | C—CF₃ | C—On-Pr | CF(CF₃)₂ | Me | 2 | |
| 9-308 | Et | H | C—CF₃ | C—Oi-Pr | CF(CF₃)₂ | Me | 0 | |
| 9-309 | Et | H | C—CF₃ | C—Oi-Pr | CF(CF₃)₂ | Me | 1 | |
| 9-310 | Et | H | C—CF₃ | C—Oi-Pr | CF(CF₃)₂ | Me | 2 | |
| 9-311 | Et | Ac | C—CF₃ | C—Oi-Pr | CF(CF₃)₂ | Me | 0 | |
| 9-312 | Et | Ac | C—CF₃ | C—Oi-Pr | CF(CF₃)₂ | Me | 1 | |
| 9-313 | Et | Ac | C—CF₃ | C—Oi-Pr | CF(CF₃)₂ | Me | 2 | |
| 9-314 | Et | H | C—CF₃ | C—On-Bu | CF(CF₃)₂ | Me | 0 | |
| 9-315 | Et | H | C—CF₃ | C—On-Bu | CF(CF₃)₂ | Me | 1 | |
| 9-316 | Et | H | C—CF₃ | C—On-Bu | CF(CF₃)₂ | Me | 2 | |
| 9-317 | Et | Ac | C—CF₃ | C—On-Bu | CF(CF₃)₂ | Me | 0 | |
| 9-318 | Et | Ac | C—CF₃ | C—On-Bu | CF(CF₃)₂ | Me | 1 | |
| 9-319 | Et | Ac | C—CF₃ | C—On-Bu | CF(CF₃)₂ | Me | 2 | |
| 9-320 | Et | H | C—CF₃ | C—Oi-Bu | CF(CF₃)₂ | Me | 0 | |
| 9-321 | Et | H | C—CF₃ | C—Oi-Bu | CF(CF₃)₂ | Me | 1 | |
| 9-322 | Et | H | C—CF₃ | C—Oi-Bu | CF(CF₃)₂ | Me | 2 | |
| 9-323 | Et | Ac | C—CF₃ | C—Oi-Bu | CF(CF₃)₂ | Me | 0 | |
| 9-324 | Et | Ac | C—CF₃ | C—Oi-Bu | CF(CF₃)₂ | Me | 1 | |
| 9-325 | Et | Ac | C—CF₃ | C—Oi-Bu | CF(CF₃)₂ | Me | 2 | |

$R^4$, $R^5$ and $R^7$ each represent a hydrogen atom, and $A^1$ and $A^3$ each represent a CH group.

TABLE 9-14

| Compound No. | R¹ | R³ | A² | A⁴ | R⁶ | Z | m | Physical property |
|---|---|---|---|---|---|---|---|---|
| 9-326 | Et | H | C—CF₃ | C—Os-Bu | CF(CF₃)₂ | Me | 0 | |
| 9-327 | Et | H | C—CF₃ | C—Os-Bu | CF(CF₃)₂ | Me | 1 | |
| 9-328 | Et | H | C—CF₃ | C—Os-Bu | CF(CF₃)₂ | Me | 2 | |
| 9-329 | Et | Ac | C—CF₃ | C—Os-Bu | CF(CF₃)₂ | Me | 0 | |
| 9-330 | Et | Ac | C—CF₃ | C—Os-Bu | CF(CF₃)₂ | Me | 1 | |
| 9-331 | Et | Ac | C—CF₃ | C—Os-Bu | CF(CF₃)₂ | Me | 2 | |
| 9-332 | Et | H | C—CF₃ | C—Ot-Bu | CF(CF₃)₂ | Me | 0 | |
| 9-333 | Et | H | C—CF₃ | C—Ot-Bu | CF(CF₃)₂ | Me | 1 | |
| 9-334 | Et | H | C—CF₃ | C—Ot-Bu | CF(CF₃)₂ | Me | 2 | |
| 9-335 | Et | Ac | C—CF₃ | C—Ot-Bu | CF(CF₃)₂ | Me | 0 | |
| 9-336 | Et | Ac | C—CF₃ | C—Ot-Bu | CF(CF₃)₂ | Me | 1 | |
| 9-337 | Et | Ac | C—CF₃ | C—Ot-Bu | CF(CF₃)₂ | Me | 2 | |
| 9-338 | Et | H | C—OMe | C—H | OCF₃ | Me | 0 | |
| 9-339 | Et | H | C—OMe | C—H | OCF₃ | Me | 1 | |
| 9-340 | Et | H | C—OMe | C—H | OCF₃ | Me | 2 | |
| 9-341 | Et | Ac | C—OMe | C—H | OCF₃ | Me | 0 | |
| 9-342 | Et | Ac | C—OMe | C—H | OCF₃ | Me | 1 | |
| 9-343 | Et | Ac | C—OMe | C—H | OCF₃ | Me | 2 | |
| 9-344 | Et | H | C—OEt | C—H | OCF₃ | Me | 0 | |
| 9-345 | Et | H | C—OEt | C—H | OCF₃ | Me | 1 | |
| 9-346 | Et | H | C—OEt | C—H | OCF₃ | Me | 2 | |
| 9-347 | Et | Ac | C—OEt | C—H | OCF₃ | Me | 0 | |
| 9-348 | Et | Ac | C—OEt | C—H | OCF₃ | Me | 1 | |
| 9-349 | Et | Ac | C—OEt | C—H | OCF₃ | Me | 2 | |
| 9-350 | Et | H | C—On-Pr | C—H | OCF₃ | Me | 0 | |

$R^4$, $R^5$ and $R^7$ each represent a hydrogen atom, and $A^1$ and $A^3$ each represent a CH group.

TABLE 9-15

| Compound No. | R¹ | R³ | A² | A⁴ | R⁶ | Z | m | Physical property |
|---|---|---|---|---|---|---|---|---|
| 9-351 | Et | H | C—On-Pr | C—H | OCF₃ | Me | 1 | |
| 9-352 | Et | H | C—On-Pr | C—H | OCF₃ | Me | 2 | |
| 9-353 | Et | Ac | C—On-Pr | C—H | OCF₃ | Me | 0 | |
| 9-354 | Et | Ac | C—On-Pr | C—H | OCF₃ | Me | 1 | |
| 9-355 | Et | Ac | C—On-Pr | C—H | OCF₃ | Me | 2 | |
| 9-356 | Et | H | C—Oi-Pr | C—H | OCF₃ | Me | 0 | |
| 9-357 | Et | H | C—Oi-Pr | C—H | OCF₃ | Me | 1 | |
| 9-358 | Et | H | C—Oi-Pr | C—H | OCF₃ | Me | 2 | |
| 9-359 | Et | Ac | C—Oi-Pr | C—H | OCF₃ | Me | 0 | |
| 9-360 | Et | Ac | C—Oi-Pr | C—H | OCF₃ | Me | 1 | |
| 9-361 | Et | Ac | C—Oi-Pr | C—H | OCF₃ | Me | 2 | |
| 9-362 | Et | H | C—On-Bu | C—H | OCF₃ | Me | 0 | |
| 9-363 | Et | H | C—On-Bu | C—H | OCF₃ | Me | 1 | |
| 9-364 | Et | H | C—On-Bu | C—H | OCF₃ | Me | 2 | |
| 9-365 | Et | Ac | C—On-Bu | C—H | OCF₃ | Me | 0 | |
| 9-366 | Et | Ac | C—On-Bu | C—H | OCF₃ | Me | 1 | |
| 9-367 | Et | Ac | C—On-Bu | C—H | OCF₃ | Me | 2 | |
| 9-368 | Et | H | C—Oi-Bu | C—H | OCF₃ | Me | 0 | |
| 9-369 | Et | H | C—Oi-Bu | C—H | OCF₃ | Me | 1 | |
| 9-370 | Et | H | C—Oi-Bu | C—H | OCF₃ | Me | 2 | |
| 9-371 | Et | Ac | C—Oi-Bu | C—H | OCF₃ | Me | 0 | |
| 9-372 | Et | Ac | C—Oi-Bu | C—H | OCF₃ | Me | 1 | |
| 9-373 | Et | Ac | C—Oi-Bu | C—H | OCF₃ | Me | 2 | |
| 9-374 | Et | H | C—Os-Bu | C—H | OCF₃ | Me | 0 | |
| 9-375 | Et | H | C—Os-Bu | C—H | OCF₃ | Me | 1 | |

$R^4$, $R^5$ and $R^7$ each represent a hydrogen atom, and $A^1$ and $A^3$ each represent a CH group.

TABLE 9-16

| Compound No. | R¹ | R³ | A² | A⁴ | R⁶ | Z | m | Physical property |
|---|---|---|---|---|---|---|---|---|
| 9-376 | Et | H | C—Os-Bu | C—H | OCF₃ | Me | 2 | |
| 9-377 | Et | Ac | C—Os-Bu | C—H | OCF₃ | Me | 0 | |
| 9-378 | Et | Ac | C—Os-Bu | C—H | OCF₃ | Me | 1 | |
| 9-379 | Et | Ac | C—Os-Bu | C—H | OCF₃ | Me | 2 | |
| 9-380 | Et | H | C—Ot-Bu | C—H | OCF₃ | Me | 0 | |
| 9-381 | Et | H | C—Ot-Bu | C—H | OCF₃ | Me | 1 | |
| 9-382 | Et | H | C—Ot-Bu | C—H | OCF₃ | Me | 2 | |
| 9-383 | Et | Ac | C—Ot-Bu | C—H | OCF₃ | Me | 0 | |
| 9-384 | Et | Ac | C—Ot-Bu | C—H | OCF₃ | Me | 1 | |
| 9-385 | Et | Ac | C—Ot-Bu | C—H | OCF₃ | Me | 2 | |
| 9-386 | Et | H | C—OPh | C—H | OCF₃ | Me | 0 | |
| 9-387 | Et | H | C—OPh | C—H | OCF₃ | Me | 1 | |
| 9-388 | Et | H | C—OPh | C—H | OCF₃ | Me | 2 | |
| 9-389 | Et | Ac | C—OPh | C—H | OCF₃ | Me | 0 | |
| 9-390 | Et | Ac | C—OPh | C—H | OCF₃ | Me | 1 | |
| 9-391 | Et | Ac | C—OPh | C—H | OCF₃ | Me | 2 | |

TABLE 9-16-continued

| Compound No. | $R^1$ | $R^3$ | $A^2$ | $A^4$ | $R^6$ | Z | m | Physical property |
|---|---|---|---|---|---|---|---|---|
| 9-392 | Et | H | C—Me | C—H | $OCF_3$ | Me | 0 | |
| 9-393 | Et | H | C—Me | C—H | $OCF_3$ | Me | 1 | |
| 9-394 | Et | H | C—Me | C—H | $OCF_3$ | Me | 2 | |
| 9-395 | Et | Ac | C—Me | C—H | $OCF_3$ | Me | 0 | |
| 9-396 | Et | Ac | C—Me | C—H | $OCF_3$ | Me | 1 | |
| 9-397 | Et | Ac | C—Me | C—H | $OCF_3$ | Me | 2 | |
| 9-398 | Et | H | C—Et | C—H | $OCF_3$ | Me | 0 | |
| 9-399 | Et | H | C—Et | C—H | $OCF_3$ | Me | 1 | |
| 9-400 | Et | H | C—Et | C—H | $OCF_3$ | Me | 2 | |

$R^4$, $R^5$ and $R^7$ each represent a hydrogen atom, and $A^1$ and $A^3$ each represent a CH group.

TABLE 9-17

| Compound No. | $R^1$ | $R^3$ | $A^2$ | $A^4$ | $R^6$ | Z | m | Physical property |
|---|---|---|---|---|---|---|---|---|
| 9-401 | Et | Ac | C—Et | C—H | $OCF_3$ | Me | 0 | |
| 9-402 | Et | Ac | C—Et | C—H | $OCF_3$ | Me | 1 | |
| 9-403 | Et | Ac | C—Et | C—H | $OCF_3$ | Me | 2 | |
| 9-404 | Et | H | C—n-Pr | C—H | $OCF_3$ | Me | 0 | |
| 9-405 | Et | H | C—n-Pr | C—H | $OCF_3$ | Me | 1 | |
| 9-406 | Et | H | C—n-Pr | C—H | $OCF_3$ | Me | 2 | |
| 9-407 | Et | Ac | C—n-Pr | C—H | $OCF_3$ | Me | 0 | |
| 9-408 | Et | Ac | C—n-Pr | C—H | $OCF_3$ | Me | 1 | |
| 9-409 | Et | Ac | C—n-Pr | C—H | $OCF_3$ | Me | 2 | |
| 9-410 | Et | H | C—i-Pr | C—H | $OCF_3$ | Me | 0 | |
| 9-411 | Et | H | C—i-Pr | C—H | $OCF_3$ | Me | 1 | |
| 9-412 | Et | H | C—i-Pr | C—H | $OCF_3$ | Me | 2 | |
| 9-413 | Et | Ac | C—i-Pr | C—H | $OCF_3$ | Me | 0 | |
| 9-414 | Et | Ac | C—i-Pr | C—H | $OCF_3$ | Me | 1 | |
| 9-415 | Et | Ac | C—i-Pr | C—H | $OCF_3$ | Me | 2 | |
| 9-416 | Et | H | C—n-Bu | C—H | $OCF_3$ | Me | 0 | |
| 9-417 | Et | H | C—n-Bu | C—H | $OCF_3$ | Me | 1 | |
| 9-418 | Et | H | C—n-Bu | C—H | $OCF_3$ | Me | 2 | |
| 9-419 | Et | Ac | C—n-Bu | C—H | $OCF_3$ | Me | 0 | |
| 9-420 | Et | Ac | C—n-Bu | C—H | $OCF_3$ | Me | 1 | |
| 9-421 | Et | Ac | C—n-Bu | C—H | $OCF_3$ | Me | 2 | |
| 9-422 | Et | H | C—i-Bu | C—H | $OCF_3$ | Me | 0 | |
| 9-423 | Et | H | C—i-Bu | C—H | $OCF_3$ | Me | 1 | |
| 9-424 | Et | H | C—i-Bu | C—H | $OCF_3$ | Me | 2 | |
| 9-425 | Et | Ac | C—i-Bu | C—H | $OCF_3$ | Me | 0 | |

$R^4$, $R^5$ and $R^7$ each represent a hydrogen atom, and $A^1$ and $A^3$ each represent a CH group.

TABLE 9-18

| Compound No. | $R^1$ | $R^3$ | $A^2$ | $A^4$ | $R^6$ | Z | m | Physical property |
|---|---|---|---|---|---|---|---|---|
| 9-426 | Et | Ac | C—i-Bu | C—H | $OCF_3$ | Me | 1 | |
| 9-427 | Et | Ac | C—i-Bu | C—H | $OCF_3$ | Me | 2 | |
| 9-428 | Et | H | C—s-Bu | C—H | $OCF_3$ | Me | 0 | |
| 9-429 | Et | H | C—s-Bu | C—H | $OCF_3$ | Me | 1 | |
| 9-430 | Et | H | C—s-Bu | C—H | $OCF_3$ | Me | 2 | |
| 9-431 | Et | Ac | C—s-Bu | C—H | $OCF_3$ | Me | 0 | |
| 9-432 | Et | Ac | C—s-Bu | C—H | $OCF_3$ | Me | 1 | |
| 9-433 | Et | Ac | C—s-Bu | C—H | $OCF_3$ | Me | 2 | |
| 9-434 | Et | H | C—t-Bu | C—H | $OCF_3$ | Me | 0 | |
| 9-435 | Et | H | C—t-Bu | C—H | $OCF_3$ | Me | 1 | |
| 9-436 | Et | H | C—t-Bu | C—H | $OCF_3$ | Me | 2 | |
| 9-437 | Et | Ac | C—t-Bu | C—H | $OCF_3$ | Me | 0 | |
| 9-438 | Et | Ac | C—t-Bu | C—H | $OCF_3$ | Me | 1 | |
| 9-439 | Et | Ac | C—t-Bu | C—H | $OCF_3$ | Me | 2 | |
| 9-440 | Et | H | C—c-Pr | C—H | $OCF_3$ | Me | 0 | |
| 9-441 | Et | H | C—c-Pr | C—H | $OCF_3$ | Me | 1 | |
| 9-442 | Et | H | C—c-Pr | C—H | $OCF_3$ | Me | 2 | |
| 9-443 | Et | Ac | C—c-Pr | C—H | $OCF_3$ | Me | 0 | |

TABLE 9-18-continued

| Compound No. | $R^1$ | $R^3$ | $A^2$ | $A^4$ | $R^6$ | Z | m | Physical property |
|---|---|---|---|---|---|---|---|---|
| 9-444 | Et | Ac | C—c-Pr | C—H | $OCF_3$ | Me | 1 | |
| 9-445 | Et | Ac | C—c-Pr | C—H | $OCF_3$ | Me | 2 | |
| 9-446 | Et | H | C—SMe | C—H | $OCF_3$ | Me | 0 | |
| 9-447 | Et | H | C—SMe | C—H | $OCF_3$ | Me | 1 | |
| 9-448 | Et | H | C—SMe | C—H | $OCF_3$ | Me | 2 | |
| 9-449 | Et | Ac | C—SMe | C—H | $OCF_3$ | Me | 0 | |
| 9-450 | Et | Ac | C—SMe | C—H | $OCF_3$ | Me | 1 | |

$R^4$, $R^5$ and $R^7$ each represent a hydrogen atom, and $A^1$ and $A^3$ each represent a CH group.

TABLE 9-19

| Compound No. | $R^1$ | $R^3$ | $A^2$ | $A^4$ | $R^6$ | Z | m | Physical property |
|---|---|---|---|---|---|---|---|---|
| 9-451 | Et | Ac | C—SMe | C—H | $OCF_3$ | Me | 2 | |
| 9-452 | Et | H | C—SOMe | C—H | $OCF_3$ | Me | 0 | |
| 9-453 | Et | H | C—SOMe | C—H | $OCF_3$ | Me | 1 | |
| 9-454 | Et | H | C—SOMe | C—H | $OCF_3$ | Me | 2 | |
| 9-455 | Et | Ac | C—SOMe | C—H | $OCF_3$ | Me | 0 | |
| 9-456 | Et | Ac | C—SOMe | C—H | $OCF_3$ | Me | 1 | |
| 9-457 | Et | Ac | C—SOMe | C—H | $OCF_3$ | Me | 2 | |
| 9-458 | Et | H | C—$SO_2$Me | C—H | $OCF_3$ | Me | 0 | |
| 9-459 | Et | H | C—$SO_2$Me | C—H | $OCF_3$ | Me | 1 | |
| 9-460 | Et | H | C—$SO_2$Me | C—H | $OCF_3$ | Me | 2 | |
| 9-461 | Et | Ac | C—$SO_2$Me | C—H | $OCF_3$ | Me | 0 | |
| 9-462 | Et | Ac | C—$SO_2$Me | C—H | $OCF_3$ | Me | 1 | |
| 9-463 | Et | Ac | C—$SO_2$Me | C—H | $OCF_3$ | Me | 2 | |
| 9-464 | Et | H | C—SEt | C—H | $OCF_3$ | Me | 0 | |
| 9-465 | Et | H | C—SEt | C—H | $OCF_3$ | Me | 1 | |
| 9-466 | Et | H | C—SEt | C—H | $OCF_3$ | Me | 2 | |
| 9-467 | Et | Ac | C—SEt | C—H | $OCF_3$ | Me | 0 | |
| 9-468 | Et | Ac | C—SEt | C—H | $OCF_3$ | Me | 1 | |
| 9-469 | Et | Ac | C—SEt | C—H | $OCF_3$ | Me | 2 | |
| 9-470 | Et | H | C—SOEt | C—H | $OCF_3$ | Me | 0 | |
| 9-471 | Et | H | C—SOEt | C—H | $OCF_3$ | Me | 1 | |
| 9-472 | Et | H | C—SOEt | C—H | $OCF_3$ | Me | 2 | |
| 9-473 | Et | Ac | C—SOEt | C—H | $OCF_3$ | Me | 0 | |
| 9-474 | Et | Ac | C—SOEt | C—H | $OCF_3$ | Me | 1 | |
| 9-475 | Et | Ac | C—SOEt | C—H | $OCF_3$ | Me | 2 | |

$R^4$, $R^5$ and $R^7$ each represent a hydrogen atom, and $A^1$ and $A^3$ each represent a CH group.

TABLE 9-20

| Compound No. | $R^1$ | $R^3$ | $A^2$ | $A^4$ | $R^6$ | Z | m | Physical property |
|---|---|---|---|---|---|---|---|---|
| 9-476 | Et | H | C—$SO_2$Et | C—H | $OCF_3$ | Me | 0 | |
| 9-477 | Et | H | C—$SO_2$Et | C—H | $OCF_3$ | Me | 1 | |
| 9-478 | Et | H | C—$SO_2$Et | C—H | $OCF_3$ | Me | 2 | |
| 9-479 | Et | Ac | C—$SO_2$Et | C—H | $OCF_3$ | Me | 0 | |
| 9-480 | Et | Ac | C—$SO_2$Et | C—H | $OCF_3$ | Me | 1 | |
| 9-481 | Et | Ac | C—$SO_2$Et | C—H | $OCF_3$ | Me | 2 | |
| 9-482 | Et | H | C—Sn-Pr | C—H | $OCF_3$ | Me | 0 | |
| 9-483 | Et | H | C—Sn-Pr | C—H | $OCF_3$ | Me | 1 | |
| 9-484 | Et | H | C—Sn-Pr | C—H | $OCF_3$ | Me | 2 | |
| 9-485 | Et | Ac | C—Sn-Pr | C—H | $OCF_3$ | Me | 0 | |
| 9-486 | Et | Ac | C—Sn-Pr | C—H | $OCF_3$ | Me | 1 | |
| 9-487 | Et | Ac | C—Sn-Pr | C—H | $OCF_3$ | Me | 2 | |
| 9-488 | Et | H | C—SO—n-Pr | C—H | $OCF_3$ | Me | 0 | |
| 9-489 | Et | H | C—SO—n-Pr | C—H | $OCF_3$ | Me | 1 | |
| 9-490 | Et | H | C—SO—n-Pr | C—H | $OCF_3$ | Me | 2 | |
| 9-491 | Et | Ac | C—SO—n-Pr | C—H | $OCF_3$ | Me | 0 | |
| 9-492 | Et | Ac | C—SO—n-Pr | C—H | $OCF_3$ | Me | 1 | |
| 9-493 | Et | Ac | C—SO—n-Pr | C—H | $OCF_3$ | Me | 2 | |
| 9-494 | Et | H | C—$SO_2$n-Pr | C—H | $OCF_3$ | Me | 0 | |
| 9-495 | Et | H | C—$SO_2$n-Pr | C—H | $OCF_3$ | Me | 1 | |

TABLE 9-20-continued

| Compound No. | R$^1$ | R$^3$ | A$^2$ | A$^4$ | R$^6$ | Z | m | Physical property |
|---|---|---|---|---|---|---|---|---|
| 9-496 | Et | H | C—SO$_2$n-Pr | C—H | OCF$_3$ | Me | 2 | |
| 9-497 | Et | Ac | C—SO$_2$n-Pr | C—H | OCF$_3$ | Me | 0 | |
| 9-498 | Et | Ac | C—SO$_2$n-Pr | C—H | OCF$_3$ | Me | 1 | |
| 9-499 | Et | Ac | C—SO$_2$n-Pr | C—H | OCF$_3$ | Me | 2 | |
| 9-500 | Et | H | C—Si-Pr | C—H | OCF$_3$ | Me | 0 | |

R$^4$, R$^5$ and R$^7$ each represent a hydrogen atom, and A$^1$ and A$^3$ each represent a CH group.

TABLE 9-21

| Compound No. | R$^1$ | R$^3$ | A$^2$ | A$^4$ | R$^6$ | Z | m | Physical property |
|---|---|---|---|---|---|---|---|---|
| 9-501 | Et | H | C—Si-Pr | C—H | OCF$_3$ | Me | 1 | |
| 9-502 | Et | H | C—Si-Pr | C—H | OCF$_3$ | Me | 2 | |
| 9-503 | Et | Ac | C—Si-Pr | C—H | OCF$_3$ | Me | 0 | |
| 9-504 | Et | Ac | C—Si-Pr | C—H | OCF$_3$ | Me | 1 | |
| 9-505 | Et | Ac | C—Si-Pr | C—H | OCF$_3$ | Me | 2 | |
| 9-506 | Et | H | C—SO—i-Pr | C—H | OCF$_3$ | Me | 0 | |
| 9-507 | Et | H | C—SO—i-Pr | C—H | OCF$_3$ | Me | 1 | |
| 9-508 | Et | H | C—SO—i-Pr | C—H | OCF$_3$ | Me | 2 | |
| 9-509 | Et | Ac | C—SO—i-Pr | C—H | OCF$_3$ | Me | 0 | |
| 9-510 | Et | Ac | C—SO—i-Pr | C—H | OCF$_3$ | Me | 1 | |
| 9-511 | Et | Ac | C—SO—i-Pr | C—H | OCF$_3$ | Me | 2 | |
| 9-512 | Et | H | C—SO$_2$i-Pr | C—H | OCF$_3$ | Me | 0 | |
| 9-513 | Et | H | C—SO$_2$i-Pr | C—H | OCF$_3$ | Me | 1 | |
| 9-514 | Et | H | C—SO$_2$i-Pr | C—H | OCF$_3$ | Me | 2 | |
| 9-515 | Et | Ac | C—SO$_2$i-Pr | C—H | OCF$_3$ | Me | 0 | |
| 9-516 | Et | Ac | C—SO$_2$i-Pr | C—H | OCF$_3$ | Me | 1 | |
| 9-517 | Et | Ac | C—SO$_2$i-Pr | C—H | OCF$_3$ | Me | 2 | |
| 9-518 | Et | H | C—S—n-Bu | C—H | OCF$_3$ | Me | 0 | |
| 9-519 | Et | H | C—S—n-Bu | C—H | OCF$_3$ | Me | 1 | |
| 9-520 | Et | H | C—S—n-Bu | C—H | OCF$_3$ | Me | 2 | |
| 9-521 | Et | Ac | C—S—n-Bu | C—H | OCF$_3$ | Me | 0 | |
| 9-522 | Et | Ac | C—S—n-Bu | C—H | OCF$_3$ | Me | 1 | |
| 9-523 | Et | Ac | C—S—n-Bu | C—H | OCF$_3$ | Me | 2 | |
| 9-524 | Et | H | C—SO—n-Bu | C—H | OCF$_3$ | Me | 0 | |
| 9-525 | Et | H | C—SO—n-Bu | C—H | OCF$_3$ | Me | 1 | |

R$^4$, R$^5$ and R$^7$ each represent a hydrogen atom, and A$^1$ and A$^3$ each represent a CH group.

TABLE 9-22

| Compound No. | R$^1$ | R$^3$ | A$^2$ | A$^4$ | R$^6$ | Z | m | Physical property |
|---|---|---|---|---|---|---|---|---|
| 9-526 | Et | H | C—SO—n-Bu | C—H | OCF$_3$ | Me | 2 | |
| 9-527 | Et | Ac | C—SO—n-Bu | C—H | OCF$_3$ | Me | 0 | |
| 9-528 | Et | Ac | C—SO—n-Bu | C—H | OCF$_3$ | Me | 1 | |
| 9-529 | Et | Ac | C—SO—n-Bu | C—H | OCF$_3$ | Me | 2 | |
| 9-530 | Et | H | C—SO$_2$n-Bu | C—H | OCF$_3$ | Me | 0 | |
| 9-531 | Et | H | C—SO$_2$n-Bu | C—H | OCF$_3$ | Me | 1 | |
| 9-532 | Et | H | C—SO$_2$n-Bu | C—H | OCF$_3$ | Me | 2 | |
| 9-533 | Et | Ac | C—SO$_2$n-Bu | C—H | OCF$_3$ | Me | 0 | |
| 9-534 | Et | Ac | C—SO$_2$n-Bu | C—H | OCF$_3$ | Me | 1 | |
| 9-535 | Et | Ac | C—SO$_2$n-Bu | C—H | OCF$_3$ | Me | 2 | |
| 9-536 | Et | H | C—Si-Bu | C—H | OCF$_3$ | Me | 0 | |
| 9-537 | Et | H | C—Si-Bu | C—H | OCF$_3$ | Me | 1 | |
| 9-538 | Et | H | C—Si-Bu | C—H | OCF$_3$ | Me | 2 | |
| 9-539 | Et | Ac | C—Si-Bu | C—H | OCF$_3$ | Me | 0 | |
| 9-540 | Et | Ac | C—Si-Bu | C—H | OCF$_3$ | Me | 1 | |
| 9-541 | Et | Ac | C—Si-Bu | C—H | OCF$_3$ | Me | 2 | |
| 9-542 | Et | H | C—SO—i-BU | C—H | OCF$_3$ | Me | 0 | |
| 9-543 | Et | H | C—SO—i-BU | C—H | OCF$_3$ | Me | 1 | |
| 9-544 | Et | H | C—SO—i-BU | C—H | OCF$_3$ | Me | 2 | |
| 9-545 | Et | Ac | C—SO—i-BU | C—H | OCF$_3$ | Me | 0 | |
| 9-546 | Et | Ac | C—SO—i-BU | C—H | OCF$_3$ | Me | 1 | |
| 9-547 | Et | Ac | C—SO—i-BU | C—H | OCF$_3$ | Me | 2 | |

TABLE 9-22-continued

| Compound No. | R$^1$ | R$^3$ | A$^2$ | A$^4$ | R$^6$ | Z | m | Physical property |
|---|---|---|---|---|---|---|---|---|
| 9-548 | Et | H | C—SO$_2$i-Bu | C—H | OCF$_3$ | Me | 0 | |
| 9-549 | Et | H | C—SO$_2$i-Bu | C—H | OCF$_3$ | Me | 1 | |
| 9-550 | Et | H | C—SO$_2$i-Bu | C—H | OCF$_3$ | Me | 2 | |

R$^4$, R$^5$ and R$^7$ each represent a hydrogen atom, and A$^1$ and A$^3$ each represent a CH group.

TABLE 9-23

| Compound No. | R$^1$ | R$^3$ | A$^2$ | A$^4$ | R$^6$ | Z | m | Physical property |
|---|---|---|---|---|---|---|---|---|
| 9-551 | Et | Ac | C—SO$_2$i-Bu | C—H | OCF$_3$ | Me | 0 | |
| 9-552 | Et | Ac | C—SO$_2$i-Bu | C—H | OCF$_3$ | Me | 1 | |
| 9-553 | Et | Ac | C—SO$_2$i-Bu | C—H | OCF$_3$ | Me | 2 | |
| 9-554 | Et | H | C—Ss-Bu | C—H | OCF$_3$ | Me | 0 | |
| 9-555 | Et | H | C—Ss-Bu | C—H | OCF$_3$ | Me | 1 | |
| 9-556 | Et | H | C—Ss-Bu | C—H | OCF$_3$ | Me | 2 | |
| 9-557 | Et | Ac | C—Ss-Bu | C—H | OCF$_3$ | Me | 0 | |
| 9-558 | Et | Ac | C—Ss-Bu | C—H | OCF$_3$ | Me | 1 | |
| 9-559 | Et | Ac | C—Ss-Bu | C—H | OCF$_3$ | Me | 2 | |
| 9-560 | Et | H | C—SO—s-Bu | C—H | OCF$_3$ | Me | 0 | |
| 9-561 | Et | H | C—SO—s-Bu | C—H | OCF$_3$ | Me | 1 | |
| 9-562 | Et | H | C—SO—s-Bu | C—H | OCF$_3$ | Me | 2 | |
| 9-563 | Et | Ac | C—SO—s-Bu | C—H | OCF$_3$ | Me | 0 | |
| 9-564 | Et | Ac | C—SO—s-Bu | C—H | OCF$_3$ | Me | 1 | |
| 9-565 | Et | Ac | C—SO—s-Bu | C—H | OCF$_3$ | Me | 2 | |
| 9-566 | Et | H | C—SO$_2$s-Bu | C—H | OCF$_3$ | Me | 0 | |
| 9-567 | Et | H | C—SO$_2$s-Bu | C—H | OCF$_3$ | Me | 1 | |
| 9-568 | Et | H | C—SO$_2$s-Bu | C—H | OCF$_3$ | Me | 2 | |
| 9-569 | Et | Ac | C—SO$_2$s-Bu | C—H | OCF$_3$ | Me | 0 | |
| 9-570 | Et | Ac | C—SO$_2$s-Bu | C—H | OCF$_3$ | Me | 1 | |
| 9-571 | Et | Ac | C—SO$_2$s-Bu | C—H | OCF$_3$ | Me | 2 | |
| 9-572 | Et | H | C-St-Bu | C—H | OCF$_3$ | Me | 0 | |
| 9-573 | Et | H | C-St-Bu | C—H | OCF$_3$ | Me | 1 | |
| 9-574 | Et | H | C-St-Bu | C—H | OCF$_3$ | Me | 2 | |
| 9-575 | Et | Ac | C-St-Bu | C—H | OCF$_3$ | Me | 0 | |

R$^4$, R$^5$ and R$^7$ each represent a hydrogen atom, and A$^1$ and A$^3$ each represent a CH group.

TABLE 9-24

| Compound No. | R$^1$ | R$^3$ | A$^2$ | A$^4$ | R$^6$ | Z | m | Physical property |
|---|---|---|---|---|---|---|---|---|
| 9-576 | Et | Ac | C-St-Bu | C—H | OCF$_3$ | Me | 1 | |
| 9-577 | Et | Ac | C-St-Bu | C—H | OCF$_3$ | Me | 2 | |
| 9-578 | Et | H | C—SO—t-Bu | C—H | OCF$_3$ | Me | 0 | |
| 9-579 | Et | H | C—SO—t-Bu | C—H | OCF$_3$ | Me | 1 | |
| 9-580 | Et | H | C—SO—t-Bu | C—H | OCF$_3$ | Me | 2 | |
| 9-581 | Et | Ac | C—SO—t-Bu | C—H | OCF$_3$ | Me | 0 | |
| 9-582 | Et | Ac | C—SO—t-Bu | C—H | OCF$_3$ | Me | 1 | |
| 9-583 | Et | Ac | C—SO—t-Bu | C—H | OCF$_3$ | Me | 2 | |
| 9-584 | Et | H | C—SO$_2$t-Bu | C—H | OCF$_3$ | Me | 0 | |
| 9-585 | Et | H | C—SO$_2$t-Bu | C—H | OCF$_3$ | Me | 1 | |
| 9-586 | Et | H | C—SO$_2$t-Bu | C—H | OCF$_3$ | Me | 2 | |
| 9-587 | Et | Ac | C—SO$_2$t-Bu | C—H | OCF$_3$ | Me | 0 | |
| 9-588 | Et | Ac | C—SO$_2$t-Bu | C—H | OCF$_3$ | Me | 1 | |
| 9-589 | Et | Ac | C—SO$_2$t-Bu | C—H | OCF$_3$ | Me | 2 | |
| 9-590 | Et | H | C—CF$_3$ | C—OMe | OCF$_3$ | Me | 0 | |
| 9-591 | Et | H | C—CF$_3$ | C—OMe | OCF$_3$ | Me | 1 | |
| 9-592 | Et | H | C—CF$_3$ | C—OMe | OCF$_3$ | Me | 2 | |
| 9-593 | Et | Ac | C—CF$_3$ | C—OMe | OCF$_3$ | Me | 0 | |
| 9-594 | Et | Ac | C—CF$_3$ | C—OMe | OCF$_3$ | Me | 1 | |
| 9-595 | Et | Ac | C—CF$_3$ | C—OMe | OCF$_3$ | Me | 2 | |
| 9-596 | Et | H | C—CF$_3$ | C—OEt | OCF$_3$ | Me | 0 | |
| 9-597 | Et | H | C—CF$_3$ | C—OEt | OCF$_3$ | Me | 1 | |

TABLE 9-24-continued

| Compound No. | R¹ | R³ | A² | A⁴ | R⁶ | Z | m | Physical property |
|---|---|---|---|---|---|---|---|---|
| 9-598 | Et | H  | C—CF₃ | C—OEt | OCF₃ | Me | 2 | |
| 9-599 | Et | Ac | C—CF₃ | C—OEt | OCF₃ | Me | 0 | |
| 9-600 | Et | Ac | C—CF₃ | C—OEt | OCF₃ | Me | 1 | |

R⁴, R⁵ and R⁷ each represent a hydrogen atom, and A¹ and A³ each represent a CH group.

TABLE 9-25

| Compound No. | R¹ | R³ | A² | A⁴ | R⁶ | Z | m | Physical property |
|---|---|---|---|---|---|---|---|---|
| 9-601 | Et | Ac | C—CF₃ | C—OEt  | OCF₃ | Me | 2 | |
| 9-602 | Et | H  | C—CF₃ | C—On-Pr | OCF₃ | Me | 0 | |
| 9-603 | Et | H  | C—CF₃ | C—On-Pr | OCF₃ | Me | 1 | |
| 9-604 | Et | H  | C—CF₃ | C—On-Pr | OCF₃ | Me | 2 | |
| 9-605 | Et | Ac | C—CF₃ | C—On-Pr | OCF₃ | Me | 0 | |
| 9-606 | Et | Ac | C—CF₃ | C—On-Pr | OCF₃ | Me | 1 | |
| 9-607 | Et | Ac | C—CF₃ | C—On-Pr | OCF₃ | Me | 2 | |
| 9-608 | Et | H  | C—CF₃ | C—Oi-Pr | OCF₃ | Me | 0 | |
| 9-609 | Et | H  | C—CF₃ | C—Oi-Pr | OCF₃ | Me | 1 | |
| 9-610 | Et | H  | C—CF₃ | C—Oi-Pr | OCF₃ | Me | 2 | |
| 9-611 | Et | Ac | C—CF₃ | C—Oi-Pr | OCF₃ | Me | 0 | |
| 9-612 | Et | Ac | C—CF₃ | C—Oi-Pr | OCF₃ | Me | 1 | |
| 9-613 | Et | Ac | C—CF₃ | C—Oi-Pr | OCF₃ | Me | 2 | |
| 9-614 | Et | H  | C—CF₃ | C—On-Bu | OCF₃ | Me | 0 | |
| 9-615 | Et | H  | C—CF₃ | C—On-Bu | OCF₃ | Me | 1 | |
| 9-616 | Et | H  | C—CF₃ | C—On-Bu | OCF₃ | Me | 2 | |
| 9-617 | Et | Ac | C—CF₃ | C—On-Bu | OCF₃ | Me | 0 | |
| 9-618 | Et | Ac | C—CF₃ | C—On-Bu | OCF₃ | Me | 1 | |
| 9-619 | Et | Ac | C—CF₃ | C—On-Bu | OCF₃ | Me | 2 | |
| 9-620 | Et | H  | C—CF₃ | C—Oi-Bu | OCF₃ | Me | 0 | |
| 9-621 | Et | H  | C—CF₃ | C—Oi-Bu | OCF₃ | Me | 1 | |
| 9-622 | Et | H  | C—CF₃ | C—Oi-Bu | OCF₃ | Me | 2 | |
| 9-623 | Et | Ac | C—CF₃ | C—Oi-Bu | OCF₃ | Me | 0 | |
| 9-624 | Et | Ac | C—CF₃ | C—Oi-Bu | OCF₃ | Me | 1 | |
| 9-625 | Et | Ac | C—CF₃ | C—Oi-Bu | OCF₃ | Me | 2 | |

R⁴, R⁵ and R⁷ each represent a hydrogen atom, and A¹ and A³ each represent a CH group.

TABLE 9-26

| Compound No. | R¹ | R³ | A² | A⁴ | R⁶ | Z | m | Physical property |
|---|---|---|---|---|---|---|---|---|
| 9-626 | Et | H  | C—CF₃ | C—Os-Bu | OCF₃ | Me | 0 | |
| 9-627 | Et | H  | C—CF₃ | C—Os-Bu | OCF₃ | Me | 1 | |
| 9-628 | Et | H  | C—CF₃ | C—Os-Bu | OCF₃ | Me | 2 | |
| 9-629 | Et | Ac | C—CF₃ | C—Os-Bu | OCF₃ | Me | 0 | |
| 9-630 | Et | Ac | C—CF₃ | C—Os-Bu | OCF₃ | Me | 1 | |
| 9-631 | Et | Ac | C—CF₃ | C—Os-Bu | OCF₃ | Me | 2 | |
| 9-632 | Et | H  | C—CF₃ | C—Ot-Bu | OCF₃ | Me | 0 | |
| 9-633 | Et | H  | C—CF₃ | C—Ot-Bu | OCF₃ | Me | 1 | |
| 9-634 | Et | H  | C—CF₃ | C—Ot-Bu | OCF₃ | Me | 2 | |
| 9-635 | Et | Ac | C—CF₃ | C—Ot-Bu | OCF₃ | Me | 0 | |
| 9-636 | Et | Ac | C—CF₃ | C—Ot-Bu | OCF₃ | Me | 1 | |
| 9-637 | Et | Ac | C—CF₃ | C—Ot-Bu | OCF₃ | Me | 2 | |

R⁴, R⁵ and R⁷ each represent a hydrogen atom, and A¹ and A³ each represent a CH group.

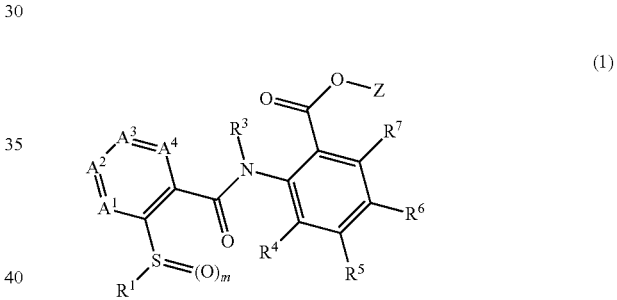

(1)

TABLE 10-1

| Compound No. | R¹ | A¹ | A² | A⁴ | R³ | R⁶ | Z | m | Physical property |
|---|---|---|---|---|---|---|---|---|---|
| 10-1  | Et | N   | C—CF₃ | C—H | H  | CF(CF₃)₂ | Me | 0 | 56-60 |
| 10-2  | Et | N   | C—CF₃ | C—H | H  | CF(CF₃)₂ | Me | 1 | |
| 10-3  | Et | N   | C—CF₃ | C—H | H  | CF(CF₃)₂ | Me | 2 | 143-145 |
| 10-4  | Et | N   | C—CF₃ | C—H | Ac | CF(CF₃)₂ | Me | 0 | |
| 10-5  | Et | N   | C—CF₃ | C—H | Ac | CF(CF₃)₂ | Me | 1 | |
| 10-6  | Et | N   | C—CF₃ | C—H | Ac | CF(CF₃)₂ | Me | 2 | 152-154 |
| 10-7  | Et | C—H | C—CF₃ | N   | COEt  | CF(CF₃)₂ | Me | 0 | |
| 10-8  | Et | C—H | C—CF₃ | N   | COEt  | CF(CF₃)₂ | Me | 1 | |
| 10-9  | Et | C—H | C—CF₃ | N   | COEt  | CF(CF₃)₂ | Me | 2 | |
| 10-10 | Et | C—H | C—CF₃ | N   | COi-Pr | CF(CF₃)₂ | Me | 0 | |
| 10-11 | Et | C—H | C—CF₃ | N   | COi-Pr | CF(CF₃)₂ | Me | 1 | |
| 10-12 | Et | C—H | C—CF₃ | N   | COi-Pr | CF(CF₃)₂ | Me | 2 | |
| 10-13 | Et | C—H | C—CF₃ | N   | H  | OCF₃ | Me | 0 | 164-165 |
| 10-14 | Et | C—H | C—CF₃ | N   | H  | OCF₃ | Me | 1 | |
| 10-15 | Et | C—H | C—CF₃ | N   | H  | OCF₃ | Me | 2 | 159-160 |

$R^4$, $R^5$ and $R^7$ each represent a hydrogen atom, and $A^3$ represents a CH group.

TABLE 10-2

| Compound No. | $R^1$ | $A^1$ | $A^2$ | $A^4$ | $R^3$ | $R^6$ | Z | m | Physical property |
|---|---|---|---|---|---|---|---|---|---|
| 10-16 | Et | C—H | C—$CF_3$ | N | Ac | $OCF_3$ | Me | 0 | |
| 10-17 | Et | C—H | C—$CF_3$ | N | Ac | $OCF_3$ | Me | 1 | |
| 10-18 | Et | C—H | C—$CF_3$ | N | Ac | $OCF_3$ | Me | 2 | 57-58 |
| 10-19 | Et | C—H | C—$CF_3$ | N | COEt | $OCF_3$ | Me | 0 | |
| 10-20 | Et | C—H | C—$CF_3$ | N | COEt | $OCF_3$ | Me | 1 | |
| 10-21 | Et | C—H | C—$CF_3$ | N | COEt | $OCF_3$ | Me | 2 | |
| 10-22 | Et | C—H | C—$CF_3$ | N | COi-Pr | $OCF_3$ | Me | 0 | |
| 10-23 | Et | C—H | C—$CF_3$ | N | COi-Pr | $OCF_3$ | Me | 1 | |
| 10-24 | Et | C—H | C—$CF_3$ | N | COi-Pr | $OCF_3$ | Me | 2 | 56-57 |
| 10-25 | Et | C—H | C—$CF_3$ | N | COEt | $OCF_3$ | Et | 0 | |
| 10-26 | Et | C—H | C—$CF_3$ | N | COEt | $OCF_3$ | Et | 1 | |
| 10-27 | Et | C—H | C—$CF_3$ | N | COEt | $OCF_3$ | Et | 2 | |
| 10-28 | Et | C—H | C—$CF_3$ | N | COi-Pr | $OCF_3$ | Et | 0 | |
| 10-29 | Et | C—H | C—$CF_3$ | N | COi-Pr | $OCF_3$ | Et | 1 | |
| 10-30 | Et | C—H | C—$CF_3$ | N | COi-Pr | $OCF_3$ | Et | 2 | |

$R^4$, $R^5$ and $R^7$ each represent a hydrogen atom, and $A^3$ represents a CH group.

TABLE 11

| Compound No. | $^1$H-NMR data ($CDCl_3$) |
|---|---|
| 4-28 | 8.23(d, 1H), 7.71(d, 1H), 7.58(d, 2H), 7.37(d, 2H), 3.99(s, 3H), 3.49(q, 1H), 2.31(s, 3H), 1.33(d, 6H) |
| 4-37 | 9.05(s, 1H), 8.13(d, 1H), 7.86(d, 1H), 7.67(d, 2H), 7.50(d, 2H), 5.99(dd, 1H), 5.78(ddt, 1H), 5.12(dd, 1H), 3.96(s, 3H), 3.30(dd, 2H). |
| 4-40 | 8.25(d, 1H), 8.12(d, 1H), 7.76(d, 2H), 7.52(d, 2H), 6.13(dd, 1H), 5.96(dd, 1H), 5.30(dd, 1H), 4.04(s, 3H), 3.44(dd, 2H), 2.36(s, 3H). |
| 4-52 | 8.33(d, 1H), 7.93(s, 1H), 7.85(d, 1H), 7.73-7.62(m, 3H), 3.97(s, 3H), 2.15(s, 3H), 1.29(s, 9H) |
| 5-57 | 8.21(s, 1H), 7.96(d, 1H), 7.87(d, 1H), 7.77(d, 1H), 7.67(d, 1H), 7.51(s, 1H), 3.97(s, 3H), 3.29(q, 2H), 2.06(s, 3H), 1.31(t, 3H) |
| 8-348 | 11.72 (s, 1H), 8.87 (d, 1H), 8.38 (s, 2H), 8.04 (d, 1H), 7.90 (dd, 1H), 7.84 (d, 1H), 3.94 (s, 3H), 3.62 (q, 2H), 1.37 (t, 3H) |

The agricultural and horticultural microbicide comprising the anthranilic acid ester compound represented by the general formula (1) of the present invention or a salt thereof as an active ingredient is suitable for controlling a variety of diseases which may damage cereals, fruit trees, vegetables, other crops and ornamental flowering plants.

The target diseases include filamentous fungal diseases, bacterial diseases and viral diseases. Examples of the filamentous fungal diseases include diseases caused by fungi-imperfecti including the genera *Botrytis, Helminthosporium, Fusarium, Septoria, Cercospora, Pseudocercosporella, Rhynchosporium, Pyricularia* and *Alternaria*; diseases caused by basidiomycetes including the genera *Hemilelia, Rhizoctonia, Ustilago, Typhula* and *Puccinia*; diseases caused by ascomycota including the genera *Venturia, Podosphaera, Leptosphaeria, Blumeria, Erysiphe, Microdochium, Sclerotinia, Gaeumannomyces, Monilinia* and *Unsinula*; and diseases caused by other fungi including the genera *Ascochyta, Phoma, Pythium, Corticium* and *Pyrenophora*. Examples of the bacterial diseases include diseases caused by bacteria including the genera *Pseudomonas, Xanthomonas* and *Erwinia*. Examples of the viral diseases include diseases caused by viruses including tobacco mosaic virus.

Specific examples of the filamentous fungal diseases include rice blast (*Pyricularia oryzae*), rice sheath blight (*Rhizoctonia solani*), rice brown spot (*Cochiobolus miyabeanus*), rice seedling blight (*Rhizopus chinensis, Pythium graminicola, Fusarium graminicola, Fusarium roseum, Mucor* sp., *Phoma* sp., *Tricoderma* sp.), rice bakanae disease (*Gibberella fujikuroi*), powdery mildew of barley, wheat, etc. (*Blumeria graminis*), powdery mildew of cucumbers etc. (*Sphaerotheca fuliginea*), powdery mildew of eggplants etc. (*Erysiphe cichoracoarum*), powdery mildew of other host plants, eyespot of barley, wheat, etc. (*Pseudocercosporella herpotrichoides*), smut of wheat etc. (*Urocystis tritici*), snow mold of barley, wheat, etc. (*Microdochiumnivalis, Pythium iwayamai, Typhla ishikariensis, Typhla incarnata, Sclerotinia borealis*), fusarium ear blight of barley, wheat, etc. (*Fusarium graminearum, Fusarium avenaceum, Fusarium culmorum, Microdochium nivalis*), rust of barley, wheat, etc. (*Puccinia recondita, Puccinia striiformis, Puccinia graminis*), take-all of barley, wheat, etc. (*Gaeumannomyces graminis*), oat crown rust (*Puccinia coronata*), rust of other plants, gray mold of cucumbers, strawberries, etc. (*Botrytis cinerea*), sclerotinia rot of tomatoes, cabbages, etc. (*Sclerotinia sclerotiorum*), late blight of potatoes, tomatoes, etc. (*Phytophthora infestans*), late blight of other plants, cucumber downy mildew (*Pseudoperonospora cubensis*), grape downy mildew (*Plasmopara viticola*), downy mildew of various plants, apple scab (*Venturia inaequalis*), apple alternaria blotch (*Alternaria mali*), pear black spot (*Alternaria kikuchiana*), citrus melanose (*Diaporthe citri*), citrus scab (*Elsinoe fawcetti*), sugarbeet leaf spot (*Cercospora beticola*), peanut brown leaf spot (*Cercospora arachidicola*), peanut late leaf spot (*Cercospora personata*), leaf blotch of wheat (*Septoria tritici*), wheat glume blotch (*Leptosphaeria nodorum*), barley net blotch (*Pyrenophora teres*), barley stripe (*Pyrenophora graminea*), barley scald (*Rhynchosporium secalis*), wheat loose smut (*Ustilago nuda*), wheat stinking smut (*Tilletia caries*), brown patch of turfgrass (*Rhizoctonia solani*) and dollar spot of turfgrass (*Sclerotinia homoeocarpa*).

Specific examples of the bacterial diseases include diseases caused by *Pseudomonas* spp. such as cucumber bacterial spot (*Pseudomonas syringae* pv. *lachrymans*), tomato bacterial wilt disease (*Pseudomonas solanacearum*) and bacterial grain rot of rice (*Pseudomonas glumae*); diseases caused by *Xanthomonas* spp. such as cabbage black rot (*Xanthomonas campestris*), rice bacterial leaf blight (*Xanthomonas oryzae*) and citrus canker (*Xanthomonas citri*); and diseases caused by *Erwinia* spp. such as cabbage soft rot (*Erwinia carotovora*).

In particular, the agricultural and horticultural microbicide of the present invention is highly effective against powdery mildew of barley, wheat, etc. (*Blumeria graminis*), powdery mildew of cucumbers etc. (*Sphaerotheca fuliginea*), powdery mildew of eggplants etc. (*Erysiphe cichoracoarum*), powdery mildew of grapes etc. (*Erysiphe necator*), powdery mildew of apples etc. (*Podosphaera leucotricha*), powdery mildew of strawberries etc. (*Spaerotheca aphanis*) and powdery mildew of other host plants.

In addition, the agricultural and horticultural microbicide is expected to be highly effective against powdery mildew fungi less sensitive to existing microbicides.

The agricultural and horticultural microbicide comprising the anthranilic acid ester compound represented by the general formula (1) of the present invention or a salt thereof as an active ingredient has a remarkable control effect on the above-described diseases which damage lowland crops, field crops, fruit trees, vegetables, other crops, ornamental flowering plants, etc. The desired effect can be obtained when the agricultural and horticultural microbicide is applied to nursery facilities for seedlings, paddy fields, fields, seeds and foliage of fruit trees, vegetables, other crops, ornamental flowering plants, etc., paddy water, cultivation media such as soil, or the like around the expected time of disease infestation, i.e., before the infestation or upon the confirmation of the infestation. In particularly preferable embodiments, the application of the agricultural and horticultural microbicide utilizes so-called penetration and translocation. That is, the agricultural and horticultural microbicide is applied to nursery soil, soil in transplanting holes, plant foot, irrigation water, cultivation water in hydroponics, or the like to allow crops, ornamental flowering plants, etc. to absorb the compound of the present invention through the roots via soil or otherwise.

The useful plants to which the agricultural and horticultural microbicide of the present invention can be applied include, but are not particularly limited to, for example, cereals (e.g., rice, barley, wheat, rye, oats, corn, etc.), legumes (e.g., soybeans, azuki beans, broad beans, green peas, kidneybeans, peanuts, etc.), fruit trees and fruits (e.g., apples, citrus fruits, pears, grapes, peaches, plums, cherries, walnuts, chestnuts, almonds, bananas, etc.), leaf and fruit vegetables (e.g., cabbages, tomatoes, spinach, broccoli, lettuce, onions, green onions (chives and Welsh onions), green peppers, eggplants, strawberries, pepper crops, okra, Chinese chives, etc.), root vegetables (e.g., carrots, potatoes, sweet potatoes, taros, Japanese radishes, turnips, lotus roots, burdock roots, garlic, Chinese scallions, etc.), crops for processing (e.g., cotton, hemp, beet, hops, sugarcane, sugar beet, olives, rubber, coffee, tobacco, tea, etc.), gourds (e.g., Japanese pumpkins, cucumbers, watermelons, oriental sweet melons, melons, etc.), pasture grass (e.g., orchardgrass, *sorghum*, timothy, clover, alfalfa, etc.), lawn grass (e.g., Korean lawn grass, bent grass, etc.), spice and aromatic crops and ornamental crops (e.g., lavender, rosemary, thyme, parsley, pepper, ginger, etc.), ornamental flowering plants (e.g., chrysanthemum, rose, carnation, orchid, tulip, lily, etc.), garden trees (e.g., ginkgo trees, cherry trees, Japanese aucuba, etc.) and forest trees (e.g., *Abies sachalinensis, Picea jezoensis*, pine, yellow cedar, Japanese cedar, hinoki cypress, eucalyptus, etc.). Particularly, the agricultural and horticultural microbicide of the present invention is preferably applied to cereals, fruit trees and fruits, and leaf and fruit vegetables.

The above-mentioned "plants" also include plants provided with herbicide tolerance by a classical breeding technique or a gene recombination technique. Examples of such herbicide tolerance include tolerance to HPPD inhibitors, such as isoxaflutole; ALS inhibitors, such as imazethapyr and thifensulfuron-methyl; EPSP synthase inhibitors, such as glyphosate; glutamine synthetase inhibitors, such as glufosinate; acetyl-CoA carboxylase inhibitors, such as sethoxydim; or other herbicides, such as bromoxynil, dicamba and 2,4-D.

Examples of the plants provided with herbicide tolerance by a classical breeding technique include varieties of rapeseed, wheat, sunflower and rice tolerant to the imidazolinone family of ALS-inhibiting herbicides such as imazethapyr, and such rice plants are sold under the trade name of Clearfield (registered trademark). Also included is a variety of soybean provided with tolerance to the sulfonyl urea family of ALS-inhibiting herbicides such as thifensulfuron-methyl by a classical breeding technique, and this is sold under the trade name of STS soybean. Also included are plants provided with tolerance to acetyl-CoA carboxylase inhibitors such as trione oxime herbicides and aryloxy phenoxy propionic acid herbicides by a classical breeding technique, for example, SR corn and the like.

Plants provided with tolerance to acetyl-CoA carboxylase inhibitors are described in Proc. Natl. Acad. Sci. USA, 87, 7175-7179 (1990), and the like. Further, acetyl-CoA carboxylase mutants resistant to acetyl-CoA carboxylase inhibitors are reported in Weed Science, 53, 728-746 (2005), and the like, and by introducing the gene of such an acetyl-CoA carboxylase mutant into plants by a gene recombination technique, or introducing a resistance-conferring mutation into acetyl-CoA carboxylase of plants, plants tolerant to acetyl-CoA carboxylase inhibitors can be engineered. Alternatively, by introducing a nucleic acid causing base substitution mutation into plant cells (a typical example of this technique is chimeraplasty technique (Gura T. 1999. Repairing the Genome's Spelling Mistakes. Science 285: 316-318.)) to allow site-specific substitution mutation in the amino acids encoded by an acetyl-CoA carboxylase gene, an ALS gene or the like of plants, plants tolerant to acetyl-CoA carboxylase inhibitors, ALS inhibitors or the like can be engineered. The agricultural and horticultural microbicide of the present invention can be applied to these plants as well.

Further, exemplary toxins expressed in genetically modified plants include insecticidal proteins derived from *Bacillus cereus* or *Bacillus popilliae; Bacillus thuringiensis*-derived δ-endotoxins, such as Cry1Ab, Cry1Ac, Cry1F, Cry1Fa2, Cry2Ab, Cry3A, Cry3Bb1 and Cry9C, and other insecticidal proteins, such as VIP1, VIP2, VIP3 and VIP3A; nematode-derived insecticidal proteins; toxins produced by animals, such as scorpion toxins, spider toxins, bee toxins and insect-specific neurotoxins; toxins of filamentous fungi; plant lectins; agglutinin; protease inhibitors, such as trypsin inhibitors, serine protease inhibitors, patatin, cystatin and papain inhibitors; ribosome inactivating proteins (RIP), such as ricin, maize RIP, abrin, luffin, saporin and bryodin; steroid metabolizing enzymes, such as 3-hydroxy steroid oxidase, ecdysteroid-UDP-glucosyltransferase and cholesterol oxidase; ecdysone inhibitors; HMG-CoA reductase; ion channel inhibitors, such as sodium channel inhibitors and calcium channel inhibitors; juvenile hormone esterase; diuretic hormone receptors; stilbene synthase; bibenzyl synthase; chitinase; and glucanase.

Also included are hybrid toxins, partially deficient toxins and modified toxins derived from the following: δ-endotoxin proteins such as Cry1Ab, Cry1Ac, Cry1F, Cry1Fa2, Cry2Ab, Cry3A, Cry3Bb1, Cry9C, Cry34Ab and Cry35Ab, and other insecticidal proteins such as VIP1, VIP2, VIP3 and VIP3A. The hybrid toxin can be produced by combining domains derived from these proteins differently from the original combination in nature with the use of a recombination technique. As the partially deficient toxin, a Cry1Ab toxin in which a part of the amino acid sequence is deleted is known. In the modified toxin, one or more amino acids of a naturally occurring toxin are substituted.

Examples of the foregoing toxins and genetically modified plants capable of synthesizing these toxins are described in EP-A-0 374 753, WO 93/07278, WO 95/34656, EP-A-0 427 529, EP-A-451 878, WO 03/052073, etc.

The above-described technologies and the agricultural and horticultural microbicide of the present invention can be used in combination or used systematically.

In order to control various diseases, the agricultural and horticultural microbicide of the present invention, with or without appropriate dilution or suspension in water etc., is applied to plants potentially infested with diseases in an amount effective for the control of the diseases. For example, in order to control diseases that may damage crop plants such as fruit trees, cereals and vegetables, foliar application and seed treatment such as dipping, dust coating and calcium peroxide coating can be performed. Further, treatment of soil or the like may also be performed to allow plants to absorb agrochemicals through their roots. Examples of such treatment include whole soil incorporation, planting row treatment, bed soil incorporation, plug seedling treatment, planting hole treatment, plant foot treatment, top-dressing, treatment of nursery boxes for paddy rice, and submerged application. In addition, application to culture media in hydroponics, smoking treatment, trunk injection and the like can also be performed.

Further, the agricultural and horticultural microbicide of the present invention, with or without appropriate dilution or suspension in water etc., can be applied to sites potentially infested with diseases in an amount effective for control of the diseases.

Exemplary methods of seed treatment include dipping of seeds in a diluted or undiluted fluid of a liquid or solid formulation for the permeation of agrochemicals into the seeds; mixing or dust coating of seeds with a solid or liquid formulation for the adherence of the formulation onto the surfaces of the seeds; coating of seeds with a mixture of a solid or liquid formulation and an adhesive carrier such as resins and polymers; and application of a solid or liquid formulation to the vicinity of seeds at the same time as seeding.

The term "seed" in the above-mentioned seed treatment refers to a plant body which is in the early stages of cultivation and used for plant propagation. The examples include, in addition to a so-called seed, a plant body for vegetative propagation, such as a bulb, a tuber, a seed potato, a bulbil, a propagule, a discoid stem and a stem used for cuttage.

The term "soil" or "cultivation medium" in the method of the present invention for using an agricultural and horticultural microbicide refers to a support medium for crop cultivation, in particular a support medium which allows crop plants to spread their roots therein, and the materials are not particularly limited as long as they allow plants to grow. Examples of the support medium include what is called soils, seedling mats and water, and specific examples of the materials include sand, pumice, vermiculite, diatomite, agar, gelatinous substances, high-molecular-weight substances, rock wool, glass wool, wood chip and bark.

Exemplary methods of the application to crop foliage etc. include application of a liquid formulation, such as an emulsifiable concentrate and a flowable, or a solid formulation, such as a wettable powder and a water-dispersible granule, after appropriate dilution in water; dust application; and smoking.

Exemplary methods of soil application include application of a water-diluted or undiluted liquid formulation to the foot of plants, nursery beds for seedlings, or the like; application of a granule to the foot of plants, nursery beds for seedlings, or the like; application of a dust, a wettable powder, a water-dispersible granule, a granule or the like onto soil and subsequent incorporation of the formulation into the whole soil before seeding or transplanting; and application of a dust, a wettable powder, a water-dispersible granule, a granule or the like to planting holes, planting rows or the like before seeding or planting.

To nursery boxes for paddy rice, for example, a dust, a water-dispersible granule, a granule or the like can be applied, although the suitable formulation may vary depending on the application time, in other words, depending on the cultivation stage such as seeding time, greening period and planting time. A formulation such as a dust, a water-dispersible granule, a granule or the like may be mixed with nursery soil. For example, such a formulation is incorporated into bed soil, covering soil or the whole soil. Simply, nursery soil and such a formulation may be alternately layered.

In the application to paddy fields, a solid formulation, such as a jumbo, a pack, a granule and a water-dispersible granule, or a liquid formulation, such as a flowable and an emulsifiable concentrate, is applied usually to flooded paddy fields. In a rice planting period, a suitable formulation, as it is or after mixed with a fertilizer or the like, may be applied onto soil or injected into soil. In addition, a solution of an emulsifiable concentrate, a flowable or the like may be applied to the source of water supply for paddy fields, such as a water inlet and an irrigation device. In this case, treatment can be accomplished with the supply of water and thus achieved in a labor-saving manner.

In the case of field crops, their seeds, cultivation media in the vicinity of their plants, or the like may be treated in the period of seeding to seedling culture. In the case of plants of which the seeds are directly sown in the field, in addition to direct seed treatment, plant foot treatment during cultivation is preferable. Specifically, the treatment can be performed by, for example, applying a granule onto soil, or drenching soil with a formulation in a water-diluted or undiluted liquid form. Another preferable treatment is incorporation of a granule into cultivation media before seeding.

In the case of culture plants to be transplanted, preferable examples of the treatment in the period of seeding to seedling culture include, in addition to direct seed treatment, drench treatment of nursery beds for seedlings with a formulation in a liquid form; and granule application to nursery beds for seedlings. Also included are treatment of planting holes with a granule; and incorporation of a granule into cultivation media in the vicinity of planting points at the time of fix planting.

The agricultural and horticultural microbicide of the present invention is commonly used as a formulation convenient for application, which is prepared in the usual method for preparing agrochemical formulations.

That is, the anthranilic acid ester compound represented by the general formula (1) of the present invention or a salt thereof and an appropriate inactive carrier, and if needed an adjuvant, are blended in an appropriate ratio, and through the step of dissolution, separation, suspension, mixing, impregnation, adsorption and/or adhesion, are formulated into an appropriate form for application, such as a suspension concentrate, an emulsifiable concentrate, a soluble concentrate, a wettable powder, a water-dispersible granule, a granule, a dust, a tablet and a pack.

The agricultural and horticultural microbicide of the present invention can optionally contain an additive usually used for agrochemical formulations in addition to the active ingredient. Examples of the additive include carriers such as solid or liquid carriers, surfactants, dispersants, wetting agents, binders, tackifiers, thickeners, colorants, spreaders, sticking/spreading agents, antifreezing agents, anti-caking agents, disintegrants and stabilizing agents. If needed, preservatives, plant fragments, etc. may also be used as the additive. These additives may be used alone or in a combination of two or more kinds.

Examples of the solid carriers include natural minerals, such as quartz, clay, kaolinite, pyrophyllite, sericite, talc, bentonite, acid clay, attapulgite, zeolite and diatomite; inorganic salts, such as calcium carbonate, ammonium sulfate, sodium sulfate and potassium chloride; organic solid carriers, such as synthetic silicic acid, synthetic silicates, starch, cellulose and plant powders (for example, sawdust, coconut shell, corn cob, tobacco stalk, etc.); plastics carriers, such as polyethylene, polypropylene and polyvinylidene chloride; urea; hollow inorganic materials; hollow plastic materials; and fumed silica (white carbon). These solid carriers may be used alone or in a combination of two or more kinds.

Examples of the liquid carriers include alcohols including monohydric alcohols, such as methanol, ethanol, propanol, isopropanol and butanol, and polyhydric alcohols, such as ethylene glycol, diethylene glycol, propylene glycol, hexylene glycol, polyethylene glycol, polypropylene glycol and glycerin; polyol compounds, such as propylene glycol ether; ketones, such as acetone, methyl ethyl ketone, methyl isobutyl ketone, diisobutyl ketone and cyclohexanone; ethers, such as ethyl ether, dioxane, ethylene glycol monoethyl ether, dipropyl ether and tetrahydrofuran; aliphatic hydrocarbons, such as normal paraffin, naphthene, isoparaffin, kerosene and mineral oil; aromatic hydrocarbons, such as benzene, toluene, xylene, solvent naphtha and alkyl naphthalene; halogenated hydrocarbons, such as dichloromethane, chloroform and carbon tetrachloride; esters, such as ethyl acetate, diisopropyl phthalate, dibutyl phthalate, dioctyl phthalate and dimethyl adipate; lactones, such as γ-butyrolactone; amides, such as dimethylformamide, diethylformamide, dimethylacetamide and N-alkyl pyrrolidinone; nitriles, such as acetonitrile; sulfur compounds, such as dimethyl sulfoxide; vegetable oils, such as soybean oil, rapeseed oil, cotton seed oil and castor oil; and water. These liquid carriers may be used alone or in a combination of two or more kinds.

Exemplary surfactants used as the dispersant or the wetting/spreading agent include nonionic surfactants, such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkyl aryl ether, polyoxyethylene alkyl phenyl ether, polyoxyethylene dialkyl phenyl ether, polyoxyethylene alkyl phenyl ether-formaldehyde condensates, polyoxyethylene-polyoxypropylene block copolymers, polystyrene-polyoxyethylene block polymers, alkyl polyoxyethylene-polypropylene block copolymer ether, polyoxyethylene alkylamine, polyoxyethylene fatty acid amide, polyoxyethylene fatty acid bis(phenyl ether), polyalkylene benzyl phenyl ether, polyoxyalkylene styryl phenyl ether, acetylene diol, polyoxyalkylene-added acetylene diol, polyoxyethylene ether-type silicone, ester-type silicone, fluorosurfactants, polyoxyethylene castor oil and polyoxyethylene hydrogenated castor oil; anionic surfactants, such as alkyl sulfates, polyoxyethylene alkyl ether sulfates, polyoxyethylene alkyl phenyl ether sulfates, polyoxyethylene styryl phenyl ether sulfates, alkylbenzene sulfonates, alkylaryl sulfonates, lignosulfonates, alkyl sulfosuccinates, naphthalene sulfonates, alkylnaphthalene sulfonates, salts of naphthalenesulfonic acid-formaldehyde condensates, salts of alkylnaphthalenesulfonic acid-formaldehyde condensates, fatty acid salts, polycarboxylic acid salts, polyacrylates, N-methyl-fatty acid sarcosinates, resinates, polyoxyethylene alkyl ether phosphates and polyoxyethylene alkyl phenyl ether phosphates; cationic surfactants including alkyl amine salts, such as lauryl amine hydrochloride, stearyl amine hydrochloride, oleyl amine hydrochloride, stearyl amine acetate, stearyl aminopropyl amine acetate, alkyl trimethyl ammonium chloride and alkyl dimethyl benzalkonium chloride; and amphoteric surfactants, such as amino acid-type or betaine-type amphoteric surfactants. These surfactants may be used alone or in a combination of two or more kinds.

Examples of the binders or the tackifiers include carboxymethyl cellulose or salts thereof, dextrin, soluble starch, xanthan gum, guar gum, sucrose, polyvinyl pyrrolidone, gum arabic, polyvinyl alcohol, polyvinyl acetate, sodium polyacrylate, polyethylene glycols with an average molecular weight of 6,000 to 20,000, polyethylene oxides with an average molecular weight of 100,000 to 5,000,000, phospholipids (for example, cephalin, lecithin, etc.), cellulose powder, dextrin, modified starch, polyaminocarboxylic acid chelating compounds, cross-linked polyvinyl pyrrolidone, maleic acid-styrene copolymers, (meth)acrylic acid copolymers, half esters of polyhydric alcohol polymer and dicarboxylic anhydride, water soluble polystyrene sulfonates, paraffin, terpene, polyamide resins, polyacrylates, polyoxyethylene, waxes, polyvinyl alkyl ether, alkylphenol-formaldehyde condensates and synthetic resin emulsions.

Examples of the thickeners include water soluble polymers, such as xanthan gum, guar gum, diutan gum, carboxymethyl cellulose, polyvinyl pyrrolidone, carboxyvinyl polymers, acrylic polymers, starch compounds and polysaccharides; and inorganic fine powders, such as high grade bentonite and fumed silica (white carbon).

Examples of the colorants include inorganic pigments, such as iron oxide, titanium oxide and prussian blue; and organic dyes, such as alizarin dyes, azo dyes and metal phthalocyanine dyes.

Examples of the antifreezing agents include polyhydric alcohols, such as ethylene glycol, diethylene glycol, propylene glycol and glycerin.

Examples of the adjuvants serving to prevent caking or facilitate disintegration include polysaccharides (starch, alginic acid, mannose, galactose, etc.), polyvinyl pyrrolidone, fumed silica (white carbon), ester gum, petroleum resin, sodium tripolyphosphate, sodium hexametaphosphate, metal stearates, cellulose powder, dextrin, methacrylate copolymers, polyvinyl pyrrolidone, polyaminocarboxylic acid chelating compounds, sulfonated styrene-isobutylene-maleic anhydride copolymers and starch-polyacrylonitrile graft copolymers.

Examples of the stabilizing agents include desiccants, such as zeolite, quicklime and magnesium oxide; antioxidants, such as phenolic compounds, amine compounds, sulfur compounds and phosphoric acid compounds; and ultraviolet absorbers, such as salicylic acid compounds and benzophenone compounds.

Examples of the preservatives include potassium sorbate and 1,2-benzothiazolin-3-one.

Further, other adjuvants including functional spreading agents, activity enhancers such as metabolic inhibitors (piperonyl butoxide etc.), antifreezing agents (propylene glycol etc.), antioxidants (BHT etc.) and ultraviolet absorbers can also be used if needed.

The content of the active ingredient compound in the agricultural and horticultural microbicide of the present invention can be adjusted as needed, and for example, is appropriately selected from the range of 0.01 to 90 parts by weight in 100 parts by weight of the agricultural and horticultural microbicide. For example, in the case where the agricultural and horticultural microbicide is a dust, a granule, an emulsifiable concentrate or a wettable powder, it is suitable that the content of the active ingredient compound is 0.01 to 50 parts by weight (0.01 to 50% by weight relative to the total weight of the agricultural and horticultural microbicide).

The application amount of the agricultural and horticultural microbicide of the present invention may vary with various factors, for example, the purpose, the target disease, the growing conditions of crops, the tendency of disease infestation, the weather, the environmental conditions, the dosage form, the application method, the application site, the application time, etc., but for example, the application amount of the active ingredient compound per 10 ares is appropriately selected from the range of 0.001 g to 10 kg, and preferably 0.01 g to 1 kg depending on the purpose.

Furthermore, for the expansion of the range of target diseases and the appropriate application time for disease control, or for dose reduction, the agricultural and horticultural microbicide of the present invention can be used after mixed with other agricultural and horticultural insecticides, acaricides, nematicides, microbicides, biopesticides and/or the like. Further, the agricultural and horticultural microbicide can be used after mixed with herbicides, plant growth regulators, fertilizers and/or the like depending on its application.

Examples of such additional agricultural and horticultural insecticides, acaricides and nematicides used for the above-mentioned purposes include 3,5-xylyl methylcarbamate (XMC), crystalline protein toxins produced by *Bacillus thuringiensis* such as *Bacillus thuringiensis aizawai, Bacillus thuringiensisisraelensis, Bacillus thuringiensis japonensis, Bacillus thuringiensis kurstaki* and *Bacillus thuringiensis tenebrionis*, BPMC, Bt toxin-derived insecticidal compounds, chlorfenson (CPCBS), dichlorodiisopropyl ether (DCIP), 1,3-dichloropropene (D-D), DDT, NAC, O-4-dimethylsulfamoylphenyl O,O-diethyl phosphorothioate (DSP), O-ethyl O-4-nitrophenyl phenylphosphonothioate (EPN), tripropylisocyanurate (TPIC), acrinathrin, azadirachtin, azinphos-methyl, acequinocyl, acetamiprid, acetoprole, acephate, abamectin, avermectin-B, amidoflumet, amitraz, alanycarb, aldicarb, aldoxycarb, aldrin, alpha-endosulfan, alpha-cypermethrin, albendazole, allethrin, isazofos, isamidofos, isoamidofos, isoxathion, isofenphos, isoprocarb (MIPC), ivermectin, imicyafos, imidacloprid, imiprothrin, indoxacarb, esfenvalerate, ethiofencarb, ethion, ethiprole, etoxazole, ethofenprox, ethoprophos, etrimfos, emamectin, emamectin-benzoate, endosulfan, empenthrin, oxamyl, oxydemeton-methyl, oxydeprofos (ESP), oxibendazole, oxfendazole, potassium oleate, sodium oleate, cadusafos, cartap, carbaryl, carbosulfan, carbofuran, gamma-cyhalothrin, xylylcarb, quinalphos, kinoprene, chinomethionat, cloethocarb, clothianidin, clofentezine, chromafenozide, chlorantraniliprole, chlorethoxyfos, chlordimeform, chlordane, chlorpyrifos, chlorpyrifos-methyl, chlorphenapyr, chlorfenson, chlorfenvinphos, chlorfluazuron, chlorobenzilate, chlorobenzoate, kelthane (dicofol), salithion, cyanophos (CYAP), diafenthiuron, diamidafos, cyantraniliprole, theta-cypermethrin, dienochlor, cyenopyrafen, dioxabenzofos, diofenolan, sigma-cypermethrin, dichlofenthion (ECP), cycloprothrin, dichlorvos (DDVP), disulfoton, dinotefuran, cyhalothrin, cyphenothrin, cyfluthrin, diflubenzuron, cyflumetofen, diflovidazin, cyhexatin, cypermethrin, dimethylvinphos, dimethoate, dimefluthrin, silafluofen, cyromazine, spinetoram, spinosad, spirodiclofen, spirotetramat, spiromesifen, sulfluramid, sulprofos, sulfoxaflor, zeta-cypermethrin, diazinon, tau-fluvalinate, dazomet, thiacloprid, thiamethoxam, thiodicarb, thiocyclam, thiosultap, thiosultap-sodium, thionazin, thiometon, deet, dieldrin, tetrachlorvinphos, tetradifon, tetramethylfluthrin, tetramethrin, tebupirimfos, tebufenozide, tebufenpyrad, tefluthrin, teflubenzuron, demeton-S-methyl, temephos, deltamethrin, terbufos, tralopyril, tralomethrin, transfluthrin, triazamate, triazuron, trichlamide, trichlorphon (DEP), triflumuron, tolfenpyrad, naled (BRP), nithiazine, nitenpyram, novaluron, noviflumuron, hydroprene, vaniliprole, vamidothion, parathion, parathion-methyl, halfenprox, halofenozide, bistrifluron, bisultap, hydramethylnon, hydroxy propyl starch, binapacryl, bifenazate, bifenthrin, pymetrozine, pyraclofos, pyrafluprole, pyridafenthion, pyridaben, pyridalyl, pyrifluquinazon, pyriprole, pyriproxyfen, pirimicarb, pyrimidifen, pirimiphos-methyl, pyrethrins, fipronil, fenazaquin, fenamiphos, phenisobromolate, fenitrothion (MEP), fenoxycarb, fenothiocarb, phenothrin, fenobucarb, fensulfothion, fenthion (MPP), phenthoate (PAP), fenvalerate, fenpyroximate, fenpropathrin, fenbendazole, fosthiazate, formetanate, butathiofos, buprofezin, furathiocarb, prallethrin, fluacrypyrim, fluazinam, fluazuron, fluensulfone, flucycloxuron, flucythrinate, fluvalinate, flupyrazofos, flufenerim, flufenoxuron, flufenzine, flufenprox, fluproxyfen, flubrocythrinate, flubendiamide, flumethrin, flurimfen, prothiofos, protrifenbute, flonicamid, propaphos, propargite (BPPS), profenofos, profluthrin, propoxur (PHC), bromopropylate, beta-cyfluthrin, hexaflumuron, hexythiazox, heptenophos, permethrin, benclothiaz, bendiocarb, bensultap, benzoximate, benfuracarb, phoxim, phosalone, fosthiazate, fosthietan, phosphamidon, phosphocarb, phosmet (PMP), polynactins, formetanate, formothion, phorate, machine oil, malathion, milbemycin, milbemycin-A, milbemectin, mecarbam, mesulfenfos, methomyl, metaldehyde, metaflumizone, methamidophos, metam-ammonium, metam-sodium, methiocarb, methidathion (DMTP), methylisothiocyanate, methylneodecanamide, methylparathion, metoxadiazone, methoxychlor, methoxyfenozide, metofluthrin, methoprene, metolcarb, meperfluthrin, mevinphos, monocrotophos, monosultap, lambda-cyhalothrin, ryanodine, lufenuron, resmethrin, lepimectin, rotenone, levamisole hydrochloride, fenbutatin oxide, morantel tartarate, methyl bromide, tricyclohexyltin hydroxide (cyhexatin), calcium cyanamide, calcium polysulfide, sulfur and nicotine-sulfate.

Examples of the agricultural and horticultural microbicides used for the same purposes as above include aureofungin, azaconazole, azithiram, acypetacs, acibenzolar, acibenzolar-S-methyl, azoxystrobin, anilazine, amisulbrom, ampropylfos, ametoctradin, allyl alcohol, aldimorph, amobam, isotianil, isovaledione, isopyrazam, isoprothiolane, ipconazole, iprodione, iprovalicarb, iprobenfos, imazalil, iminoctadine, iminoctadine-albesilate, iminoctadine-triacetate, imibenconazole, uniconazole, uniconazole-P, echlomezole, edifenphos, etaconazole, ethaboxam, ethirimol, etem, ethoxyquin, etridiazole, enestroburin, epoxiconazole, oxadixyl, oxycarboxin, copper-8-quinolinolate, oxytetracycline, copper-oxinate, oxpoconazole, oxpoconazole-fumarate, oxolinic acid, octhilinone, ofurace, orysastrobin, metam-sodium, kasugamycin, carbamorph, carpropamid, carbendazim, carboxin, carvone, quinazamid, quinacetol, quinoxyfen, quinomethionate, captafol, captan, kiralaxyl, quinconazole, quintozene, guazatine, cufraneb, cuprobam, glyodin, griseofulvin, climbazole, cresol, kresoxim-methyl, chlozolinate, clotrimazole, chlobenthiazone, chloraniformethan, chloranil, chlorquinox, chloropicrin, chlorfenazole, chlorodinitronaphthalene, chlorothalonil, chloroneb, zarilamid, salicylanilide, cyazofamid, diethyl pyrocarbonate, diethofencarb, cyclafuramid, diclocymet, dichlozoline, diclobutrazol, dichlofluanid, cycloheximide, diclomezine, dicloran, dichlorophen, dichlone, disulfiram, ditalimfos, dithianon, diniconazole, diniconazole-M, zineb, dinocap, dinocton, dinosulfon, dinoterbon, dinobuton, dinopenton, dipyrithione, diphenylamine, difenoconazole, cyflufenamid, diflumetorim, cyproconazole, cyprodinil, cyprofuram, cypendazole, simeconazole, dimethirimol, dimethomorph, cymoxanil, dimoxystrobin, methyl bromide, ziram, silthiofam, streptomycin, spiroxamine, sultropen, sedaxane, zoxamide, dazomet, thiadiazin, tiadinil, thiadifluor, thiabendazole, tioxymid, thiochlorfenphim, thiophanate, thiophanate-methyl, thicyofen, thioquinox, chinomethionat, thifluzamide, thiram, decafentin, tecnazene, tecloftalam, tecoram, tetraconazole, debacarb, dehydroacetic acid, tebuconazole, tebufloquin, dodicin, dodine, dodecyl benzensulfonate bisethylene diamine copper(II) (DBEDC), dodemorph, drazoxolon, triadimenol, triadimefon, triazbutil, triazoxide, triamiphos, triarimol, trichlamide, tricyclazole, triticonazole, tridemorph, tributyltin oxide, triflumizole, trifloxystrobin, triforine, tolylfluanid, tolclofos-methyl, natamycin, nabam, nitrothal-isopropyl, nitrostyrene, nuarimol, copper nonylphenol sulfonate, halacrinate, validamycin, valifenalate, harpin protein, bixafen, picoxystrobin, picobenzamide, bithional, bitertanol, hydroxyisoxazole, hydroxyisoxazole-potassium, binapacryl, biphenyl, piperalin, hymexazol, pyraoxystrobin, pyracarbolid, pyraclostrobin, pyrazophos, pyrametostrobin, pyriofenone, pyridinitril, pyrifenox, pyribencarb, pyrimethanil, pyroxychlor, pyroxyfur, pyroquilon, vinclozolin, famoxadone, fenapanil, fenamidone, fenaminosulf, fenarimol, fenitropan, fenoxanil, ferimzone, ferbam, fentin, fenpiclonil, fenpyrazamine, fenbuconazole, fenfuram, fenpropidin, fenpropimorph, fenhexamid, phthalide, buthiobate, butylamine, bupirimate, fuberidazole, blasticidin-S, furametpyr, furalaxyl, fluacrypyrim, fluazinam, fluoxastrobin, flutrimazole, fluopicolide, fluopyram, fluoroimide, furcarbanil, fluxapyroxad, fluquinconazole, furconazole, furconazole-cis, fludioxonil, flusilazole, flusulfamide, flutianil, flutolanil, flutriafol, furfural, furmecyclox, flumetover, flumorph, proquinazid, prochloraz, procymidone, prothiocarb, prothioconazole, propamocarb, propiconazole, propineb, furophanate, probenazole, bromuconazole, hexachlorobutadiene, hexaconazole, hexylthiofos, bethoxazin, benalaxyl, benalaxyl-M, benodanil, benomyl, pefurazoate, benquinox, penconazole, benzamorf, pencycuron, benzohydroxamic acid, bentaluron, benthiazole, benthiavalicarb-isopropyl, penthiopyrad, penflufen, boscalid, phosdiphen, fosetyl, fosetyl-A1, polyoxins, polyoxorim, polycarbamate, folpet, formaldehyde, machine oil, maneb, mancozeb, mandipropamid, myclozolin, myclobutanil, mildiomycin, milneb, mecarbinzid, methasulfocarb, metazoxolon, metam, metam-sodium, metalaxyl, metalaxyl-M, metiram, methyl isothiocyanate, meptyldinocap, metconazole, metsulfovax, methfuroxam, metominostrobin, metrafenone, mepanipyrim, mefenoxam, meptyldinocap, mepronil, mebenil, iodomethane, rabenzazole, benzalkonium chloride, inorganic microbicides such as basic copper chloride, basic copper sulfate and silver, sodium hypochlorite, cupric hydroxide, wettable sulfur, calcium polysulfide, potassium hydrogen carbonate, sodium hydrogen carbonate, sulfur, copper sulfate anhydride, nickel dimethyldithiocarbamate, copper compounds such as copper-8-quinolinolate (oxine copper), zinc sulfate and copper sulfate pentahydrate.

Further, examples of the herbicides include 1-naphthylacetamide, 2,4-PA, 2,3,6-TBA, 2,4,5-T, 2,4,5-TB, 2,4-D, 2,4-DB, 2,4-DEB, 2,4-DEP, 3,4-DA, 3,4-DB, 3,4-DP, 4-CPA, 4-CPB, 4-CPP, MCP, MCPA, MCPA-thioethyl, MCPB, ioxynil, aclonifen, azafenidin, acifluorfen, aziprotryne, azimsulfuron, asulam, acetochlor, atrazine, atraton, anisuron, anilofos, aviglycine, abscisic acid, amicarbazone, amidosulfuron, amitrole, aminocyclopyrachlor, aminopyralid, amibuzin, amiprophos-methyl, ametridione, ametryn, alachlor, allidochlor, alloxydim, alorac, isouron, isocarbamid, isoxachlortole, isoxapyrifop, isoxaflutole, isoxaben, isocil, isonoruron, isoproturon, isopropalin, isopolinate, isomethiozin, inabenfide, ipazine, ipfencarbazone, iprymidam, imazaquin, imazapic, imazapyr, imazamethapyr, imazamethabenz, imazamethabenz-methyl, imazamox, imazethapyr, imazosulfuron, indaziflam, indanofan, indolebutyric acid, uniconazole-P, eglinazine, esprocarb, ethametsulfuron, ethametsulfuron-methyl, ethalfluralin, ethiolate, ethychlozate-ethyl, ethidimuron, etinofen, ethephon, ethoxysulfuron, ethoxyfen, etnipromid, ethofumesate, etobenzanid, epronaz, erbon, endothal, oxadiazon, oxadiargyl, oxaziclomefone, oxasulfuron, oxapyrazon, oxyfluorfen, oryzalin, orthosulfamuron, orbencarb, cafenstrole, cambendichlor, carbasulam, carfentrazone, carfentrazone-ethyl, karbutilate, carbetamide, carboxazole, quizalofop, quizalofop-P, quizalofop-ethyl, xylachlor, quinoclamine, quinonamid, quinclorac, quinmerac, cumyluron, cliodinate, glyphosate, glufosinate, glufosinate-P, credazine, clethodim, cloxyfonac, clodinafop, clodinafop-propargyl, chlorotoluron, clopyralid, cloproxydim, cloprop, chlorbromuron, clofop, clomazone, chlomethoxynil, chlomethoxyfen, clomeprop, chlorazifop, chlorazine, cloransulam, chloranocryl, chloramben, cloransulam-methyl, chloridazon, chlorimuron, chlorimuron-ethyl, chlorsulfuron, chlorthal, chlorthiamid, chlortoluron, chlornitrofen, chlorfenac, chlorfenprop, chlorbufam, chlorflurazole, chlorflurenol, chlorprocarb, chlorpropham, chlormequat, chloreturon, chloroxynil, chloroxuron, chloropon, saflufenacil, cyanazine, cyanatryn, di-allate, diuron, diethamquat, dicamba, cycluron, cycloate, cycloxydim, diclosulam, cyclosulfamuron, dichlorprop, dichlorprop-P, dichlobenil, diclofop, diclofop-methyl, dichlormate, dichloralurea, diquat, cisanilide, disul, siduron, dithiopyr, dinitramine, cinidon-ethyl, dinosam, cinosulfuron, dinoseb, dinoterb, dinofenate, dinoprop, cyhalofop-butyl, diphenamid, difenoxuron, difenopenten, difenzoquat, cybutryne, cyprazine, cyprazole, diflufenican, diflufenzopyr, dipropetryn, cypromid, cyperquat, gibberellin, simazine, dimexano, dimethachlor, dimidazon, dimethametryn, dimethenamid, simetryn, simeton, dimepiperate, dimefuron, cinmethylin, swep, sulglycapin, sulcotrione, sulfallate, sulfentrazone, sulfosulfuron, sulfometuron, sulfometuron-methyl, secbumeton, sethoxydim, sebuthylazine, terbacil, daimuron, dazomet, dalapon, thiazafluron, thiazopyr, thiencarbazone, thiencarbazone-methyl, tiocarbazil, tioclorim, thiobencarb, thidiazimin, thidiazuron, thifensulfuron, thifensulfuron-methyl, desmedipham, desmetryn, tetrafluron, thenylchlor, tebutam, tebuthiuron, terbumeton, tepraloxydim, tefuryltrione, tembotrione, delachlor, terbacil, terbucarb, terbuchlor, terbuthylazine, terbutryn, topramezone, tralkoxydim, triaziflam, triasulfuron, tri-allate, trietazine, tricamba, triclopyr, tridiphane, tritac, tritosulfuron, triflusulfuron, triflusulfuron-methyl, trifluralin, trifloxysulfuron, tripropindan, tribenuron-methyl, tribenuron, trifop, trifopsime, trimeturon, naptalam, naproanilide, napropamide, nicosulfuron, nitralin, nitrofen, nitrofluorfen, nipyraclofen, neburon, norflurazon, noruron, barban, paclobutrazol, paraquat, parafluron, haloxydine, haloxyfop, haloxyfop-P, haloxyfop-methyl, halosafen, halosulfuron, halosulfuron-methyl, picloram, picolinafen, bicyclopyrone, bispyribac, bispyribac-sodium, pydanon, pinoxaden, bifenox, piperophos, hymexazol, pyraclonil, pyrasulfotole, pyrazoxyfen, pyrazosulfuron, pyrazosulfuron-ethyl, pyrazolate, bilanafos, pyraflufen-ethyl, pyriclor, pyridafol, pyrithiobac, pyrithiobac-sodium, pyridate, pyriftalid, pyributicarb, pyribenzoxim, pyrimisulfan, primisulfuron, pyriminobac-methyl, pyroxasulfone, pyroxsulam, fenasulam, phenisopham, fenuron, fenoxasulfone, fenoxaprop, fenoxaprop-P, fenoxaprop-ethyl, phenothiol, fenoprop, phenobenzuron, fenthiaprop, fenteracol, fentrazamide, phenmedipham, phenmedipham-ethyl, butachlor, butafenacil, butamifos, buthiuron, buthidazole, butylate, buturon, butenachlor, butroxydim, butralin, flazasulfuron, flamprop, furyloxyfen, prynachlor, primisulfuron-methyl, fluazifop, fluazifop-P, fluazifop-butyl, fluazolate, fluroxypyr, fluothiuron, fluometuron, fluoroglycofen, flurochloridone, fluorodifen, fluoronitrofen, fluoromidine, flucarbazone, flucarbazone-sodium, fluchloralin, flucetosulfuron, fluthiacet, fluthiacet-methyl, flupyrsulfuron, flufenacet, flufenican, flufenpyr, flupropacil, flupropanate, flupoxam, flumioxazin, flumiclorac, flumiclorac-pentyl, flumipropyn, flumezin, fluometuron, flumetsulam, fluridone, flurtamone, fluroxypyr, pretilachlor, proxan, proglinazine, procyazine, prodiamine, prosulfalin, prosulfuron, prosulfocarb, propaquizafop, propachlor, propazine, propanil, propyzamide, propisochlor, prohydrojasmon, propyrisulfuron, propham, profluazol, profluralin, prohexadione-calcium, propoxycarbazone, propoxycarbazone-sodium, profoxydim, bromacil, brompyrazon, prometryn, prometon, bromoxynil, bromofenoxim, bromobutide, bromobonil, florasulam,
hexachloroacetone, hexazinone, pethoxamid, benazolin, penoxsulam, pebulate, beflubutamid, vernolate, perfluidone, bencarbazone, benzadox, benzipram, benzylaminopurine, benzthiazuron, benzfendizone, bensulide, bensulfuron-methyl, benzoylprop, benzobicyclon, benzofenap, benzofluor, bentazone, pentanochlor, benthiocarb, pendimethalin, pentoxazone, benfluralin, benfuresate, fosamine, fomesafen, foramsulfuron, forchlorfenuron, maleic hydrazide, mecoprop, mecoprop-P, medinoterb, mesosulfuron, mesosulfuron-methyl, mesotrione, mesoprazine, methoprotryne, metazachlor, methazole, metazosulfuron, methabenzthiazuron, metamitron, metamifop, metam, methalpropalin, methiuron, methiozolin, methiobencarb, methyldymron, metoxuron, metosulam, metsulfuron, metsulfuron-methyl, metflurazon, metobromuron, metobenzuron, methometon, metolachlor, metribuzin, mepiquat-chloride, mefenacet, mefluidide, monalide, monisouron, monuron, monochloroacetic acid, monolinuron, molinate, morfamquat, iodosulfuron, iodosulfuron-methyl-sodium, iodobonil, iodomethane, lactofen, linuron, rimsulfuron, lenacil, rhodethanil, calcium peroxide and methyl bromide.

Examples of the biopesticides include viral formulations such as nuclear polyhedrosis viruses (NPV), granulosis viruses (GV), cytoplasmic polyhedrosis viruses (CPV) and entomopox viruses (EPV); microbial pesticides used as an insecticide or a nematicide, such as *Monacrosporium phymatophagum*, *Steinernema carpocapsae*, *Steinernema kushidai* and *Pasteuria penetrans*; microbial pesticides used as a microbicide, such as *Trichoderma lignorum*, *Agrobacterium radiobactor*, avirulent *Erwinia carotovora* and *Bacillus subtilis*; and biopesticides used as a herbicide, such as *Xanthomonas campestris*. A combined use of the agricultural and horticultural microbicide of the present invention with the foregoing biopesticide as a mixture can be expected to provide the same effect as above.

Other examples of the biopesticides include natural predators such as *Encarsia formosa*, *Aphidius colemani*, *Aphidoletes aphidimyza*, *Diglyphus isaea*, *Dacnusa sibirica*, *Phytoseiulus persimilis*, *Amblyseius cucumeris* and *Orius sauteri*; microbial pesticides such as *Beauveria brongniartii*; and pheromones such as (Z)-10-tetradecenyl acetate, (E,Z)-4,10-tetradecadienyl acetate, (Z)-8-dodecenyl acetate, (Z)-11-tetradecenyl acetate, (Z)-13-icosen-10-one and 14-methyl-1-octadecene.

Hereinafter, the production examples of representative compounds of the present invention and their intermediates will be described in more detail, but the present invention is not limited only to these examples.

EXAMPLES

Example 1

Production Method of methyl 2-[2-(ethylthio)-4-(trifluoromethyl)benzoylamino]-5-heptafluoroisopropyl Benzoate (Compound Number 1-1)

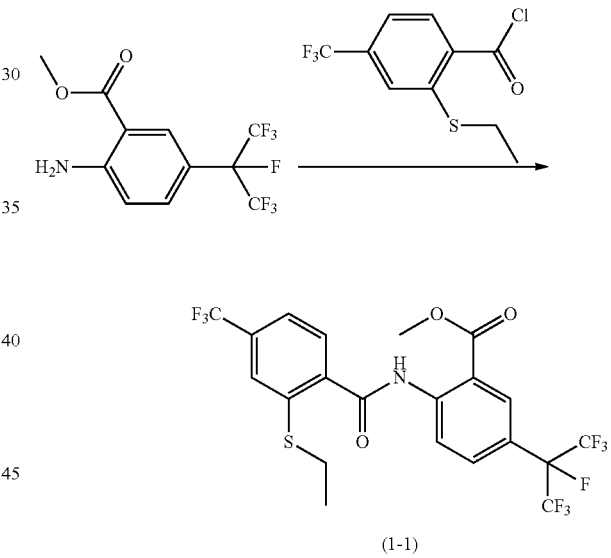

(1-1)

2-Ethylthio-4-trifluoromethyl benzoyl chloride, which was produced by the method of Reference Example 2, was added to 957 mg (3 mmol) of methyl 5-heptafluoroisopropyl anthranilate, which was produced by the method of Reference Example 1. Three drops of pyridine was further added, and the mixture was heated at 100° C. under reflux for 2 hours. The reaction mixture was diluted with ethyl acetate and washed with water. After drying over magnesium sulfate and concentration in vacuo, the residue was purified by silica gel column chromatography (hexane:EtOAc=10:1) to give 655 mg (yield: 40%) of the desired compound as a crystal. EtOAc stands for ethyl acetate.

Example 2

Production Method of methyl 2-[2-(ethylsulfinyl)-4-(trifluoromethyl)benzoylamino]-5-heptafluoroisopropyl benzoate (Compound Number 1-2) and methyl 2-[2-(ethylsulfonyl)-4-(trifluoromethyl)benzoylamino]-5-heptafluoroisopropyl benzoate (Compound Number 1-3)

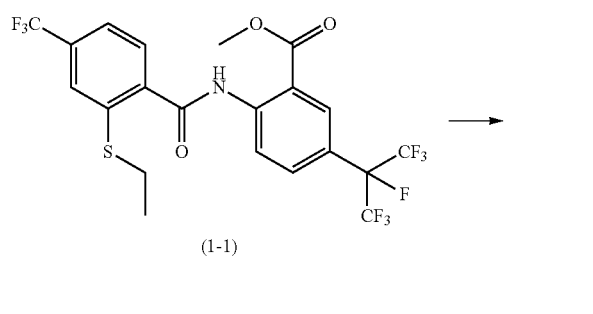

(1-1)

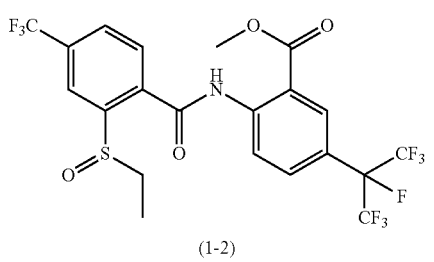

(1-2)

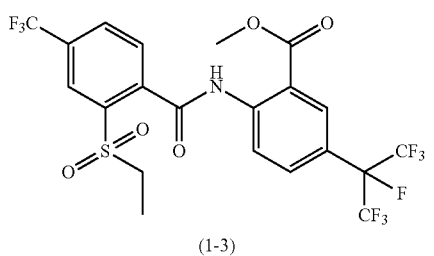

(1-3)

470 mg (0.85 mmol) of the compound (1-1) obtained in the previous step was dissolved in ethyl acetate (10 mL), 345 mg of 65 wt % m-chloroperoxybenzoic acid (m-CPBA) (1.3 mmol) was added to the solution, and the mixture was stirred at room temperature for 4 hours. The reaction mixture was diluted with ethyl acetate, and then washed successively with an aqueous sodium thiosulfate solution, an aqueous sodium bicarbonate solution and water. After drying over magnesium sulfate and concentration in vacuo, the residue was purified by silica gel column chromatography (hexane:EtOAc=9:1→6:1) to give 230 mg (47%) of the compound numbered 1-2 and 220 mg (45%) of the compound numbered 1-3 as crystals.

Example 3

Production Method of methyl 2-[N-acetyl-N-2-(ethylthio)-4-(trifluoromethyl) benzoylamino]-5-heptafluoroisopropyl benzoate (Compound Number 1-7)

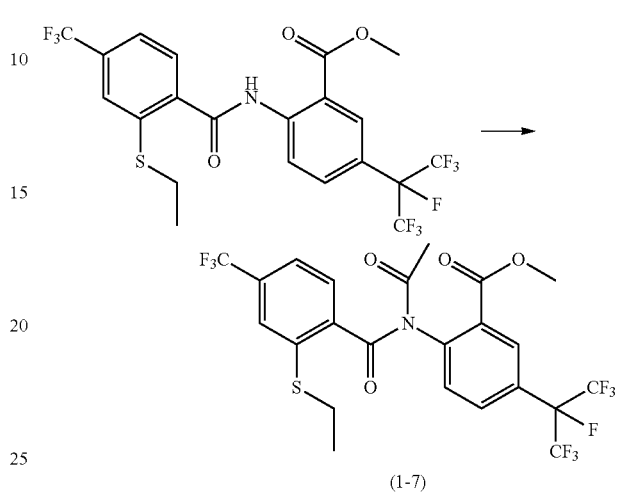

(1-7)

275 mg (0.5 mmol) of compound (1-1) was dissolved in THF (8 mL), and 24 mg of 60% sodium hydride (0.6 mmol) was added to the solution. After heating to 40° C., 71 mg (0.7 mmol) of acetic anhydride was added, and the mixture was stirred for 1 hour. The reaction mixture was diluted with ethyl acetate and then washed with water. After drying over magnesium sulfate and concentration in vacuo, the resulting residue was purified by silica gel column chromatography (hexane:EtOAc=6:1) to give 244 mg (82%) of the compound numbered 1-7 as a paste. THF stands for tetrahydrofuran.

Example 4

Production Method of methyl 2-[2-nitro-4-(trifluoromethyl)benzoylamino]-5-heptafluoroisopropyl benzoate

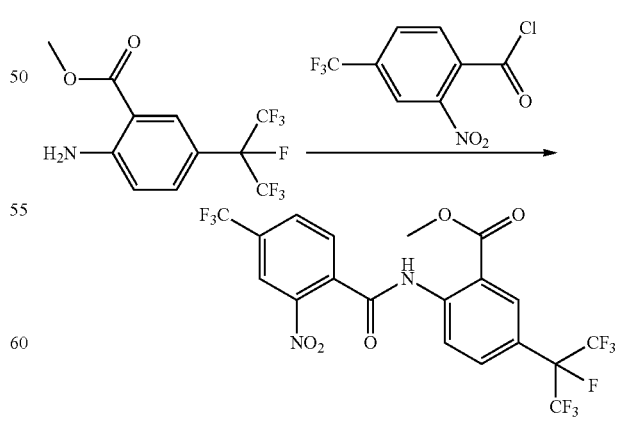

300 mg (1.2 mmol) of 2-nitro-4-trifluoromethyl benzoyl chloride, which was produced in Reference Example 3, was added to 319 mg (1 mmol) of 2-methoxycarbonyl-4-heptafluoroisopropyl aniline. Three drops of pyridine was further added, and the mixture was heated at 90° C. under reflux for 2 hours. The reaction mixture was diluted with ethyl acetate and washed with water. After drying over magnesium sulfate and concentration in vacuo, the residue was purified by silica gel column chromatography (hexane:EtOAc) to give 536 mg (100%) of the desired compound as a crystal.

Example 5

Production Method of methyl 2-[2-ethylthio-4-(trifluoromethyl)benzoylamino]-5-heptafluoroisopropyl benzoate (Compound Number 1-1)

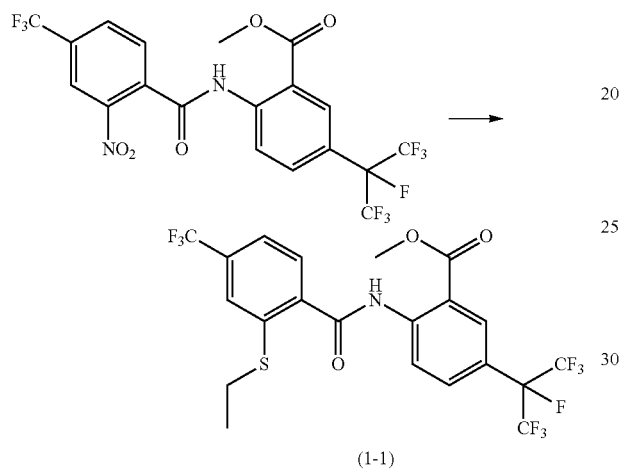

(1-1)

800 mg (1.5 mmol) of the methyl 2-[2-nitro-4-(trifluoromethyl)benzoylamino]-5-heptafluoroisopropyl benzoate produced in Example 4 was dissolved in DMF (16 mL), 236 mg of 80% NaSEt (2.24 mmol) was added to the solution under ice cooling, and the mixture was stirred at room temperature for 2 hours. The reaction mixture was diluted with ethyl acetate and washed with water. After drying over magnesium sulfate and concentration in vacuo, the residue was purified by silica gel column chromatography (hexane:EtOAc) to give 800 mg (97%) of the compound numbered 1-1 as a crystal. NaSEt stands for sodium ethanethiolate.

Example 6

Production Method of methyl 2-[N-acetyl-N-2-(ethylsulfonyl)-4-(trifluoromethyl)benzoylamino]-5-heptafluoroisopropyl benzoate (Compound Number 1-9)

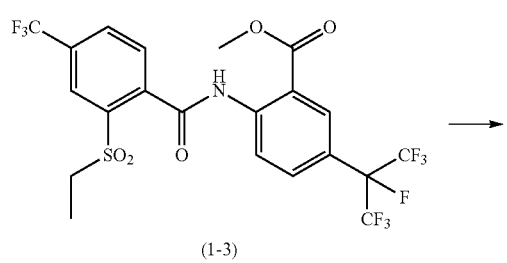

(1-3)

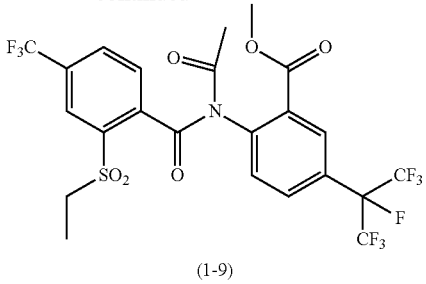

(1-9)

275 mg (0.5 mmol) of the compound (1-3) produced in Example 2 was dissolved in THF (8 mL), and 24 mg of 60% sodium hydride (0.6 mmol) was added to the solution. After heating to 40° C., 71 mg (0.7 mmol) of acetic anhydride was added, and the mixture was stirred for 1 hour. The reaction mixture was diluted with ethyl acetate and then washed with water. After drying over magnesium sulfate and concentration in vacuo, the resulting residue was purified by silica gel column chromatography (hexane:EtOAc) to give 244 mg (82%) of the compound numbered 1-9 as a crystal.

Example 7

Production Method of methyl 2-[N-acetyl-N-2-(ethylsulfinyl)-4-(trifluoromethyl)benzoylamino]-5-heptafluoroisopropyl benzoate (Compound Number 1-8) and methyl 2-[N-acetyl-N-2-(ethylsulfonyl)-4-(trifluoromethyl)benzoylamino]-5-heptafluoroisopropyl benzoate (Compound Number 1-9)

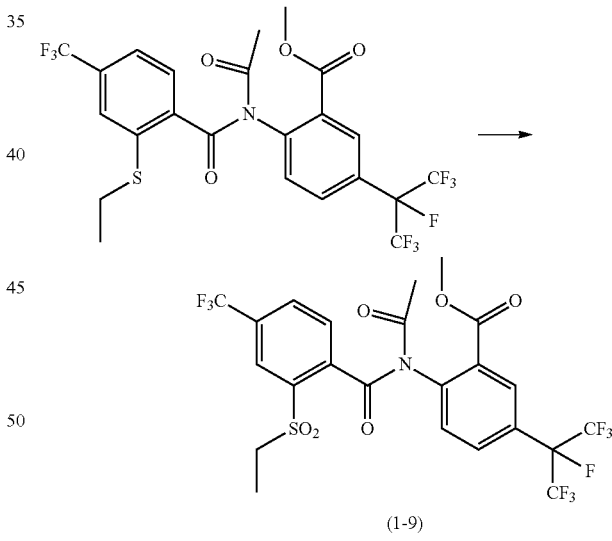

(1-9)

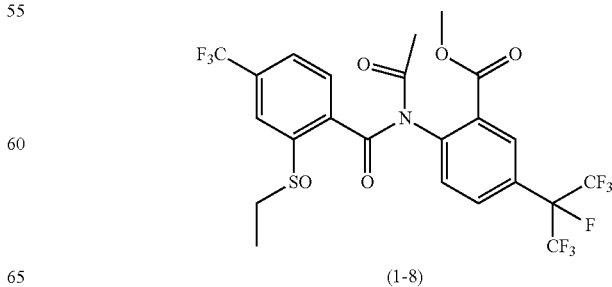

(1-8)

334 mg (0.56 mmol) of the compound (1-7) produced in Example 3 was dissolved in ethyl acetate (10 mL), 200 mg of m-CPBA was added to the solution, and the mixture was stirred at room temperature for 4 hours. The reaction mixture was diluted with ethyl acetate, and then washed successively with an aqueous sodium thiosulfate solution, an aqueous sodium bicarbonate solution and water. After drying over magnesium sulfate and concentration in vacuo, the residue was purified by silica gel column chromatography (hexane:EtOAc) to give 179 mg (52%) of the compound numbered 1-8 and 172 mg (48%) of the compound numbered 1-9.

Reference Example 1

Production Method of methyl 5-heptafluoroisopropyl anthranilate

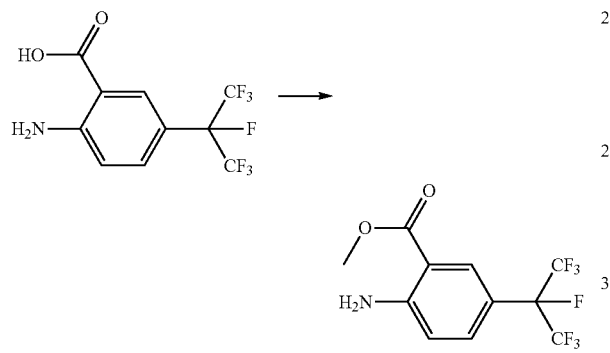

1.5 g (4.9 mmol) of 5-heptafluoroisopropyl anthranilic acid, which was produced by the method described in JP-A 2004-43474 or WO 2013/65725, was dissolved in 10 mL of DMF. 1.01 g (7.3 mmol) of potassium carbonate and 1.03 g (7.3 mmol) of methyl iodide were added to the solution, and the reaction was allowed to proceed at 40° C. for 7 hours. After cooling, the reaction mixture was diluted with 100 mL of ethyl acetate and washed 4 times with water. After drying over magnesium sulfate and concentration in vacuo, the residue was purified by silica gel column chromatography (hexane:EtOAc=9:1) to give 1.36 g (yield: 87%) of the desired compound. DMF stands for dimethylformamide.

Reference Example 2

Production Method of 2-ethylthio-4-trifluoromethyl benzoylchloride

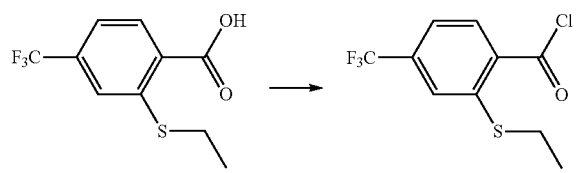 [SMILES: CCSc1cc(C(F)(F)F)ccc1C(=O)O ; CCSc1cc(C(F)(F)F)ccc1C(=O)Cl]

900 mg (3.6 mmol) of 2-ethylthio-4-trifluoromethyl benzoic acid, which was produced by the method disclosed in WO 2012/86848, was dissolved in 10 mL of toluene. 427 mg (3.6 mmol) of thionyl chloride and DMF (2 drops) were added to the solution, and the mixture was refluxed for 3 hours. The reaction mixture was concentrated in vacuo to give 2-ethylthio-4-trifluoromethylbenzoylchloride. This product was used without purification in Example 1.

Reference Example 3

Production Method of 2-nitro-4-trifluoromethyl benzoylchloride

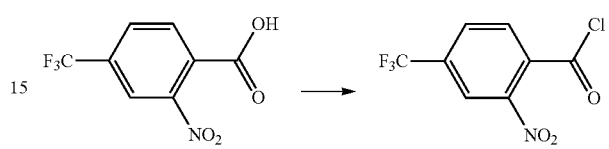

2-Nitro-4-trifluoromethyl benzoyl chloride was produced similarly as described in Reference Example 2. The 2-nitro 4-trifluoromethyl benzoyl chloride was used without purification in Example 4.

Hereinafter, formulation examples are shown, but the present invention is not limited thereto. In the formulation examples, the "parts" means parts by weight.

Formulation Example 1

| | |
|---|---|
| Compound (1) of the present invention | 10 parts |
| Xylene | 70 parts |
| N-methyl pyrrolidone | 10 parts |
| Mixture of polyoxyethylene nonylphenyl ether and calcium alkylbenzene sulfonate | 10 parts |

The above ingredients are uniformly mixed for dissolution to give an emulsifiable concentrate.

Formulation Example 2

| | |
|---|---|
| Compound (1) of the present invention | 3 parts |
| Clay powder | 82 parts |
| Diatomite powder | 15 parts |

The above ingredients are uniformly mixed and then pulverized to give a dust.

Formulation Example 3

| | |
|---|---|
| Compound (1) of the present invention | 5 parts |
| Mixture of bentonite powder and clay powder | 90 parts |
| Calcium lignosulfonate | 5 parts |

The above ingredients are uniformly mixed. After addition of an appropriate volume of water, the mixture is kneaded, granulated and dried to give a granule.

Formulation Example 4

| | |
|---|---|
| Compound (1) of the present invention | 20 parts |
| Kaolin and synthetic high-dispersion silicic acid | 75 parts |
| Mixture of polyoxyethylene nonylphenyl ether and calcium alkylbenzene sulfonate | 5 parts |

The above ingredients are uniformly mixed and then pulverized to give a wettable powder.

Hereinafter, a test example in connection with the present invention is shown, but the present invention is not limited thereto.

Test Example 1

Test of Control Effect on Wheat Powdery Mildew

Agrochemical formulations prepared from the compounds of the present invention according to Formulation Example 1 were diluted with water to a predetermined concentration. The diluted agrochemical formulations were applied to the foliage of wheat plants (variety: Nourin No. 61) grown to the one- to two-leaf stage in pots of 6 cm in diameter. The application amount was 10 mL per pot. After air-dried, the wheat plants were inoculated by sprinkling the conidia of the wheat powdery mildew fungus *Erysiphe graminis*, and kept in a greenhouse. At 7 days after the inoculation, the control effect was evaluated according to the criteria shown below.

Control rate (%)=100×(Average percent lesion area in a non-treatment plot−Average percent lesion area in a treatment plot)/Average percent lesion area in a non-treatment plot Criteria
A: the control rate is 100%.
B: the control rate is 90 to 99%.
C: the control rate is 70 to 89%.
D: the control rate is 50 to 69%.

The results of the above test revealed that the compounds 1-1, 1-2, 1-3, 1-7, 1-8, 1-9, 1-12, 1-18, 1-21, 1-24, 1-25, 1-31, 1-32, 1-33, 1-42, 1-64, 1-66, 3-2, 3-3, 3-5, 3-6, 4-1, 4-4, 4-6, 4-7, 4-9, 4-12, 4-13, 4-18, 4-25, 4-28, 4-30, 4-31, 4-34, 4-36, 4-40, 4-42, 4-54, 5-18, 5-55, 5-57, 5-58, 5-60, 5-61, 5-63, 5-67, 5-69, 6-1, 6-3, 6-4, 6-6, 6-7, 6-9, 6-10, 6-12, 7-3, 7-9, 7-15, 7-19, 7-99, 8-175, 8-177, 8-178, 8-180, 9-142, 10-18 and 10-24 of the present invention showed the activity level evaluated as A at a concentration of 200 ppm.

INDUSTRIAL APPLICABILITY

The anthranilic acid ester compound of the present invention is highly effective for the control of a wide range of agricultural and horticultural diseases and thus is useful.

The invention claimed is:
1. An anthranilic acid ester compound or a salt thereof wherein the compound represented by the formula (1):

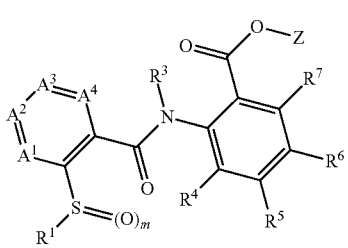

(1)

wherein $R^1$ represents:
(a1) a $(C_1-C_6)$ alkyl group;
(a2) a $(C_2-C_6)$ alkenyl group;
(a3) a $(C_2-C_6)$ alkynyl group;
(a4) a $(C_3-C_6)$ cycloalkyl $(C_1-C_6)$ alkyl group;
(a5) a phenyl group; or
(a6) a phenyl group having, on the ring, 1 to 5 substituting groups which may be the same or different and are selected from the group consisting of (a) a halogen atom, (b) a cyano group, (c) a nitro group, (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group,
$R^3$ represents:
(b1) a hydrogen atom;
(b2) a $(C_1-C_6)$ alkyl group;
(b3) a $(C_2-C_6)$ alkenyl group;
(b4) a $(C_2-C_6)$ alkynyl group;
(b5) a $(C_3-C_6)$ cycloalkyl group;
(b6) a halo $(C_1-C_6)$ alkyl group;
(b7) a $(C_3-C_6)$ cycloalkyl $(C_1-C_6)$ alkyl group;
(b8) a $(C_1-C_6)$ alkoxy $(C_1-C_6)$ alkyl group;
(b9) a $(C_1-C_6)$ alkylcarbonyl group;
(b10) a $(C_1-C_6)$ alkoxycarbonyl group;
(b11) a $(C_3-C_6)$ cycloalkylcarbonyl group;
(b12) a $(C_1-C_6)$ alkoxy $(C_1-C_6)$ alkylcarbonyl group;
(b13) a halo $(C_1-C_6)$ alkylcarbonyl group;
(b14) a $(C_1-C_6)$ alkoxycarbonyl $(C_1-C_6)$ alkyl group; or
(b15) a $(C_1-C_6)$ alkoxy group,
$R^4$, $R^5$, $R^6$ and $R^7$ may be the same or different, and each represent:
(c1) a hydrogen atom;
(c2) a halogen atom;
(c3) a cyano group;
(c4) a nitro group;
(c5) a $(C_1-C_6)$ alkyl group;
(c6) a halo $(C_1-C_6)$ alkyl group;
(c7) a $(C_3-C_6)$ cycloalkyl group;
(c8) a halo $(C_3-C_6)$ cycloalkyl group;
(c9) a $(C_1-C_6)$ alkoxy group;
(c10) a halo $(C_1-C_6)$ alkoxy group;
(c11) a $(C_1-C_6)$ alkylthio group;
(c12) a $(C_1-C_6)$ alkylsulfinyl group;
(c13) a $(C_1-C_6)$ alkylsulfonyl group;
(c14) a halo $(C_1-C_6)$ alkylthio group;
(c15) a halo $(C_1-C_6)$ alkylsulfinyl group;
(c16) a halo $(C_1-C_6)$ alkylsulfonyl group;
(c17) a $(C_1-C_6)$ alkoxy halo $(C_1-C_6)$ alkyl group;
(c18) a phenyl group;
(c19) a phenyl group having, on the ring, 1 to 5 substituting groups which may be the same or different and are selected from the group consisting of (a) a halogen atom, (b) a cyano group, (c) a nitro group, (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group;
(c20) a phenoxy group;
(c21) a phenoxy group having, on the ring, 1 to 5 substituting groups which may be the same or different and are selected from the group consisting of (a) a halogen atom, (b) a cyano group, (c) a nitro group, (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group;
(c22) a pyridyloxy group;
(c23) a pyridyloxy group having, on the ring, 1 to 4 substituting groups which may be the same or different and are selected from the group consisting of
(a) a halogen atom, (b) a cyano group, (c) a nitro
group, (d) a ($C_1$-$C_6$) alkyl group, (e) a ($C_1$-$C_6$)
alkoxy group, (f) a halo ($C_1$-$C_6$) alkyl group and (g)
a halo ($C_1$-$C_6$) alkoxy group;
- (c24) an amino group;
- (c25) an amino group having 1 to 2 substituting groups which may be the same or different and are selected from the group consisting of (d) a ($C_1$-$C_6$) alkyl group, (e) a ($C_1$-$C_6$) alkoxy group, (f) a halo ($C_1$-$C_6$) alkyl group and (g) a halo ($C_1$-$C_6$) alkoxy group;
- (c26) a phenyl ($C_1$-$C_6$) alkoxy group; or
- (c27) a phenyl ($C_1$-$C_6$) alkoxy group having, on the ring, 1 to 5 substituting groups which may be the same or different and are selected from the group consisting of (a) a halogen atom, (b) a cyano group, (c) a nitro group, (d) a ($C_1$-$C_6$) alkyl group, (e) a ($C_1$-$C_6$) alkoxy group, (f) a halo ($C_1$-$C_6$) alkyl group and (g) a halo ($C_1$-$C_6$) alkoxy group, except for a case where $R^4$, $R^5$, $R^6$ and $R^7$ each represent a hydrogen atom, $A^1$ and $A^3$ each represent a C—H group, $A^4$ represents a nitrogen atom or a C—H group, $A^2$ represents a C—$R^2$ group (wherein $R^2$ represents:
- (d2) a halogen atom;
- (d3) a ($C_1$-$C_6$) alkyl group;
- (d4) a ($C_1$-$C_6$) alkoxy group;
- (d5) a halo ($C_1$-$C_6$) alkyl group;
- (d6) a halo ($C_1$-$C_6$) alkoxy group;
- (d7) a ($C_1$-$C_6$) alkylthio group;
- (d8) a ($C_1$-$C_6$) alkylsulfinyl group;
- (d9) a ($C_1$-$C_6$) alkylsulfonyl group;
- (d10) a halo ($C_1$-$C_6$) alkylthio group;
- (d11) a halo ($C_1$-$C_6$) alkylsulfinyl group;
- (d12) a halo ($C_1$-$C_6$) alkylsulfonyl group;
- (d13) a cyclo ($C_3$-$C_6$) alkyl group;
- (d14) a phenyl group;
- (d15) a phenyl group having, on the ring, 1 to 5 substituting groups which may be the same or different and are selected from the group consisting of (a) a halogen atom, (b) a cyano group, (c) a nitro group, (d) a ($C_1$-$C_6$) alkyl group, (e) a ($C_1$-$C_6$) alkoxy group, (f) a halo ($C_1$-$C_6$) alkyl group and (g) a halo ($C_1$-$C_6$) alkoxy group; or
- (d16) a phenoxy group), Z represents:
- (e1) a ($C_1$-$C_6$) alkyl group;
- (e2) a ($C_2$-$C_6$) alkenyl group;
- (e3) a ($C_3$-$C_6$) alkynyl group;
- (e4) a ($C_3$-$C_6$) cycloalkyl group;
- (e5) a cyclo ($C_3$-$C_6$) alkyl ($C_1$-$C_6$) alkyl group;
- (e6) a phenyl ($C_1$-$C_6$) alkyl group; or
- (e7) a cyano ($C_1$-$C_6$) alkyl group, and m represents 0, 1 or 2.

2. The anthranilic acid ester compound or the salt thereof according to claim 1, wherein:

$R^1$ represents:
- (a1) a ($C_1$-$C_6$) alkyl group;
- (a2) a ($C_2$-$C_6$) alkenyl group; or
- (a6) a phenyl group having, on the ring, 1 to 5 substituting groups which may be the same or different and are selected from the group consisting of (a) a halogen atom, (b) a cyano group, (c) a nitro group, (d) a ($C_1$-$C_6$) alkyl group, (e) a ($C_1$-$C_6$) alkoxy group, (f) a halo ($C_1$-$C_6$) alkyl group and (g) a halo ($C_1$-$C_6$) alkoxy group, $R^3$ represents:
- (b1) a hydrogen atom;
- (b2) a ($C_1$-$C_6$) alkyl group;
- (b3) a ($C_2$-$C_6$) alkenyl group;
- (b4) a ($C_2$-$C_6$) alkynyl group;
- (b8) a ($C_1$-$C_6$) alkoxy ($C_1$-$C_6$) alkyl group;
- (b9) a ($C_1$-$C_6$) alkylcarbonyl group;
- (b10) a ($C_1$-$C_6$) alkoxycarbonyl group;
- (b11) a ($C_3$-$C_6$) cycloalkylcarbonyl group;
- (b12) a ($C_1$-$C_6$) alkoxy ($C_1$-$C_6$) alkylcarbonyl group;
- (b13) a halo ($C_1$-$C_6$) alkylcarbonyl group;
- (b14) a ($C_1$-$C_6$) alkoxycarbonyl ($C_1$-$C_6$) alkyl group; or
- (b15) a ($C_1$-$C_6$) alkoxy group, $R^4$, $R^5$, $R^6$ and $R^7$ may be the same or different, and each represent:
- (c1) a hydrogen atom;
- (c2) a halogen atom;
- (c3) a cyano group;
- (c4) a nitro group;
- (c5) a ($C_1$-$C_6$) alkyl group;
- (c6) a halo ($C_1$-$C_6$) alkyl group;
- (c7) a ($C_3$-$C_6$) cycloalkyl group;
- (c9) a ($C_1$-$C_6$) alkoxy group;
- (c10) a halo ($C_1$-$C_6$) alkoxy group;
- (c11) a ($C_1$-$C_6$) alkylthio group;
- (c12) a ($C_1$-$C_6$) alkylsulfinyl group;
- (c13) a ($C_1$-$C_6$) alkylsulfonyl group;
- (c14) a halo ($C_1$-$C_6$) alkylthio group;
- (c15) a halo ($C_1$-$C_6$) alkylsulfinyl group;
- (c16) a halo ($C_1$-$C_6$) alkylsulfonyl group;
- (c17) a ($C_1$-$C_6$) alkoxy halo ($C_1$-$C_6$) alkyl group;
- (c18) a phenyl group;
- (c19) a phenyl group having, on the ring, 1 to 5 substituting groups which may be the same or different and are selected from the group consisting of (a) a halogen atom, (b) a cyano group, (c) a nitro group, (d) a ($C_1$-$C_6$) alkyl group, (e) a ($C_1$-$C_6$) alkoxy group, (f) a halo ($C_1$-$C_6$) alkyl group and (g) a halo ($C_1$-$C_6$) alkoxy group;
- (c21) a phenoxy group having, on the ring, 1 to 5 substituting groups which may be the same or different and are selected from the group consisting of (a) a halogen atom, (b) a cyano group, (c) a nitro group, (d) a ($C_1$-$C_6$) alkyl group, (e) a ($C_1$-$C_6$) alkoxy group, (f) a halo ($C_1$-$C_6$) alkyl group and (g) a halo ($C_1$-$C_6$) alkoxy group;
- (c23) a pyridyloxy group having, on the ring, 1 to 4 substituting groups which may be the same or different and are selected from the group consisting of (a) a halogen atom, (b) a cyano group, (c) a nitro group, (d) a ($C_1$-$C_6$) alkyl group, (e) a ($C_1$-$C_6$) alkoxy group, (f) a halo ($C_1$-$C_6$) alkyl group and (g) a halo ($C_1$-$C_6$) alkoxy group;
- (c25) an amino group having 1 to 2 substituting groups which may be the same or different and are selected from the group consisting of (d) a ($C_1$-$C_6$) alkyl group, (e) a ($C_1$-$C_6$) alkoxy group, (f) a halo ($C_1$-$C_6$) alkyl group and (g) a halo ($C_1$-$C_6$) alkoxy group; or
- (c27) a phenyl ($C_1$-$C_6$) alkoxy group having, on the ring, 1 to 5 substituting groups which may be the same or different and are selected from the group consisting of (a) a halogen atom, (b) a cyano group, (c) a nitro group, (d) a ($C_1$-$C_6$) alkyl group, (e) a ($C_1$-$C_6$) alkoxy group, (f) a halo ($C_1$-$C_6$) alkyl group and (g) a halo ($C_1$-$C_6$) alkoxy group, except for a case where $R^4$, $R^5$, $R^6$ and $R^7$ each represent a hydrogen atom, A¹ and A³ each represent a C—H group,
A⁴ represents a nitrogen atom or a C—H group,
A² represents a C—R² group (wherein R² represents:
(d2) a halogen atom;
(d3) a $(C_1-C_6)$ alkyl group;
(d4) a $(C_1-C_6)$ alkoxy group;
(d5) a halo $(C_1-C_6)$ alkyl group;
(d6) a halo $(C_1-C_6)$ alkoxy group;
(d7) a $(C_1-C_6)$ alkylthio group;
(d8) a $(C_1-C_6)$ alkylsulfinyl group;
(d9) a $(C_1-C_6)$ alkylsulfonyl group;
(d13) a cyclo $(C_3-C_6)$ alkyl group;
(d14) a phenyl group;
(d15) a phenyl group having, on the ring, 1 to 5 substituting groups which may be the same or different and are selected from the group consisting of (a) a halogen atom, (b) a cyano group, (c) a nitro group, (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group; or
(d16) a phenoxy group), and
Z represents:
(e1) a $(C_1-C_6)$ alkyl group;
(e2) a $(C_2-C_6)$ alkenyl group;
(e3) a $(C_3-C_6)$ alkynyl group;
(e6) a phenyl $(C_1-C_6)$ alkyl group; or
(e7) a cyano $(C_1-C_6)$ alkyl group.

3. The anthranilic acid ester compound or the salt thereof according to claim 1, wherein:
R³ represents:
(b1) a hydrogen atom;
(b2) a $(C_1-C_6)$ alkyl group;
(b3) a $(C_2-C_6)$ alkenyl group;
(b4) a $(C_2-C_6)$ alkynyl group;
(b8) a $(C_1-C_6)$ alkoxy $(C_1-C_6)$ alkyl group;
(b9) a $(C_1-C_6)$ alkylcarbonyl group;
(b10) a $(C_1-C_6)$ alkoxycarbonyl group;
(b11) a $(C_3-C_6)$ cycloalkylcarbonyl group; or
(b14) a $(C_1-C_6)$ alkoxycarbonyl $(C_1-C_6)$ alkyl group,
R⁴, R⁵, R⁶ and R⁷ may be the same or different, and each represent:
(c1) a hydrogen atom;
(c2) a halogen atom;
(c6) a halo $(C_1-C_6)$ alkyl group;
(c10) a halo $(C_1-C_6)$ alkoxy group;
(c17) a $(C_1-C_6)$ alkoxy halo $(C_1-C_6)$ alkyl group;
(c18) a phenyl group;
(c19) a phenyl group having, on the ring, 1 to 5 substituting groups which may be the same or different and are selected from the group consisting of (a) a halogen atom, (b) a cyano group, (c) a nitro group, (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group;
(c21) a phenoxy group having, on the ring, 1 to 5 substituting groups which may be the same or different and are selected from the group consisting of (a) a halogen atom, (b) a cyano group, (c) a nitro group, (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group;
(c23) a pyridyloxy group having, on the ring, 1 to 4 substituting groups which may be the same or different and are selected from the group consisting of (a) a halogen atom, (b) a cyano group, (c) a nitro group, (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group;
(c25) an amino group having 1 to 2 substituting groups which may be the same or different and are selected from the group consisting of (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group; or
(c27) a phenyl $(C_1-C_6)$ alkoxy group having, on the ring, 1 to 5 substituting groups which may be the same or different and are selected from the group consisting of (a) a halogen atom, (b) a cyano group, (c) a nitro group, (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group,
except for a case where R⁴, R⁵, R⁶ and R⁷ each represent a hydrogen atom, and
A¹ and A³ each represent a C—H group,
A⁴ represents a nitrogen atom or a C—H group,
A² represents a C—R² group (wherein R² represents:
(d2) a halogen atom;
(d5) a halo $(C_1-C_6)$ alkyl group;
(d6) a halo $(C_1-C_6)$ alkoxy group;
(d13) a cyclo $(C_3-C_6)$ alkyl group;
(d14) a phenyl group; or
(d15) a phenyl group having, on the ring, 1 to 5 substituting groups which may be the same or different and are selected from the group consisting of (a) a halogen atom, (b) a cyano group, (c) a nitro group, (d) a $(C_1-C_6)$ alkyl group, (e) a $(C_1-C_6)$ alkoxy group, (f) a halo $(C_1-C_6)$ alkyl group and (g) a halo $(C_1-C_6)$ alkoxy group).

4. A method of making an agricultural or horticultural microbicide comprising mixing the anthranilic acid ester compound or the salt thereof as set forth in claim 1 with water.

5. A method for treating plants or soil with an agricultural or horticultural microbicide comprising applying an agricultural or horticultural microbicide that comprises the anthranilic acid ester compound or the salt thereof as set forth in claim 1 to a plant or soil.

6. A method for controlling an agricultural or horticultural disease, the method comprising applying an effective amount of an agricultural or horticultural microbicide comprising the anthranilic acid ester compound or the salt thereof as set forth in claim 1 to a plant or soil prior to or after onset of said agricultural or horticultural disease.

7. The method according to claim 6, wherein the agricultural or horticultural disease is powdery mildew.

* * * * *

UNITED STATES PATENT AND TRADEMARK OFFICE
CERTIFICATE OF CORRECTION

PATENT NO. : 10,306,885 B2  
APPLICATION NO. : 15/572107  
DATED : June 4, 2019  
INVENTOR(S) : Takashi Furuya Page 1 of 2

It is certified that error appears in the above-identified patent and that said Letters Patent is hereby corrected as shown below:

In the Specification

In Column 8 Line 60, Change "$R^2$" to --$R^7$--.

In Column 8 Line 66, Change "$R^2$" to --$R^7$--.

In Column 14 Line 6, After "10-2" insert --.--.

In Column 49 Line 62, Change "i-BU" to --i-Bu--.

In Column 49 Line 63, Change "i-BU" to --i-Bu--.

In Column 49 Line 64, Change "i-BU" to --i-Bu--.

In Column 49 Line 65, Change "i-BU" to --i-Bu--.

In Column 49 Line 66, Change "i-BU" to --i-Bu--.

In Column 49 Line 67, Change "i-BU" to --i-Bu--.

In Column 53 Line 1, Before "and" insert --$A^1$--.

In Column 53 Line 22, Before "and" insert --$A^1$--.

In Column 54 Line 3, Change "(Cochiobolus" to --(Cochliobolus--.

In Column 54 Line 10, Change "cichoracoarum)," to --cichoracearum),--.

In Column 54 Lines 13-14, Change "(Microdochiumnivalis," to --(Microdochium Nivale,--.

Signed and Sealed this  
Eighteenth Day of February, 2020

Andrei Iancu  
*Director of the United States Patent and Trademark Office*

CERTIFICATE OF CORRECTION (continued)
U.S. Pat. No. 10,306,885 B2

In Column 54 Line 14, Change "Typhla" to --Typhula--.

In Column 54 Line 14, Change "Typhla" to --Typhula--.

In Column 54 Line 17, Change "Microdochium nivalis)," to --Microdochium Nivale),--.

In Column 54 Line 30, Change "(Elsinoe fawcetti), sugarbeet" to --(Elsinoe fawcettii), sugar beet--.

In Column 54 Lines 54-55, Change "cichoracoarum)," to --cichoracearum),--.

In Column 54 Line 57, Change "(Spaerotheca" to --(Sphaerotheca--.

In Column 61 Line 26, Change "thuringiensisisraelensis," to --thuringiensis israelensis,--.

In Column 61 Line 31, Change "dimethylsulfamoylphenyl" to --dimethylsulfamoylphenyl,--.

In Column 61 Line 41, Change "ethofenprox," to --etofenprox,--.

In Column 61 Line 50, Change "chlorphenapyr," to --chlorfenapyr,--.

In Column 63 Line 48, Change "fosetyl-A1," to --fosetyl-Al,--.

In Column 65 Line 62, Change "radiobactor," to --radiobacter,--.

In Column 71 Line 50, Change "benzoylchloride" to --benzoyl chloride--.

In Column 72 Line 1, Change "trifluoromethylbenzoylchloride." to --trifluoromethyl benzoyl chloride.--.

In Column 72 Line 8, Change "benzoylchloride" to --benzoyl chloride--.